(12) United States Patent
Toth et al.

(10) Patent No.: US 10,363,359 B2
(45) Date of Patent: Jul. 30, 2019

(54) SYSTEMS AND METHODS FOR REGULATING ORGAN AND/OR TUMOR GROWTH RATES, FUNCTION, AND/OR DEVELOPMENT

(71) Applicant: Autonomix Medical, Inc., Excelsior, MN (US)

(72) Inventors: Landy Toth, Doylestown, PA (US); Robert S. Schwartz, Inver Grove Heights, MN (US)

(73) Assignee: AUTONOMIX MEDICAL, INC., Excelsior, MN (US)

( * ) Notice: Subject to any disclaimer, the term of this patent is extended or adjusted under 35 U.S.C. 154(b) by 808 days.

(21) Appl. No.: 14/959,024

(22) Filed: Dec. 4, 2015

(65) Prior Publication Data

US 2016/0082180 A1 Mar. 24, 2016

Related U.S. Application Data

(63) Continuation-in-part of application No. 14/650,485, filed as application No. PCT/US2013/073844 on Dec. 9, 2013.

(Continued)

(51) Int. Cl.
*A61B 18/18* (2006.01)
*A61M 5/14* (2006.01)
(Continued)

(52) U.S. Cl.
CPC ........... *A61M 5/14* (2013.01); *A61B 18/1445* (2013.01); *A61B 18/1492* (2013.01);
(Continued)

(58) Field of Classification Search
CPC ...... A61M 5/14; A61M 5/142; A61M 5/1723; A61M 2005/1726; A61M 2205/051; A61M 2205/058; A61B 18/1445; A61B 18/1815; A61B 2018/00434; A61B 2018/00839; A61B 2018/0212; A61N 2007/0043

See application file for complete search history.

(56) References Cited

U.S. PATENT DOCUMENTS 6,004,269 A * 12/1999 Crowley ............... A61B 8/4461
600/374
6,517,534 B1 2/2003 McGovern et al.
(Continued)

FOREIGN PATENT DOCUMENTS

WO 2007039905 A2 4/2007
WO 2012071573 A2 5/2012
WO PCT/US2013/073844 2/2014

*Primary Examiner* — Lindsey G Wehrheim
(74) *Attorney, Agent, or Firm* — Ryan, Mason & Lewis, LLP

(57) ABSTRACT

A system for controlled neuromodulation procedures is disclosed. A system for controlled micro ablation procedures is disclosed. Systems and methods for imaging, monitoring, stimulating, and/or ablating neurological structures coupled to one or more organs of the lower urinary tract (LUT) are disclosed. Such processes may be used to alter the hormonal secretions from one or more organs, to modulate the growth of an organ, alter the growth rate or rate of perineural invasion of a tumor, or the like. In particular such processes may be used to slow, halt and/or reverse the growth of a prostate gland or a prostate tumor.

24 Claims, 11 Drawing Sheets

Related U.S. Application Data

(60) Provisional application No. 62/087,637, filed on Dec. 4, 2014, provisional application No. 61/735,056, filed on Dec. 9, 2012.

(51) Int. Cl.
  *A61M 5/172* (2006.01)
  *A61M 5/142* (2006.01)
  *A61B 18/14* (2006.01)
  *A61B 18/00* (2006.01)
  *A61B 18/02* (2006.01)
  *A61N 7/00* (2006.01)

(52) U.S. Cl.
  CPC .......... *A61M 5/142* (2013.01); *A61M 5/1723* (2013.01); *A61B 18/1815* (2013.01); *A61B 2018/00434* (2013.01); *A61B 2018/00839* (2013.01); *A61B 2018/0212* (2013.01); *A61M 2005/1726* (2013.01); *A61M 2205/051* (2013.01); *A61M 2205/058* (2013.01); *A61N 2007/0043* (2013.01)

(56) References Cited

U.S. PATENT DOCUMENTS

| | | |
|---|---|---|
| 6,673,068 B1 | 1/2004 | Berube |
| 2004/0138652 A1 | 7/2004 | Berube |
| 2007/0253997 A1 | 11/2007 | Giftakis et al. |
| 2011/0144468 A1 | 6/2011 | Boggs et al. |
| 2012/0101490 A1* | 4/2012 | Smith ................ A61B 17/3203 606/33 |
| 2012/0123303 A1 | 5/2012 | Sogard et al. |

* cited by examiner

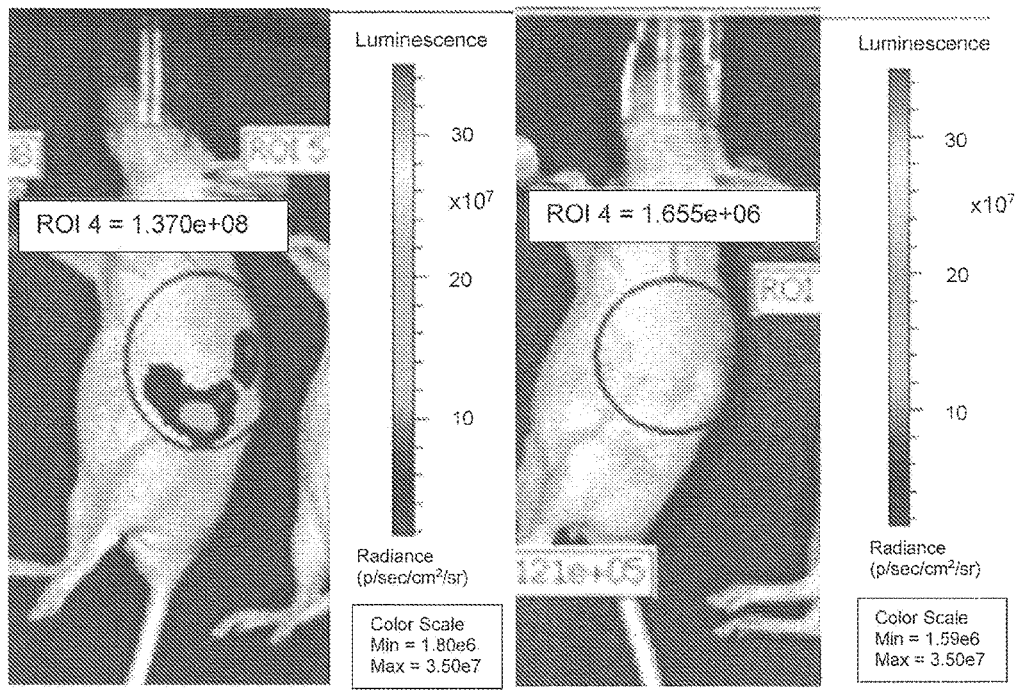
Fig 20a
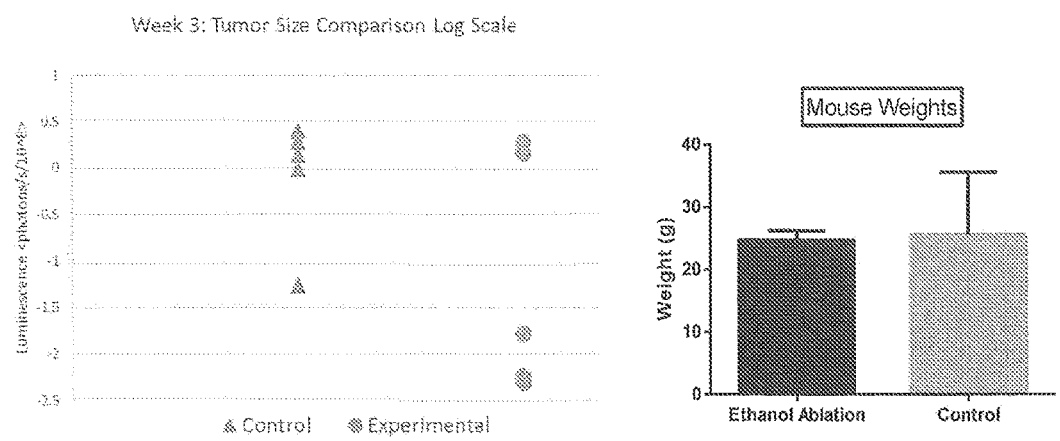
Fig 20b
Fig 20c

SYSTEMS AND METHODS FOR REGULATING ORGAN AND/OR TUMOR GROWTH RATES, FUNCTION, AND/OR DEVELOPMENT

CROSS REFERENCE TO RELATED APPLICATION

The present application claims benefit of and priority to U.S. Provisional Application Ser. No. 62/087,637, filed on Dec. 4, 2014, entitled "Systems and Methods for Regulating Organ and/or Tumor Growth Rates, Function, and/or Development", and is a continuation-in-part application claiming the benefit of and priority to U.S. patent application Ser. No. 14/650,485, filed on Jun. 8, 2015, a national stage application of International Application No. PCT/US2013/073844, which claims benefit of and priority to U.S. Provisional Application Ser. No. 61/735,056 filed on Dec. 9, 2012, entitled "Systems and Methods for Regulating Organ and/or Tumor Growth Rates, Function, and/or Development", the entire contents of which are each incorporated by reference herein.

BACKGROUND

Technical Field

The present disclosure relates to the field of neuromodulation. The present disclosure also relates to methods and systems for use in nerve and/or receptor monitoring, electrophysiological monitoring, and/or surgical procedures, in particular related to the systems and mechanisms that regulate prostate and/or tumor growth. The present disclosure further relates to systems and methods for modulating neurological traffic to and from the prostate, the testis, and/or organs of the lower urinary tract.

Background

As men age, there is an associated increase in the frequency of pathologic diseases affecting the genitourinary tract. The prevalence of lower urinary tract symptoms (LUTS) secondary to benign prostatic hyperplasia (BPH), chronic prostatitis (CP), hypogonadism (HG), nocturia, prostate cancer (PrCa), and erectile dysfunction (ED) continue to rise in the western world.

Relating to one contributor to LUTS, the prevalence of BPH increases with age, with initial development usually after 40 years of age. More than half of men in their 60s and up to 90% of men in their 70s and 80s have some symptoms of BPH. The direct costs of medical services provided in hospital inpatient and outpatient settings, emergency departments, and physician offices for BPH management in the US exceeded $1.1 billion in 2000. Approximately 1 in 5 men with BPH will have a significant clinical event, such as acute urinary retention or prostate surgery, within 1 year of initiating treatment for BPH.

The pathogenesis of these conditions seems to be multifactorial: including age-related changes in the nervous system, and neuroregulatory factors, such as nitric oxide (NO) and RhoA/Rho-kinase. Such disease progression may be associated with the aging process, but many are secondary to comorbid conditions related to aging, such as the metabolic syndrome (MSx), diabetes, hypertension, and hypogonadism.

The success of several widely used pharmacologic interventions in the treatment of LUTS reflects the importance of neuronal influences on urologic disease in aging men.

Relating to the progression of a range of disease states within the body, sympathetic activation can initially be beneficial but eventually becomes maladaptive. Such chronic changes in activity may contribute to the onset and progression of related disease states.

SUMMARY

One objective of this disclosure is to provide systems, devices, and methods for accessing, monitoring and/or treating a surgical site, an organ, and/or tissue within a body.

Another objective is to provide systems, devices, and methods for locating, monitoring, and/or mapping electrophysiological function of one or more surgical sites, organs, and/or tissues before, during, and/or following a stimulus and/or an associated surgical procedure.

Another objective is to provide systems, devices, and methods to modify electrophysiological function of an organ, to modulate intra and/or inter organ neurological traffic, and/or to modulate nervous activity (e.g., sympathetic, parasympathetic, autonomous, enteric, etc.), in a volume of tissue, and/or a surgical site, via a surgical process.

Yet another objective is to provide systems, devices, and methods for regulating the autonomic, sympathetic, and/or parasympathetic traffic to/from, and/or so as to affect the growth rate, hormone secretion rates, or development of an organ (e.g., a prostate, a testicle, etc.), or a tumor (e.g., a prostate cancer tumor, a perineural invading cancerous tumor, etc.).

Another objective is to provide systems, devices, and methods for treating a disease of the lower urinary tract (LUT).

The above objectives are wholly or partially met by devices, systems, and methods according to the appended claims in accordance with the present disclosure. Features and aspects are set forth in the appended claims, in the following description, and in the annexed drawings in accordance with the present disclosure.

According to a first aspect there is provided, a surgical tool for monitoring and/or altering electrophysiological activity within the vicinity of a prostate within a body, the surgical tool including an elongate member with a distal tip, the distal tip shaped and dimensioned so as to fit within a lumen of the body, the elongate member shaped and dimensioned so as to extend from outside the body, through an entry site on the body and into the lumen, and the distal tip including one or more sensing elements, energy delivery elements, and/or chemical delivery elements arranged there upon and coupled to the distal tip such that biasing of the distal tip towards the prostate, engages one or more of the elements with a wall of the lumen.

In aspects, the surgical tool may include one or more imaging elements coupled to the distal tip, configured to couple with tissues in the vicinity of the prostate upon biasing of the distal tip towards the prostate. Some non-limiting examples of imaging elements include one or more of an ultrasound transducer array, an ultrasound element, a transducer, a piezoelectric element, an optical coherence tomography (OCT) element, a capacitive micromachined ultrasound transducer, a camera, an infrared camera, a near infrared camera, a deep tissue penetrating imaging element, a fiber optic array, a combination thereof, or the like.

In aspects, the imaging element may be configured to convey information about a neural structure in the vicinity of the prostate to an operator during operation of the surgical tool. Some non-limiting examples of information include the location, health state, a quantity, blood flow to, blood flow through, temperature, a stiffness, and/or changes therein, of an artery, a vein, a nerve, a neural plexus, a prostatic plexus, a prostatic artery, a dorsal nerve, a cavernous nerve, a vesical plexus, a hypogastric nerve, a splanchnic nerve, a pudendal nerve, an organ, a urethra, the prostate, a reference point, a combination thereof, or the like.

In aspects, one or more of the sensing elements may be configured to monitor one or more physiological signals associated with a tissue in the vicinity of the prostate while engaged with the wall, the electrophysiological signals related to one or more of water concentration, tissue tone, evoked potential, remotely stimulated nervous activity, sympathetic nervous activity, an electromyographic signal [EMG], a mechanomyographic signal [MMG], a local field potential, an electroacoustic event, vasodilation, vessel wall stiffness, muscle sympathetic nerve activity [MSNA], central sympathetic drive, nerve traffic, a combination thereof, or the like.

In aspects, one or more of the sensing elements may include an electrode for monitoring one or more of the physiological signals, and/or may be electrically coupled with a microcircuit, the microcircuit configured to condition one or more of the signals conveyed therefrom.

In aspects, the microcircuit may be embedded into the surgical tool and at least a portion of the electrical coupling may be provided via the elongate member.

In aspects, one or more of the sensing elements may include a microelectrode configured to interface with an adjacent tissue volume within or beyond the wall of the lumen while engaged with the wall, the microelectrode having an area of less than 5000 $\mu m^2$, less than 1000 $\mu m^2$, less than 250 $\mu m^2$, or less than 100 $\mu m^2$.

In aspects, the surgical tool may include a plurality of sensing elements arranged upon and coupled to the distal tip, the sensing elements configured to collectively map electrophysiological activity in the vicinity of the prostate while engaged with the wall.

In aspects, one or more of the energy delivery elements may be configured to provide a radio frequency current, a microwave current, thermal energy, cryoablating action, ultrasound energy, a combination thereof, or the like to a volume of tissue in the vicinity of the prostate while engaged with the wall.

In aspects, one or more energy delivery elements may include one or more stimulating electrodes electrically and mechanically coupled to the distal tip and/or the elongate member, the stimulating electrodes configured to provide a stimulating and/or ablating current to a tissue site in the vicinity of the prostate while engaged with the wall. In aspects, one or more of the stimulating electrodes may have an area of greater than 0.1 $mm^2$, 0.5 $mm^2$, 1 $mm^2$, 2 $mm^2$, or 10 $mm^2$.

In aspects, a surgical tool in accordance with the present disclosure may include a fluid delivery means for providing a coupling fluid to the distal tip to enhance the engagement of one or more of the sensing elements, imaging elements, and/or energy delivery elements with the wall when biased there against, and/or to protect the wall during the passage of energy there through.

In aspects, one or more chemical delivery elements may include one or more probes mechanically, fluidly, and/or electrically coupled with the distal tip, arranged so as to penetrate through the wall upon engagement there with or upon a deployment procedure, one or more of the probes including a lumen configured to deliver a diagnostic and/or therapeutic substance to a tissue site beyond the wall of the lumen, and/or including one or more electrodes each in accordance with the present disclosure.

In aspects, one or more of the sensing elements may be configured to monitor the effect of the diagnostic and/or therapeutic substance on the tissue site and/or tissues related thereto.

In aspects, the diagnostic and/or therapeutic substance may be selected from a chemical, a drug substance, a neuromodulating substance, a neuroblocking substance, an acid, a base, a denervating agent, a combination thereof, or the like.

In aspects, the therapeutic substance may include a neutotoxin, a botulinum toxin, a tetrodotoxin, a tetraethylammonium, a chlorotoxin, a curare, a conotoxin, a bungarotoxin, arsenic, ammonia, ethanol, hexane, nitric oxide, glutamate, resiniferatoxin, alchohol, phenol, capaicin, an anesthetic, lidocaine, tetanus toxin, quaternary ammonium salts, a pachycurare, a leptocurare, acetylcholine, aminosteroids, a combination thereof, or the like.

In aspects, a function of one or more of the energy delivery elements may be coordinated with information from one or more of the sensing elements and/or imaging elements so as to focus energy on a target tissue site in the vicinity of the prostate while minimizing energy delivery to an adjacent tissue site.

In aspects, the lumen may be a rectum, a urethra, an artery, a vein, a duct, or the like.

According to aspects there is provided, a system for monitoring and/or altering electrophysiological activity within the vicinity of a prostate within a body, including a surgical tool in accordance with the present disclosure, configured to perform a surgical procedure, image tissues, and/or monitor electrophysiological activity in the vicinity of the prostate generating one or more signals therefrom, and a control unit configured to accept one or more of the signals from the surgical tool, and to adjust or plan the surgical procedure dependent upon the signals, to display the signals, to evaluate the surgical procedure dependent upon the signals, to plan a surgical path for the surgical procedure dependent upon the signals, and/or to determine the extent of the procedure dependent upon the signals.

In aspects, the surgical procedure may be selected from an ablation, an excision, a cut, a burn, a radio frequency ablation, a cryoablation, a radiosurgical procedure, delivery of energy, an ultrasonic ablation, an abrasion, a biopsy, delivery of a substance, a combination thereof, or the like.

In aspects, the system may include a stimulation and/or ablation electrode configured so as to convey a pulsatile and/or radio frequency signal to a tissue in the vicinity of the prostate or a site coupled thereto via the control unit, the surgical tool configured to convey one or more feedback signals related to the pulsatile and/or radio frequency signal back to the control unit.

In aspects, one or more of the feedback signals may be related to an electrode impedance, a bioimpedance, a local electrical field, and/or an electrophysiological response to the pulsatile and/or radio frequency signal, an analyte level, a hormone level, water concentration, tone, blood oxygen saturation of local tissues, evoked potential, stimulation/sensing of nervous activity, electromyography, temperature, blood pressure, vasodilation, vessel wall stiffness, muscle sympathetic nerve activity (MSNA), central sympathetic drive (e.g., bursts per minute, bursts per heartbeat, etc.), tissue tone, blood flow (e.g., through an artery, through a renal artery), a blood flow differential signal (e.g., a significantly abnormal and or sudden change in blood flow within a structure of the body, a vessel, an organ, etc.), blood perfusion (e.g., to an organ, an eye, etc.), a blood analyte level (e.g., a hormone concentration, norepinephrine, catecholamine, renine, angiotensin II, an ion concentration, a water level, an oxygen level, testosterone, etc.), a state of inflammation within an organ, a change in growth rate of an organ, nerve traffic (e.g., post ganglionic nerve traffic in the peroneal nerve, celiac ganglion, superior mesenteric ganglion, aorticorenal ganglion, renal ganglion, carotid body, splanchnic nerve, hypogastric nerves, testicular plexus, vesical plexus, prostatic plexus, and/or related nervous system structures), combinations thereof, and the like.

In aspects, the control unit may be configured to locate a target treatment site with respect to one or more components of the surgical tool based upon one or more of the signals, and/or to exclude an anatomical site from a surgical procedure based upon one or more of the signals.

According to aspects there is provided, a method for altering the physiological function of a tissue site in the vicinity of a prostate of a subject including altering the function of one or more nerves or neural receptors belonging to and/or coupled to a prostatic plexus of the subject.

In aspects, the altering of function may be accomplished via delivery of energy, and/or delivery of a chemical substance to the nerves, the receptors, the prostatic plexus, or a neural structure coupled thereto.

In aspects, the altering of function may be accomplished via an ablation, an excision, a cut, a burn, a radio frequency ablation, a cryoablation, a radiosurgical procedure, an ultrasonic ablation, an abrasion, delivery of a substance, or a combination thereof.

In aspects, the method may include accessing the nerves, the receptors, or the prostatic plexus with a guidewire or surgical tool inserted into a prostatic artery or an artery coupled thereto, and/or a prostatic venous plexus or vein coupled thereto, wherein the altering of function may be provided at least in part by the guidewire or the surgical tool.

In aspects, the method may include inserting a guidewire or a needle into a hyperplastic lobe of the prostate, the altering of function accomplished at least in part by the guidewire or the needle.

In aspects, the method may include inserting a surgical tool into a rectum of the subject, the altering of function provided at least in part and/or supported by the transrectally inserted surgical tool.

In aspects, the method may include inserting a surgical tool into a urethra of the subject, the altering of function provided at least in part and/or supported by the transurethrally inserted surgical tool.

In aspects, the method may include locating the prostatic plexus or one or more neural structures coupled thereto with an imaging modality selected from computed tomography with or without fluoroscopy, Mill, PET, ultrasound, or the like.

In aspects, the step of accessing may be assisted by injection of a contrast agent into a prostatic artery or an artery coupled thereto.

In aspects, the method may include recording one or more electrophysiological signals in the vicinity of the nerves, the neural receptors, the prostatic plexus, the prostate, a penis, a testicle, or a neural structure related thereto.

In aspects, the method may include confirming, and/or determining the extent of the altering of function based upon the recording.

In aspects, the method may include determining an adverse effect of the altering of function on one or more of the related neural structures based upon the recording, the adverse effect being related to a change in function of the related neural structures, and optionally halting and/or adjusting the altering of function if the adverse effect is substantial.

According to aspects there is provided, a method for altering the physiological function of a tissue site in the vicinity of a testicle of a subject including altering the function of one or more nerves or neural receptors coupled to the testicle.

In aspects, the method may include altering the function of one or more nerves or neural receptors belonging to a testicular plexus of the subject.

In aspects, the altering of function may be accomplished via delivery of energy, and/or delivery of a chemical substance to the nerves, the receptors, the testicular plexus, or a neural structure coupled thereto.

In aspects, the altering of function may be accomplished via an ablation, an excision, a cut, a burn, a radio frequency ablation, a cryoablation, a radiosurgical procedure, an ultrasonic ablation, an abrasion, delivery of a substance, or a combination thereof.

In aspects, the method may include accessing the nerves, the receptors, and/or the testicular plexus with a guidewire or surgical tool inserted into a testicular artery or an artery coupled thereto, the altering of function optionally provided at least in part by the guidewire or the surgical tool.

In aspects, the method may include transcutaneously inserting a needle into the testicular plexus or a neural structure coupled thereto, the altering of function or monitoring thereof accomplished at least in part by the needle.

In aspects, the method may include recording one or more electrophysiological signals in the vicinity of the nerves, the neural receptors, the testicular plexus, the testicle, a ductus deferens, a penis, or a neural structure related thereto, and optionally confirming, and/or determining the extent of the altering of function based upon the recording.

In aspects, the method may include determining an adverse effect of the altering of function on one or more of the related neural structures based upon the recording, the adverse effect being related to a change in function of the related neural structures, and optionally halting and/or adjusting the altering of function if the adverse effect is substantial.

According to aspects there is provided, use of a method in accordance with the present disclosure to alter testosterone production in a body.

According to aspects there is provided, use of a surgical tool, a method, and/or a system each in accordance with the present disclosure to treat a disease of the lower urinary tract.

According to aspects there is provided, use of a surgical tool, a method, and/or a system each in accordance with the present disclosure to treat prostate cancer (PrCa), benign prostatic hyperplasia (BPH), and/or chronic prostatitis (CP).

According to aspects there is provided, use of ipsilateral, contralateral, and/or bilateral neuromodulation, sympathectomy, partial sympathectomy, parasympathectomy, and/or partial parasympathectomy to treat prostate cancer (PrCa), benign prostatic hyperplasia (BPH), and/or chronic prostatitis (CP).

According to aspects there is provided, use of a percutaneously deliverable ablation catheter and/or an ablation guidewire to treat prostate cancer (PrCa), benign prostatic hyperplasia (BPH), and/or chronic prostatitis (CP).

According to aspects there is provided, use of a neuromodulating substance, a neuroblocking substance, a denervating agent, or a combination thereof to treat prostate cancer (PrCa), benign prostatic hyperplasia (BPH), and/or chronic prostatitis (CP).

According to aspects there is provided, use of a surgical tool and/or a system in accordance with the present disclosure, to monitor and/or alter electrophysiological activity in the vicinity of a wall of a bowel, a rectum, an intestine, or a combination thereof.

According to aspects, there is provided a method for blocking at least one of one or more nerves and one or more lymphatic ducts coupled to at least one of a tumor and a metastatic cell within a body. In aspects, the blocking step isolates at least one of the tumor and the metastatic cell within the body. In aspects, the blocking step alters growth rates of at least one of the tumor and metastatic cell within the body. In aspects, the blocking step is performed by injecting a neurolytic agent into at least one of the nerves, the lymphatic ducts and nearby tissue. In aspects, the blocking step includes injecting a mild inflammatory agent into at least one of the nerves and the lymphatic ducts. In aspects, at least one of the one or more nerves and at least one of the one or more lymphatic ducts being blocked is at least 10 mm, 20 mm, or 25 mm in length.

In aspects, the method may include accessing at least one of the nerves and the lymphatic ducts via one of a nearby artery, a vein and a duct.

In aspects, the method provides that the blocking step further comprises altering the structure of a perineural sheath of one or more nerves. In aspects, the blocking step further comprises performing architectural destruction of at least one of nerve tissue and lymphatic ductal tissue via inflammation. In aspects, the blocking step further comprises forming scar tissue along at least one of the nerves and the lymphatic ducts.

In aspects, the method provides that the blocking step further comprises using a single therapeutic compound. In aspects, the compound comprises one of an ablative agent, a migration limiting agent, and an inflammatory accelerating agent. In aspects, the blocking step treats at least one of a tumor, a metastasis migration and cancer pain.

In aspects, the method may include confirming completion of the blocking step. In aspects, confirmation is performed at least in part by at least one of a system, a device, and a sensor positioned within at least one of a nearby tissue site, an artery, a vein, and a duct.

In aspects, the method includes sensing neural traffic along the nerves at least one of before, during, and after the blocking step to at least one of locate the nerves and confirm completion of the block.

In aspects, the method provides that the blocking step, the confirmation step and the sensing step may be performed at least in part by a device in accordance with the present disclosure. In aspects, the device may include a balloon, a basket, a deployable helix, a deployable microneedle, or a combination thereof inserted into at least one of a nearby artery, a vein, and a duct arranged so as to interface with the nerves upon deployment.

According to aspects, a method is provided for blocking at least one of one or more nerves and one or more lymphatic ducts traveling along a lumen coupling a first organ to at least a second organ in a body. In aspects, the blocking step prevents metastasis of a tumor from the first organ to the second organ in the body. In aspects, the first organ is a pancreas and the second organ is one of a spleen, a stomach, a gall bladder and a liver.

In aspects, the method provides that the blocking step further comprises applying energy to at least one of the nerves and lymphatic ducts. In aspects, the energy is thermal energy, radio frequency current, microwave current, ultrasound, radiation, cryotherapy, or a combination thereof.

In aspects, the method provides that the blocking step is performed at least in part by a substance. In aspects, the substance is a medicament, a denervating agent, a sympathetic nerve specific denervating agent, a parasympathetic nerve specific denervating agent, a neuroblocking agent, a highly specific neuroblocking agent, or a combination thereof.

According to aspects, a method is provided for treating neurogenic pathways associated with cancer progression.

BRIEF DESCRIPTION OF THE DRAWINGS

Several aspects of the disclosure can be better understood with reference to the following drawings. In the drawings, like reference numerals designate corresponding parts throughout the several views.

FIG. 20a shows exemplary IVIS images taken with the same settings illustrating median tumor bioluminescence at 3 weeks post procedure in the control group (left) and the EtOH group (right) in accordance with the present disclosure.

FIG. 20b shows exemplary logarithms of the IVIS measured bioluminescence levels at 3 weeks post procedure corresponding to the control group (triangles) and the EtOH group (circles) in accordance with the present disclosure.

FIG. 20c shows a graph illustrating the mass difference between control group and EtOH group at 7 weeks in accordance with the present disclosure.

DETAILED DESCRIPTION

Figure 1:
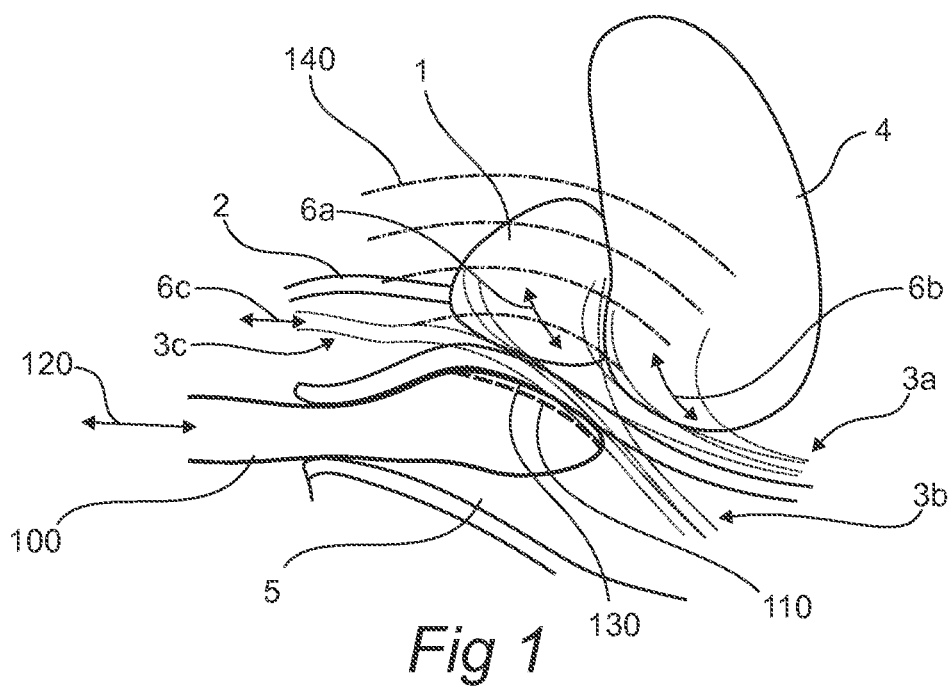
FIG. 1 shows aspects of a system (i.e., the distal end of a surgical tool) configured for transrectal therapy in accordance with the present disclosure.

Particular embodiments of the present disclosure are described herein with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

The present disclosure provides systems and methods for treating medical conditions by neuromodulation of a target site of an autonomic nervous system and more particularly neuromodulation of a target site in communication with a sympathetic nerve chain or a parasympathetic nerve chain.

As used herein, the term "treating" a medical condition encompasses therapeutically regulating, preventing, improving, alleviating the symptoms of, reducing the effects of and/or diagnosing the medical condition. As used herein, the term "medical condition" encompasses any condition, disease, disorder, function, abnormality, or deficit influenced by the autonomic nervous system. Further, the systems and methods of the present disclosure can be used to treat more than one medical condition concurrently. Non-limiting examples of medical conditions that can be treated according to the present disclosure include genetic, skeletal, immunological, vascular or hematological, muscular or connective tissue, neurological, ocular, auditory or vestibular, dermatological, endocrinological, olfactory, cardiovascular, genitourinary, psychological, gastrointestinal, respiratory/pulmonary, neoplastic, or inflammatory medical conditions. Further, the medical condition can be the result of any etiology including vascular, ischemic, thrombotic, embolic, infectious (including bacterial, viral, parasitic, fungal, abscessal), neoplastic, drug-induced, metabolic, immunological, collagenic, traumatic, surgical, idiopathic, endocrinological, allergic, degenerative, congenital, or abnormal malformational causes.

The present systems and methods also encompass enhancing the therapeutic effects of other therapies, such as methods and systems working in conjunction with a pharmaceutical agent or other therapies to augment, enhance, improve, or facilitate other therapies (adjunctive therapies) as well as reducing/minimizing and counteracting side effects, complications and adverse reactions for any therapies involved in treating the above-mentioned medical conditions. For example, the methods and systems of the present disclosure may be used for a cancer patient undergoing chemotherapy utilizing stimulation and/or sympathectomy to minimize the adverse effects of chemotherapy, influence the development of a tumor, etc. In contrast, the methods and systems can be used to enhance chemotherapy.

In aspects, one or more organs or target tissue sites to be treated in accordance with the present disclosure may be accessed via incision, via rectum, transurethral access, transcutaneous access, interventionally (e.g., access via the femoral artery, access to nerve plexuses running along arteries serving one or more of the organs in question, etc.).

In aspects, direct modulation of nerve structures near to the prostate and/or testis, in combination with measurement, the response of which may be used to select more distant nerve targets for modulation (e.g., temporary, prolonged, or substantially permanent modulation). Such direct modulation may be provided by a method or system in accordance with the present disclosure with stimulation and/or energy delivery aspects sized and configured for interfacing with one or more sites within the rectum, accessing the target sites via needle access, and/or through trans lumen access (e.g., via a urethra, an artery, a vein, etc.).

In aspects, a system or method in accordance with the present disclosure may be used so as to affect androgen production in the testis.

In aspects, a method in accordance with the present disclosure may include applying neuromodulation to one or more nerves coupled to the testis so as to affect androgen production in the testis.

In aspects, a system in accordance with the present disclosure may include a probe shaped and dimensioned for transrectal access to the nerves of the LUT, the probe including an array of sensing and/or energy delivery elements, arranged upon a face of the probe such that the energy delivery elements may be biased towards the nerves. In aspects, the probe may include one or more imaging elements (ultrasound, OCT element(s), etc.). In aspects, the array may include one or more sensing elements in accordance with the present disclosure. Some non-limiting sensing elements include electrodes, photodetectors, photodiode/photodetector pairs, pressure sensors (i.e., to determine the contact pressures between a face of the probe and the adjacent tissue surfaces), etc. In aspects, the system may include a feedback subsystem for conveying the sensory information obtained by one or more sensors and/or imaging element to an operator (such as via audible feedback, via visual feedback, mapping, etc.). Additional details relating to the sensing can be found in U.S. patent application Ser. No. 14/374,466, entitled "Controlled Sympathectomy and Micro-Ablation Systems and Methods," which is incorporated by reference herein.

Such a feedback subsystem may be configured so as to convey changes in electrophysiological activity and/or structure of the nerves before, during, and/or after a neuromodulation procedure.

In aspects, the array may be configured such that elements thereof are arranged longitudinally along the rectum, circumferentially around the rectum, or in combinations thereof to access, interface with, and/or treat adjacent tissues during a procedure.

In aspects, the surgical system may include other functionality including: angiographic die delivery, saline delivery, temperature monitoring, intra and extra vascular coordination between devices, through wall imaging, through wall current flow, saline provision for internal arterial or rectal cooling, and the like. In one non-limiting example, the surgical system may include means for delivering a cooling fluid (e.g., saline), into the rectum so as to maintain an anatomically safe tissue temperature within the rectal tissues in immediate vicinity to a face of the surgical tool during a procedure. Such a configuration may be advantageous to minimize collateral damage during treatment process. In aspects, the cooling fluid may be used to enhance coupling between one or more elements of the array (e.g., energy delivery elements, sensing elements, imaging elements, etc.), and the surrounding tissues during a procedure (e.g., a neuromodulation procedure, an imaging procedure, electrophysiological monitoring, etc.).

In aspects, a method in accordance with the present disclosure may include identifying one or more nerves on or coupled to a prostate, identifying one or more nerves which are on located on the front (i.e., facing towards the penis), which are located behind (i.e., facing towards the bladder), identifying which nerves are to be treated, which nerves are to be preserved (such as nerves serving sensory function of the penis), and then directing the treatment of one or more of the nerves accordingly.

In aspects, the function of the nerves (i.e., those that it is desirable to treat and those it is desirable to preserve) may be monitored and/or assessed during the treatment. The functional monitoring may be provided via one or more methods in accordance with the present disclosure (e.g., direct electrophysiological monitoring of nerve traffic, evoked potential testing, conduction block testing, etc.). In aspects, the functional monitoring may be used to determine when the procedure is completed, determine procedure dose, direct/redirect the procedure away from nerves that are to be preserved, etc.

In aspects, a method in accordance with the present disclosure may include inserting a substance delivery device, such as a needle, directly into the prostate, or a nerve/nerve plexus coupled thereto and injecting a chemical denervation agent in accordance with the present disclosure into the tissues so as to provide the desired denervation. The method may include directing the delivery device into the organ/nerve (such as with an imaging probe, via an imaging modality (e.g., via CT, MM, PET, etc.)).

In aspects, a method in accordance with the present disclosure may include cutting through tissue to reach the selected anatomy, inspecting the selected anatomy, visualizing which tissues are to be treated, which are to be preserved, and the like, and applying the appropriate surgical procedures to treat the tissues.

In aspects, the method may include treating the LUT organ, and/or nerves coupled thereto via a radiosurgical approach, etc. (e.g., such as by using a CyberKnife™ to thermally/radiosurgically affect the target tissues), as identified in images created by an associated imaging system (e.g., an Mill, CT, PET scan, etc.).

In aspects, one or more steps of a method and/or one or more aspects of a surgical tool each in accordance with the present disclosure may be accomplished by and/or coupled to a robotic surgical system (e.g., a DaVinci System™, etc.).

In aspects, a method in accordance with the present disclosure may include considering nerve locations, imaging nerves, mapping nerves, etc.

In aspects, a method may include diagnosing and/or treatment of one or more neurological structures. Such diagnostics may be performed with an ultrasonic probe (e.g., an ultrasonic probe to assess the state of the organ, if the organ is large, if the organ has changed since the last checkup, etc.), an electrophysiological monitor (e.g., an electrode array configured to monitor neural traffic in the vicinity of the organ, to determine a baseline activity, etc.). The method may include performing a surgical procedure in accordance with the present disclosure if the diagnostic step indicates that such a procedure is necessary (e.g., the organ growth rate is abnormally high, excess neural traffic is present around the organ, an abnormally high degree of innervation is visualized around the organ, etc.).

A method in accordance with the present disclosure may include assessing one or more properties of the organ (e.g., size, diameter, change in anatomy, urethral opening, etc.), before, after treatment, as part of a screening procedure, as part of a follow up procedure (e.g., after 1 month, 6 months, 1 year, 5 years, etc.), or the like.

According to aspects, there is provided a method for blocking at least one of one or more nerves and one or more lymphatic ducts coupled to at least one of a tumor and a metastatic cell within a body. In aspects, the blocking step isolates at least one of the tumor and the metastatic cell within the body. In aspects, the blocking steps alters growth rates of at least one of the tumor and metastatic cell within the body. In aspects, the blocking step is performed by injecting a neurolytic agent into at least one of the nerves, the lymphatic ducts and nearby tissue. In aspects, the blocking step includes injecting a mild inflammatory agent into at least one of the nerves and the lymphatic ducts. In aspects, at least one of the one or more nerves and at least one of the one or more lymphatic ducts being blocked is at least 10 mm, 20 mm, or 25 mm in length. In aspects, the neurolytic agent may be ethanol. In aspects, the mild inflammatory agent may be ethanol, poly(lactic-co-glycolic acid) (PLGA), polysaccharides, collagen, silica particles, carbon micro or nanoparticles, microbeads, etc.

In aspects, injection of the mild inflammatory agent may be performed through the wall of the artery to minimize collateral damage to the surrounding tissues. In aspects, microneedles, either with or without sensing capability, may be inserted through the wall of the vessel. In aspects, the mild inflammatory agent may be delivered into the adventitia around the vessel, where the nerves are situated. In aspects, neural traffic may be sensed with sensing enabled microneedles (or other means if the microneedles do not have sensing capability). In aspects, the method includes determining whether the microneedles are close to the nerves, releasing the mild inflammatory agent when the microneedles are close to the nerves, monitoring the nerves (e.g., via changes in traffic), and pulling out the microneedles to finish the procedure.

In aspects, blocking may refer to the blocking of neural traffic along a nerve (such as via disrupting the function of the nerve at one or more sites thereupon, over stimulating the nerve so as to functionally block traffic thereupon, changing the electrical potentials around the nerve, altering the ionic concentrations in and/or around the nerve, and/or destroying one or more functional features of the nerve at one or more sites thereupon). In aspects, blocking may refer to physically blocking the channel taken up by the nerve (i.e., the physical space taken up by the nerves, which form channels through an associated tissue volume). Such physical blocking may be useful to limit axonal regrowth of the nerve after the procedure, to disrupt channel pathways, which may facilitate cell migration, or the like. For example, inflammation may be induced to close off the channels and limit or hinder nerve regrowth after the procedure.

In aspects, the method may include accessing at least one of the nerves and the lymphatic ducts via one of a nearby artery, a vein and a duct.

In aspects, the method provides that the blocking step further comprises altering the structure of a perineural sheath of one or more nerves. In aspects, the blocking step further comprises performing architectural destruction of at least one of nerve tissue and lymphatic ductal tissue via inflammation. In aspects, the blocking step further comprises forming scar tissue along at least one of the nerves and the lymphatic ducts.

In aspects, architectural destruction of at least one of nerve tissue and lymphatic ductal tissue may be effected by a mild inflammatory agent. In aspects, architectural destruction of at least one of nerve tissue and lymphatic ductal tissue may be effected by a dedicated ingredient in a substance, such as, but not limited to, silica and PLGA beads.

In aspects, the method provides that the blocking step further comprises using a single therapeutic compound. In aspects, the compound comprises one of an ablative agent, a migration limiting agent, and an inflammatory accelerating agent. In aspects, the blocking step treats at least one of a tumor, a metastasis migration and cancer pain.

In aspects, the method may include confirming completion of the blocking step. In aspects, confirmation is performed at least in part by at least one of a system, a device, and a sensor positioned within at least one of a nearby tissue site, an artery, a vein, and a duct.

In aspects, the method includes sensing neural traffic along the nerves at least one of before, during, and after the blocking step to at least one of locate the nerves and confirm completion of the block.

According to aspects, a method is provided for blocking at least one of one or more nerves and one or more lymphatic ducts traveling along a lumen coupling a first organ to at least a second organ in a body. In aspects, the blocking step prevents metastasis of a tumor from the first organ to the second organ in the body. In aspects, the first organ is a pancreas and the second organ is one of a spleen, a stomach, a gall bladder and a liver.

In aspects, the method provides that the blocking step further comprises applying energy to at least one of the nerves and lymphatic ducts. In aspects, the energy is thermal energy, radio frequency current, microwave current, ultrasound, radiation, cryotherapy, or a combination thereof.

In aspects, the method provides that the blocking step is performed at least in part by a substance. In aspects, the substance is a medicament, a denervating agent, a sympathetic nerve specific denervating agent, a parasympathetic nerve specific denervating agent, a neuroblocking agent, a highly specific neuroblocking agent, or a combination thereof.

According to aspects, a method is provided for treating neurogenic pathways associated with cancer progression.

FIG. 1 shows aspects of a system (i.e., the distal end of a surgical tool 100) configured for transrectal therapy in accordance with the present disclosure. The Figure shows a prostate 1, a urethra 2, a bladder 4, and a rectum 5 arranged within a subject. The distal end of a surgical tool 100 in accordance with the present disclosure is positioned within the rectum 5 of the subject, biased towards the prostate 1. The surgical tool may include one or more energy delivery elements 110, imaging elements, sensing elements, chemical delivery elements, probes, electrodes, or the like, each in accordance with the present disclosure. The surgical tool 100 may be configured so as to image, monitor, and/or treat one or more regions of the prostate 1, and/or nerves 3a, 3b, 3c coupled thereto or in the vicinity thereof.

As shown the surgical tool 100 includes an elongate member generally extending from a site, connector, handle, etc. located outside of the body of the subject, and shown extending into the body through the anus of the rectum 5. The surgical tool 100 includes a distal tip, generally including the distal most portion of the surgical tool 100 where the one or more energy delivery elements, imaging elements, sensing elements, probes, electrodes, or the like are located on the surgical tool 100.

The nerves 3a, 3b, 3c may be coupled 6a, 6b, 6c to the prostate 1, the bladder 4, or the penis (not explicitly shown). Depending on the procedure, one or more of the nerves 3a, 3b, 3c may be targeted for monitoring and/or as part of a surgical procedure.

The surgical tool 100 may include an array of electrodes each in accordance with the present disclosure. The electrodes may be arranged along a face 130 of the surgical tool 100, such that when the tool 100 is biased against a wall of the rectum 5, towards the prostate 1 or nerves 3a, 3b, 3c in the vicinity thereof, the electrodes may be brought into intimate contact with the prostate 1 and/or nerves 3a, 3b, 3c through the wall of the rectum 5. In aspects, the electrodes may be configured to communicate energy to the prostate 1 or one or more of the nerves 3a, 3b, 3c as part of a surgical procedure. In aspects, the electrodes may be configured to monitor electrophysiological signals in the vicinity thereof, to map, locate, identify, monitor, and/or evaluate function of the prostate 1, and/or nerves 3a, 3b, 3c.

The surgical tool 100 may be coupled 120 to a controller and/or one or more circuits each in accordance with the present disclosure. The controller and/or circuits may be configured to interface with one or more of the energy delivery elements 110, imaging elements, probes, electrodes, or the like included in the distal tip of the surgical tool 100.

In aspects, the surgical tool 100 may include one of more imaging elements in accordance with the present disclosure, such as an ultrasound transducer. The imaging element may be configured to send energy 140 towards or receive energy from the prostate 1, or the nerves 3a, 3b, 3c, so as to image one or more aspects thereof, as part of a procedure.

In aspects, the surgical tool 100 may include a means for delivering fluid to the face 130 during a procedure. Such a configuration may be advantageous to cool the wall of the rectum 5 during energy delivery to the surrounding tissues, but may also be advantageous for improving electrical, mechanical, and or acoustic coupling of the energy delivery elements 110, imaging elements, probes, electrodes, or the like with the wall of the rectum 5 during a procedure.

Figure 2:
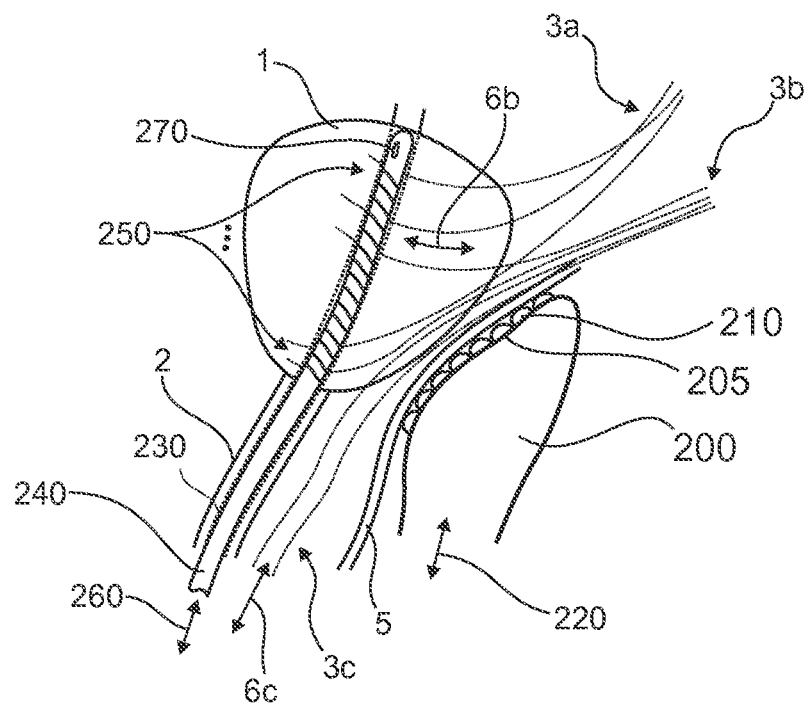
FIG. 2 shows aspects of a system configured for a combination of transrectal and transurethral therapy in accordance with the present disclosure.

FIG. 2 shows aspects of a system configured for a combination of transrectal and transurethral therapy in accordance with the present disclosure. The system includes a transrectally insertable surgical tool 200 sized and shaped so as to be inserted into the rectum 5 of a subject, the transrectally insertable tool including one or more faces 205 arranged along the tip of the transrectally insertable tool 200 such that it can be biased against a wall of the rectum 5 to interface with one or more organs (e.g., prostate 1, urethra 2, bladder, nerves 3a, 3b, 3c) during a surgical procedure, a diagnostic test, a follow-up procedure, or the like. The face 205 may include one or more electrodes 210 or probes configured for interfacing with tissues in the vicinity thereof during a surgical procedure. The transrectally insertable surgical tool 200 may be coupled to a controller 220 or one or more circuits in accordance with the present disclosure, the controller 220 or circuits coupled to one or more of the electrodes 210, configured to delivery energy to surrounding tissues, monitor and/or modulate electrophysiological activity, provide feedback to an operator, etc. during a surgical procedure. Such electrophysiological activity may include afferent and efferent nerve traffic 6b, 6c along prostate nerves 3a and bladder nerves 3c respectively.

The system includes a transurethrally insertable surgical tool 230, including an elongate member 240 for coupling and communicating between a distal tip thereof and a controller 260 or circuit each in accordance with the present disclosure. The elongate member 240 includes one or more sensors, electrodes 250, or the like, configured to interface with a surrounding tissue, and/or the transrectally insertable surgical tool 200 during a surgical procedure. The elongate member 240 may include a lumen and a port 270 for providing a fluid, a cooling agent, a medication, a denervating agent, etc. as part of a diagnostic test, a surgical procedure, a monitoring procedure, etc.

In aspects, the face 205 may include one or more probes in accordance with the present disclosure, the probes arranged in a protruding configuration from the face 205, one or more probes configured to bias into, or penetrate through the wall of the rectum 5 during a procedure.

In aspects, the elongate member 240 may include one or more probes in accordance with the present disclosure, slidingly attached thereto, the probes being configured and arranged so as to be deployably inserted into the tissues of the prostate 1 during a procedure.

Figure 3A:
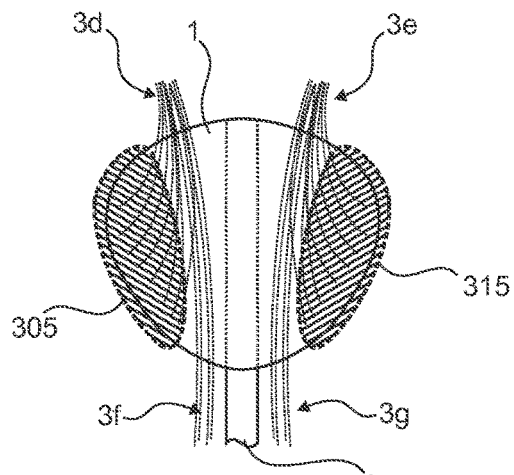
FIGS. 3a, 3b show aspects of an organ related to a treatment performed by a system in accordance with the present disclosure.
Figure 3B:
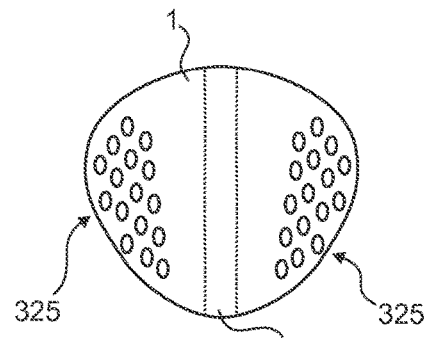

FIGS. 3a-3b show aspects of an organ related to a treatment performed by a system in accordance with the present disclosure. A prostate 1, a urethra 2, and corresponding nerves 3d-g are shown schematically along with non-limiting examples of zones 305, 315 for treatment or monitoring of one or more nerves coupled to the prostate 1. Such treatment or monitoring may be provided by one or more surgical tools in accordance with the present disclosure. In aspects, the surgical tool may be configured to ablate the nerves 3d, 3e serving the prostate 1, while preserving the nerves 3f, 3g serving the penis (not explicitly shown).

FIG. 3b shows a schematic of a prostate 1, with a urethra 2, illustrating a pattern of microablations 325 applied to one or more nerves coupled to the prostate 1. Such an ablation pattern 325 may be created by a transrectally insertable surgical tool in accordance with the present disclosure. The pattern 325 may be formed in conjunction with electrophysiological feedback with a tool in accordance with the present disclosure. In aspects, the electrophysiological feedback may be used to determine if the target nerves have been sufficiently treated, to determine if the nerves to be preserved are healthy, to determine if the prostate 1 has been sufficiently neurologically disconnected from other neural circuits in the body, etc.

In aspects, the ablation pattern 325 may be formed via delivery of RF current from one or more electrodes or probes in accordance with the present disclosure. In one non-limiting example, the ablation pattern 325 may be formed by an array of electrodes arranged along a face of a transrectally insertable surgical tool in accordance with the present disclosure.

In aspects, the ablation pattern 325 may be essentially formed via ablation of nerves located in the vicinity of an artery, coupled to the prostate 1 through which a minimally invasive tool may be inserted as part of a surgical procedure in accordance with the present disclosure. Such an approach may be advantageous as the location of the surgical tool within the artery can be confirmed via imaging, fluoroscopy, etc. and the nerves traveling along the artery can be verified as serving only the organ of interest (i.e., in this case the prostate 1).

Figure 4A:
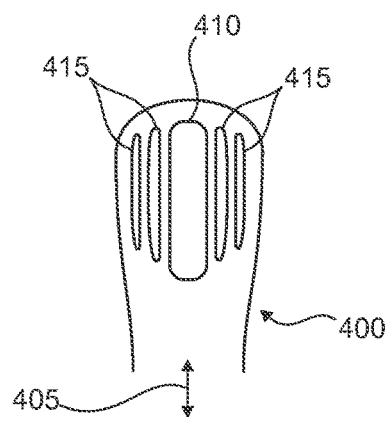
FIGS. 4a-4d show aspects of surgical tools in accordance with the present disclosure.

FIGS. 4a-4d show aspects of surgical tools in accordance with the present disclosure. FIG. 4a shows a schematic of a distal tip of a transrectally insertable surgical tool 400 including an imaging element 410 and electrodes 415 arranged along a face of the surgical tool 400. The surgical tool 400 may be arranged with the face configured so as to image one or more regions of a prostate and/or one or more associated nerves through the wall of the rectum as part of an imaging procedure. The imaging procedure may be used to assist with locating target nerves, positioning the surgical tool 400 with respect to the prostate, determine which nerves are to be preserved, provide a user with one or more "keepout" zones for treatment, etc. The imaging head 410 may include one or more ultrasound transducer arrays, ultrasound elements, a transducer, a piezoelectric element, an OCT element, a capacitive micromachined ultrasound transducer, a camera, an infrared camera, a near infrared camera, a deep tissue penetrating imaging element, a fiber optic array, or the like to image, locate, and interface with one or more tissues in the vicinity of the target organ or nerves.

In aspects, the electrodes 415 may be provided in accordance with the present disclosure, configured to deliver energy to the tissues as part of a surgical procedure, etc.

In aspects, the electrodes 415, and imaging head 410 may be coupled 405 to a controller or circuit each in accordance with the present disclosure.

Figure 4B:
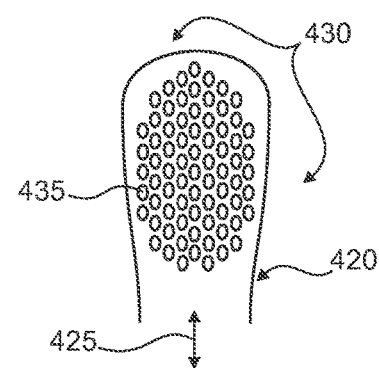

FIG. 4b illustrates a distal tip of a transrectally insertable surgical tool 420 including a contoured surface for easy placement into the rectum of a subject as part of a surgical procedure. The surgical tool 420 includes an array 430 of electrodes 435 each in accordance with the present disclosure configured to interface with adjacent tissues during a procedure. One or more electrodes 435 may include a non-stick coating, be coupled to a cooling element, etc. in order to assist with the flow of energy and/or protect the surrounding tissues during a procedure.

One or more of the electrodes 435 may be coupled 425 to a controller in accordance with the present disclosure. Energy may be directed into the surrounding tissues via electrodes 435 in the array 430, the pattern, penetration depth, etc. being a function of the enlisted electrodes 435, control of current flow through the electrodes, completion of the circuit with a counter electrode arranged elsewhere on the body (e.g., transurethrally, within the bladder, on the skin, etc.), between electrodes, etc. In aspects, the controller may include a switching array, and optionally feedback to assist with the management of current flow through the electrodes.

The system may include or be coupled to a display to summarize and assist with visualization of current flow for an operator (i.e., so as to assist with ensuring only the target tissues are treated with a procedure, etc.).

Figure 4C:
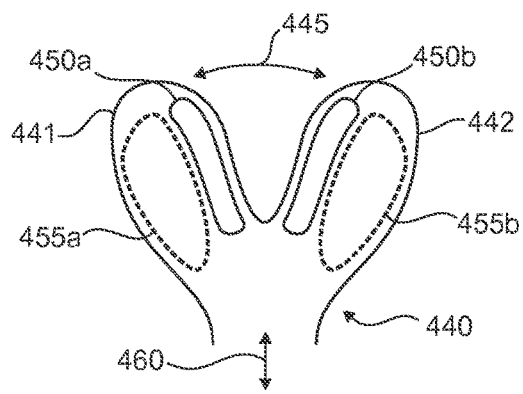

FIG. 4c shows a schematic of a distal tip of a transrectally insertable surgical tool 440 in accordance with the present disclosure. The surgical tool 440 includes dual tips 441, 442 and a deployment mechanism such that the dual tips 441, 442, may be closely packed during delivery to the surgical site and may be actuated 445 so as to form a cupping surface. Such a configuration may be advantageous for providing a simple delivery means, but also allowing for control of the positioning of the treatment zone as well as for cupping the target organ (i.e., a prostate 1), for providing treatment thereto or to nerves in the vicinity thereof.

The dual tips 441, 442 may include first regions 450*a,b* designated for monitoring or imaging the adjacent tissues, as well as second regions 455*a,b* designated for monitoring or treating adjacent tissues. Such regions 450*a,b*, 455*a,b* may include one or more imaging elements, sensing elements, probes, electrodes, energy delivery means, fluid delivery means, or the like each in accordance with the present disclosure.

The dual tips 441, 442 may be arranged on the surgical tool 440 such that the actuation 445 allows an operator to reliably cup the target organ during a procedure (i.e., to substantially minimize movement between the organ and the regions 450*a,b*, 455*a,b*, to control the pressure applied by the regions 450*a,b*, 455*a,b* on the organ, etc.).

The surgical tool 440 may be mechanically and electrically coupled 460 to a controller for purposes of communicating between the monitoring and/or treatment regions 450*a,b*, 455*a,b* on the dual tips 441, 442, controlling the actuation 445 of the dual tips 441, 442, or the like.

Figure 4D:
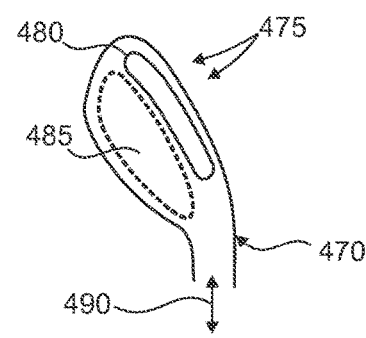

FIG. 4*d* shows a schematic of a side view of a rectally insertable surgical tool 470 in accordance with the present disclosure. The surgical tool 470 may include a dual tip configuration similar to that shown in FIG. 4*c*. The dual tips may be actuated 475 so as to move regions 480, 485 located thereupon towards a target organ. Such movement may include in-plane and out-of-plane movements in order to better interact with the adjacent tissues.

The surgical tool 470 may be mechanically and electrically coupled 490 to a controller for purposes of communicating between the monitoring and/or treatment regions 480, 485 on the dual tips, controlling the actuation 475 of the dual tips, or the like.

In aspects one or more distal tips of a surgical tool in accordance with the present disclosure may include a cooling subsystem, configured to keep the tissues in the immediate vicinity of the electrodes cool during a treatment session (i.e., so as to protect the wall of the rectum during a procedure). In aspects, the distal tip, along a face, or amid elements of an array, there may be arranged one or more temperature sensors, infrared temperature sensors, or the like to indicate local temperature rise during a surgical procedure (e.g., to protect tissues to preserve, to confirm delivery of therapy to target tissues, etc.).

Figure 5A:
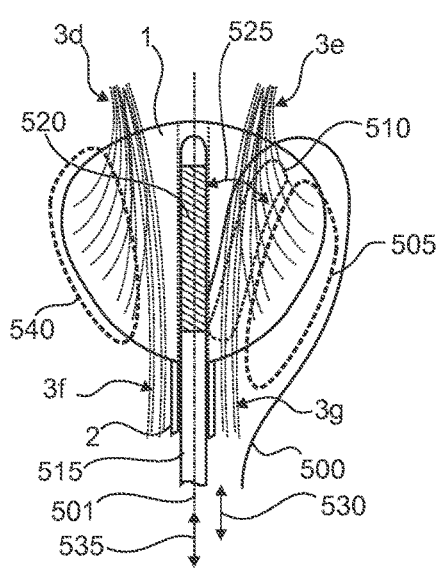
FIGS. 5a-5c show aspects of surgical tools in accordance with the present disclosure.
Figure 5B:
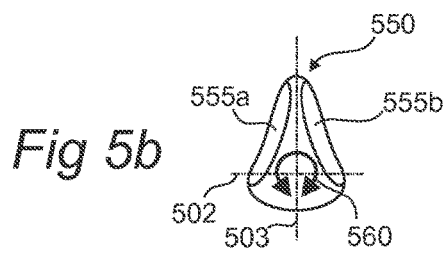
Figure 5C:
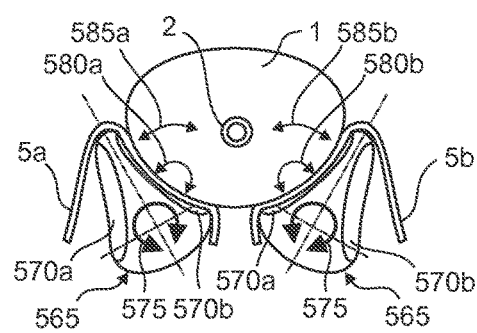

FIGS. 5*a*-5*c* show aspects of surgical tools in accordance with the present disclosure. FIG. 5*a* shows a prostate 1, a urethra 2, and nerves 3*d-g* associated therewith as well as a transurethrally insertable surgical tool 515 and a transrectally insertable surgical tool 500 each in accordance with the present disclosure, interacting therewith. The transrectally insertable surgical tool 500 is placed such that regions 505, 510 on the tool 500 may be biased towards the intended target tissue 540 for treatment, diagnosis, and/or monitoring thereof. The transrectally insertable surgical tool 500 may be coupled with a controller 530, or the like in order to communicate information from the regions 505, 510 to a user, or to communicate energy to the tissue (i.e., via the regions 505, 510). The transurethrally insertable surgical tool 515 may include one or more electrodes 520, imaging elements, energy shaping elements (i.e., so as to assist with the shaping of energy delivered to the target tissues 540 during a procedure, etc.), each in accordance with the present disclosure. The transurethrally insertable surgical tool 515 may be inserted into the urethra 2 along the axis 501 thereof. The transurethrally insertable surgical tool 515 may be coupled 535 to a controller or circuit in accordance with the present disclosure to communicate energy, fluid, etc. to the tissues, or for receiving signals pertaining to a diagnostic, therapeutic, or monitoring procedure performed therewith.

The transurethrally insertable surgical tool 515 may communicate 525 energy, stimulatory signals, etc. through the adjacent tissues of the prostate 1 to the transrectally insertable surgical tool 500 as part of a surgical, monitoring, diagnostic procedure, or the like.

FIG. 5*b* shows aspects of a distal tip 550 of a surgical tool in accordance with the present disclosure. The distal tip 550 includes a plurality of regions 555*a*, 555*b* each including one or more sensors, imaging, and/or energy delivery elements in accordance with the present disclosure. In aspects the regions 555*a*, 555*b* may be configured with concave surfaces as shown so as to better cup a target organ (such as a prostate) during a procedure. The distal tip 550 may be rotatable 560 such that it can interface one or more of the regions 555*a*, 555*b* with the target tissue of an organ during a procedure. For reference, a symmetry line 503 and a construction line 502 are shown, the intersection of which showing a rotational axis about which the distal tip may be rotated 560 to more intimately mate with adjacent tissues during a procedure.

FIG. 5*c* shows a prostate 1, a urethra 2, and a transrectally placed distal tip 565 located within a rectum 5*a*,5*b*, as oriented in two different positions with respect to the prostate 1 in order to monitor, diagnose activity, and/or treat either side thereof. In aspects, the orientation of the distal tip 565 may be changed during a procedure, thus mating one or more regions 570*a,b* with one or more regions of the prostate 1 through a wall of the rectum.

In aspects, the regions 570*a,b* may include one or more energy delivery elements, sensors, etc. for performing the procedure. Depending on the procedure, energy delivery may be performed between one or more portions of a region 570*a,b* and a more distant tissue site 585*a,b* (i.e., thus projecting the energy deeper into the organ), or may deliver energy between elements in the region 570*a,b* to treat a more near-field tissue site 580*a,b* (i.e., thus projecting energy only into the near field tissues of the organ, thus preserving tissues located deeper within the organ).

Rotation 575 of the distal tip 565 may be used to improve the mating between one or more of the regions 570*a,b* and the adjacent tissues, to assist with the imaging, or scanning of tissues, etc.

Figure 6A:
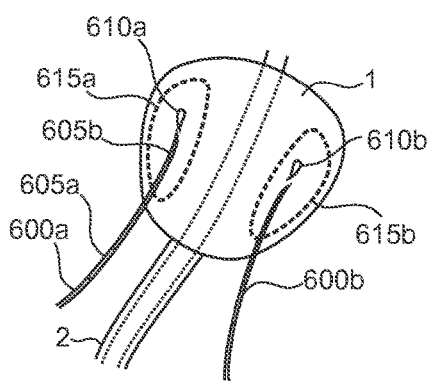
FIGS. 6a-6d show aspects of surgical tools in accordance with the present disclosure.

FIGS. 6*a*-6*d* show aspects of surgical tools in accordance with the present disclosure. FIG. 6*a* shows a prostate 1, a urethra 2, and a plurality of treatment zones 615*a,b* located near the surface of the prostate 1. Multiple probes 600*a*, 600*b* are shown, each in accordance with the present disclosure, having been advanced into the vicinity of the prostate 1 for the purpose of interfacing with tissues therein. A first probe 600*a* is shown with a plurality of electrodes 605*a*, 605*b*, configured for monitoring electrophysiological activity in the vicinity thereof before, during, and/or after a procedure. In aspects, the tip electrode 605*b* may be configured as a microelectrode to monitor electrophysiological activity near to a tip of the probe 600*a*, the larger electrode 605*a* located along the shank of the probe 600*a* may be configured to provide a counter electrode function, a reference electrode function, or the like. In aspects, energy may be delivered in the form of an RF current from the tip electrode 605*b* into the surrounding tissues, perhaps using the larger electrode 605*a* as a return path for the current. In aspects, the probe 600*a* includes a lumen for delivery of a fluid 610*a* in accordance with the present disclosure into the treatment zone 615*a*. FIG. 6*a* also shows a probe 600*b* including a lumen configured to facilitate delivery of a fluid 610b to a treatment zone 615b in accordance with the present disclosure.

In aspects, one or more of the probes 600a, 600b may be transcutaneously inserted into the body in order to access one or more of the treatment zones 615a,b. Alternatively, additionally, or in combination one or more of the probes 600a, 600b may be delivered along an artery or vein in the subject to reach the treatment zones 615a,b.

In aspects, one or more of the probes 600a, 600b may be guided towards a corresponding treatment zone 615a,b through guidance with an imaging system, an ultrasound guided insertion imaging system, or the like.

In aspects, the fluid 610a,b may be a temporary neural blocking agent, a receptor selective neuroblocking and/or neurotoxic agent, etc. In aspects, the fluid 610a,b may be a neural agonistic agent to increase receptor activity at an associated site.

Figure 6B:
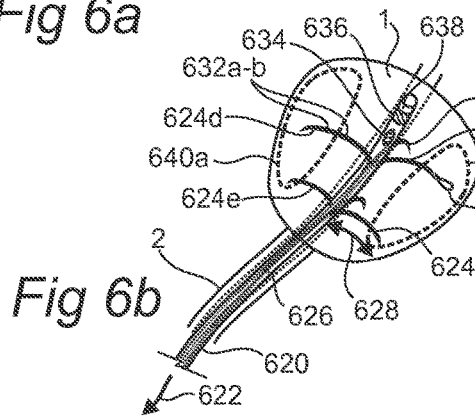

FIG. 6b shows a prostate 1, a urethra 2, and a plurality of treatment zones 640a,b located near the surface of the prostate 1. A transurethrally insertable surgical tool 620 in accordance with the present disclosure is shown placed within the urethra 2 with the distal tip thereof located within the boundaries of the prostate 1. The transurethrally insertable surgical tool 620 may include a plurality of probes 624a-e, deployably coupled to an elongate member 638 of the transurethrally insertable surgical tool 620. The probes 624a-e may be slidingly deployed 628 into the prostate 1 from the elongate member of the transurethrally insertable surgical tool 620 during a deployment procedure. The tips of the probes 624a-e may be inserted into or placed near to one or more intended treatment zones 640a,b. The elongate member 638 may include one or more lumens 626 along which the probes 624a-e may be located within the transurethrally insertable surgical tool 620.

A first probe 624d is shown with a plurality of electrodes 632a,b configured for monitoring electrophysiological activity in the vicinity thereof before, during, and/or after a procedure. In aspects, the electrodes 632a,b may be configured to deliver energy in the form of an RF current into the surrounding tissues, one of the electrodes 632b,a, an electrode 636 on the elongate member 638 or a remotely placed electrode may act as a return path for the current. In aspects, one or more of the probes 624b or the elongate member 638 may include a lumen and/or port 634 for delivery of a fluid 630 in accordance with the present disclosure into the treatment zone 640b.

In aspects, one or more of the probes 624a-e may be guided towards a corresponding treatment zone 640a,b through guidance with an imaging system, an ultrasound guided insertion imaging system, or the like. In aspects, a surgical planning session may be used to determine a distance d through which the probes 624a-e may be deployed 628 during a procedure to best interface with the treatment zones 640a,b. Such a distance may be used when selecting the transurethrally insertable surgical tool 620. Each of the probes 624a-e may be configured with a stop in order to control the distance into the prostate 1 that they may be deployed during a procedure.

In aspects, the fluid 630 may be a temporary neural blocking agent, a receptor selective neuroblocking and/or neurotoxic agent, etc. In aspects, the fluid 630 may be a neural agonistic agent to increase receptor activity at an associated site.

Figure 6C:
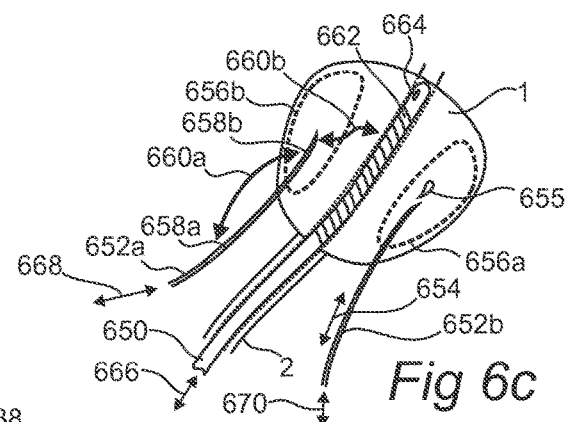

FIG. 6c shows a prostate 1, a urethra 2, and a plurality of treatment zones 656a,b located near the surface of the prostate 1. Multiple probes 652a, 652b are shown along with a transurethrally insertable surgical tool 650, each in accordance with the present disclosure, the probes 652a, 652b having been advanced 654 into the vicinity of the prostate 1 and the transurethrally insertable surgical tool 650 inserted into the urethra 2 and positioned with a corresponding electrode region 662 arranged within the prostate 1 for the purpose of interfacing with tissues therein. A first probe 652a is shown with a plurality of electrodes 658a, 658b, configured for monitoring electrophysiological activity in the vicinity thereof before, during, and/or after a procedure. In aspects, the tip electrode 658b may be configured as a microelectrode to monitor electrophysiological activity near to a tip of the probe 652a, the larger electrode 658a located along the shank of the probe 652a may be configured to provide a counter electrode function, a reference electrode function, or the like. In aspects, energy may be delivered in the form of an RF current 660a,b from the tip electrode 658b, into the surrounding tissues (i.e., into a treatment zone 656b), optionally using the larger electrode 658a as a return path for the current 660a, or using communicating with the transurethrally insertable surgical tool 650 for the return path of the current 660b.

FIG. 6c also shows a probe 652b including a lumen configured to facilitate delivery of a fluid 655 to a treatment zone 656a in accordance with the present disclosure.

In aspects, one or more of the probes 652a, 652b may be transcutaneously inserted into the body in order to access one or more of the treatment zones 656a,b. Alternatively, additionally, or in combination one or more of the probes 652a, 652b may be delivered along an artery or vein in the subject to reach the treatment zones 656a,b.

In aspects, one or more of the probes 652a, 652b may be guided towards a corresponding treatment zone 656a,b through guidance with an imaging system, an ultrasound guided insertion imaging system, communication with the transurethrally insertable surgical tool 650, or the like.

In aspects, the transurethrally insertable surgical tool 650 may include one or more electrodes 662 (optionally for sensing, energy delivery, etc.), or fluid delivery means 664 for purposes of cooling the urethra 2, interfacing with adjacent tissues, etc.

In aspects, the fluid 655 may be a temporary neural blocking agent, a receptor selective neuroblocking and/or neurotoxic agent, etc. In aspects, the fluid 655 may be a neural agonistic agent to increase receptor activity at an associated site.

In aspects, one or more of the probes 652a, 652b, and/or the transurethrally insertable surgical tool 650 may be coupled 668, 666, 670 with a controller in accordance with the present disclosure, to facilitate the interaction with the surrounding tissues, etc.

Figure 6D:
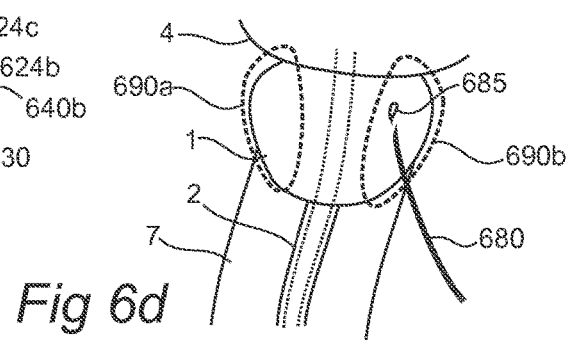

FIG. 6d shows a prostate 1, a urethra 2, a bladder 4, a penis 7, and a plurality of treatment zones 690a,b located near the surface of the prostate 1. A needle probe 680 in accordance with the present disclosure, is shown having been advanced into the vicinity of the prostate 1 via a transcutaneous approach for the purpose of interfacing with tissues therein. The needle probe 680 may include a lumen configured to facilitate delivery of a fluid 685 to a treatment zone 690b in accordance with the present disclosure.

In aspects, the probe 680 may be guided towards a corresponding treatment zone 690b with the assistance of an imaging system, an ultrasound guided insertion imaging system, or the like.

In aspects, the fluid 685 may be a temporary neural blocking agent, a receptor selective neuroblocking and/or neurotoxic agent, etc. In aspects, the fluid 685 may be a neural stimulating agent to increase receptor activity at an associated site.

Figure 7:
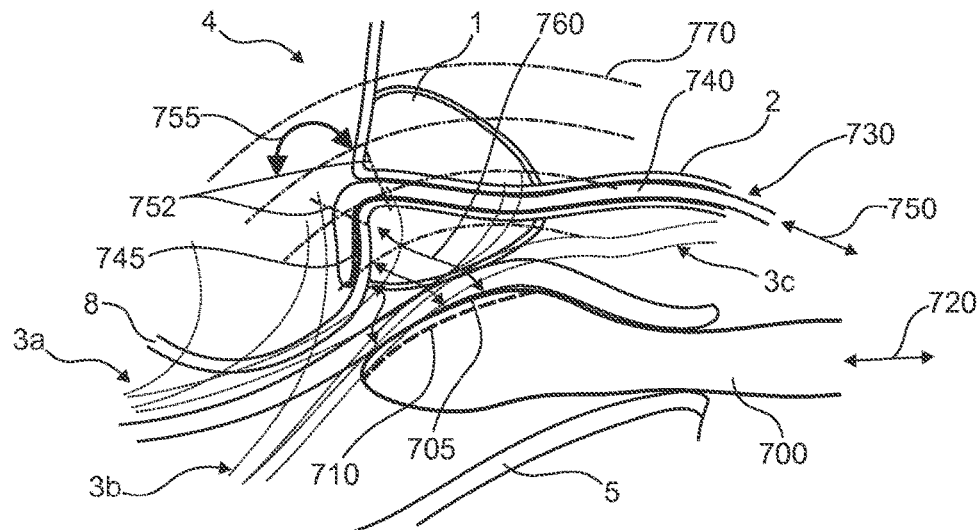
FIG. 7 shows aspects of cooperative transrectal and transurethral surgical tools in accordance with the present disclosure.

FIG. 7 shows aspects of cooperative transrectal and transurethral surgical tools in accordance with the present disclosure. The system includes a transrectally insertable surgical tool 700 sized and shaped so as to be inserted into the rectum 5 of a subject, the transrectally insertable tool 700 including one or more faces 705 arranged along the tip of the transrectally insertable tool 700 such that it may be biased against a wall of the rectum 5 to interface with one or more organs (e.g., prostate 1, urethra 2, bladder 4, bladder wall 8, nerves 3a, 3b, 3c) during a surgical procedure, a diagnostic test, a follow-up procedure, or the like. The face 705 may include one or more electrodes 710 or probes configured for interfacing with tissues in the vicinity thereof during a surgical procedure. The transrectally insertable surgical tool 700 may be coupled to a controller 720 or one or more circuits in accordance with the present disclosure, the controller 720 or circuits coupled to one or more of the electrodes 710, configured to delivery energy to surrounding tissues, monitor electrophysiological activity, provide feedback to an operator, etc. during a surgical procedure.

The system includes a transurethrally insertable surgical tool 730, including an elongate member 740 for coupling and communicating between a distal tip thereof and a controller 750 or circuit each in accordance with the present disclosure. The elongate member 740 includes one or more sensors, electrodes 745, or the like, configured to interface with a surrounding tissue, and/or the transrectally insertable surgical tool 700 during a surgical procedure. The elongate member 740 may include an actuatable region 752 configured such that upon advance of the tip into a bladder 4, the tip may be bent 755 so as to bias the sensors, electrodes 745, or the like against the bladder wall 8 as part of a placement, nerve locating, or monitoring procedure, or the like.

In aspects, the elongate member 740 may include a lumen for providing a fluid, a cooling agent, a medication, a denervating agent, a diagnostic fluid, etc. to the bladder 4 as part of a diagnostic test, a surgical procedure, a monitoring procedure, etc.

In aspects, the face 705 may include one or more probes in accordance with the present disclosure, the probes arranged in a protruding configuration from the face 705, one or more probes configured to bias into, or penetrate through the wall of the rectum 5 during a procedure.

In aspects, the elongate member 740 may include one or more probes in accordance with the present disclosure, slidingly attached thereto, the probes being configured and arranged so as to be deployably inserted into the wall of the bladder, and/or tissues of the prostate 1 during a procedure.

In aspects, the transrectally insertable surgical tool 700 may include one of more imaging elements in accordance with the present disclosure (situated along the face 705), such as an ultrasound transducer. The imaging element may be configured send energy 760 towards or receive energy from the prostate 1, urethra 2, bladder 4, or the nerves 3a, 3b, 3c, so as to image one or more aspects thereof, as part of a procedure.

FIGS. 8a-8d show aspects of methods for treating an organ in accordance with the present disclosure.

Figure 8A:
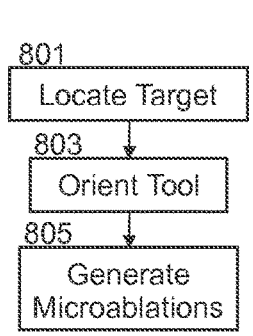
FIGS. 8a-8d show aspects of methods for treating an organ in accordance with the present disclosure.

FIG. 8a shows aspects of a method for treating a target tissue including accessing and locating the target tissue 801, optionally monitoring one or more electrophysiological signals from at least a region of the target tissue and assessing if the ranges are normal or abnormal. If the ranges are normal, accessing an alternative region of the target tissues and monitoring again, or aborting the procedure. The act of accessing alternative regions of the target tissues may include orienting or reorienting the tool 803. Once the correct target tissue has been located, and/or if the electrophysiological activity in the measured tissues is abnormal, the method may include treating the tissue, forming one or more ablations 805 in the vicinity of the tissue (e.g., stimulate, ablate, administer a chemical, etc.), or the like. Optionally, after performing a treatment, the region of the target tissue may be monitored to determine if the electrophysiological activity has changed, is now within a normal range, if a block has occurred, etc. (i.e., determine if there has been a successful outcome for the treatment), or if the signals are still abnormal and require further treatment, alternative treatment, or the like.

In aspects, the method may include reorienting the tool 803 to adjust a contact pressure, adjust an electrode placement against a tissue site (such as along a bowel wall, along an artery coupled to the target organ, etc.), testing another region of the target tissue, treating one or more regions of the target tissue, including one or more steps from a method in accordance with the present disclosure, performing any step of the procedure with a system in accordance with the present disclosure, or the like.

Figure 8B:
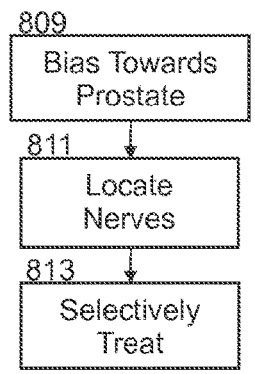

FIG. 8b shows aspects of a method for treating a target tissue including biasing an energy delivery element and/or sensing element towards a prostate 809, locating the nerves to be treated 811 (e.g., the nerves of the prostatic plexus, receptors located on or near the surface of the prostate, etc.), and selectively treating 813 the nerves, receptors, tissues, etc. In aspects, the selectively treating 813 includes sparing nerves that are meant to be preserved during the treatment (such as the pudendal nerves, the dorsal nerves of the penis, etc.). Such selectivity may be provided by one or more sensors in accordance with the present disclosure, one or more imaging elements, a sensation felt by the subject during a stress test, or the like.

In aspects, the method may include accessing the target tissue, and testing at least a region of the accessed tissue with a stimulus in accordance with the present disclosure, while monitoring the response thereof. If the response to the stimulus indicates that the accessed tissue is not the intended target of the therapy (e.g., if the local receptors do not respond to the stimulus, the local receptors respond within a normal range to the stimulus, a sensation is felt in an alternative organ, etc.), the method may include adjusting the access site, so as to interface with an alternative region of the target tissue, and retesting.

Figure 8C:
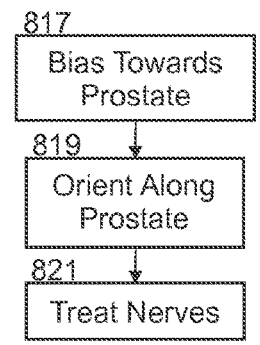

FIG. 8c shows aspects of a method for treating a target tissue including biasing an energy delivery element and/or sensing element towards a prostate 817, orienting 819 one or more aspects of the energy delivery element and/or sensing element along the surface of the prostate, and treating the target nerves 821 identified along the walls and in the vicinity of the prostate.

Figure 8D:
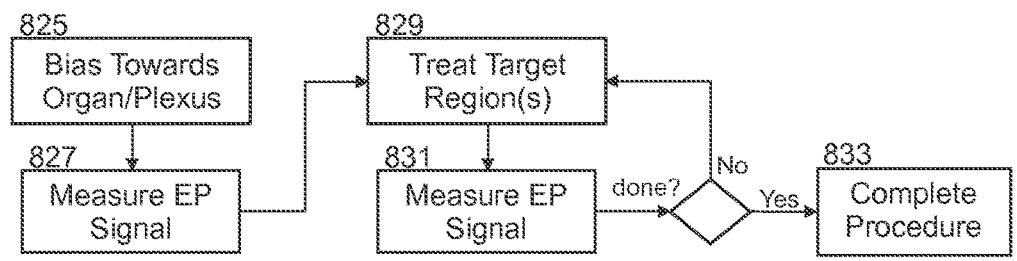

FIG. 8d shows aspects of a method for treating a target tissue including biasing an energy delivery element and/or sensing element towards an organ or neural plexus 825 (i.e., such as from within an adjacent lumen, etc.), measuring one or more electrophysiological (EP) signals 827 associated with the adjacent organ or neural plexus, and at least partially treating 829 the nerves, receptors, tissues, etc. The method may include further measuring and/or monitoring one or more EP signals 831 to determine the extent of the procedure, the state of tissues or nerves surrounding the site that are meant to be spared, etc. and determining if further treatment is necessary, or if the treatment is sufficient. If the treatment is sufficient the method includes completing the procedure 833, withdrawing tools from the body, etc.

In aspects, the further monitoring 831 may include monitoring tissues in the vicinity of the surgical site that are meant to be preserved during the treatment (such as the pudendal nerves, the dorsal nerves of the penis, etc.). Such monitoring may be provided by one or more sensors in accordance with the present disclosure, one or more imaging elements, feedback relating to a sensation felt by the subject during a stress test, or the like.

Figure 9:
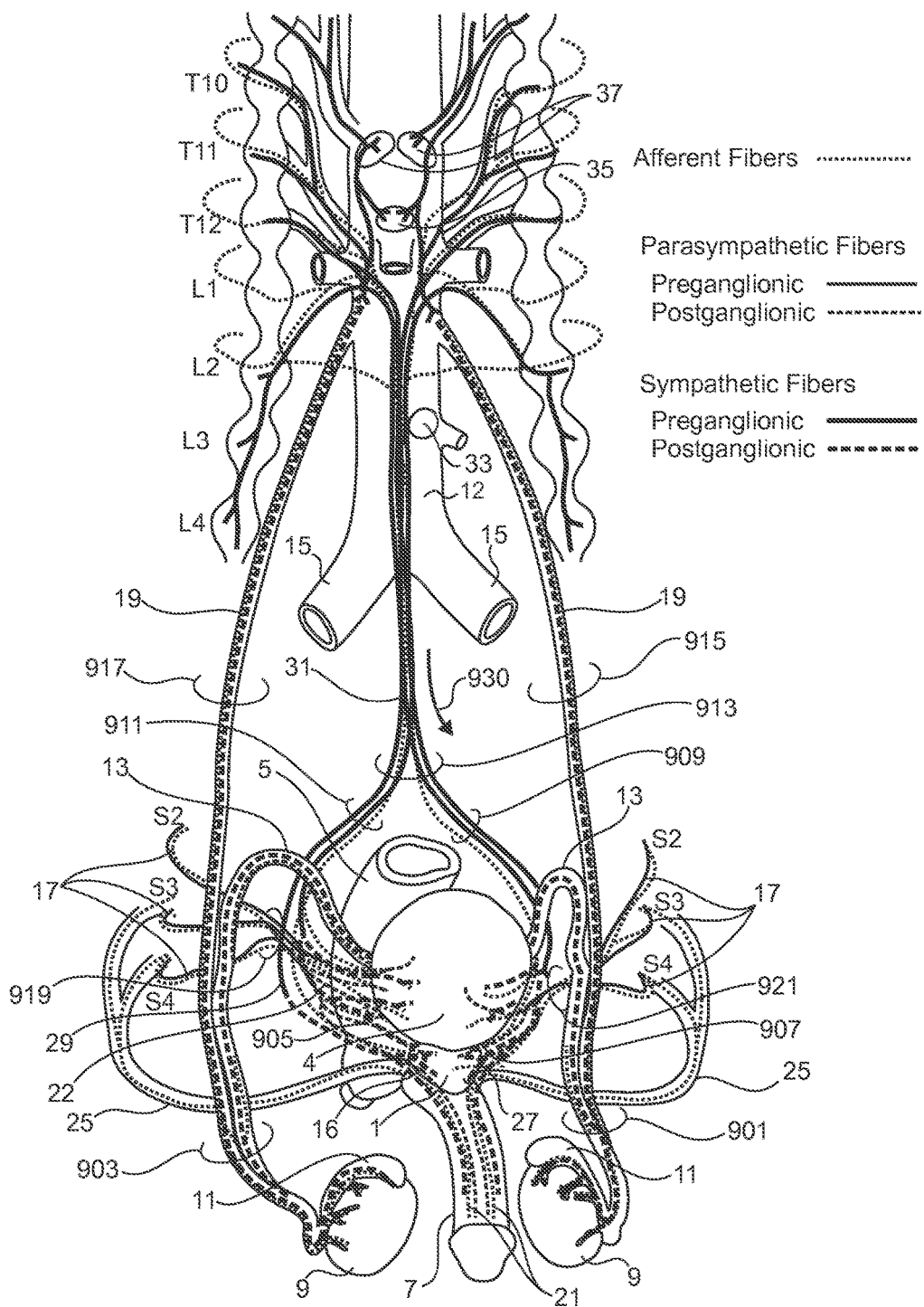
FIG. 9 shows aspects of the nervous system associated with one or more organs of the male LUT and non-limiting examples of treatment sites in accordance with the present disclosure.

FIG. 9 shows aspects of the nervous system associated with one or more organs of the male LUT, surgical access points, and treatment sites associated with methods, uses, and systems of the present disclosure. FIG. 9 highlights aspects of the sympathetic, parasympathetic, and afferent nerve pathways through the lower urinary tract of a human male. A prostate 1, testis 9, penis 7, bladder 4, and rectum 5, are indicated along with coupled arteries and ducts including testicular arteries 19, ductus deferens 13, common iliac arteries 15, abdominal aorta 12, epididymis 11. Not explicitly shown are the prostatic arteries, prostatic venous plexus, inferior vesicle arteries, urethral branches, capsular branches, thereof, and the like. Generally traveling alongside corresponding arteries are nerve plexuses highlighted within FIG. 9. Highlighted nerve plexuses include the prostatic plexus 16, the vesical plexus 22, dorsal nerves 21, splanchnic nerves 17, pudendal nerves 25, cavernous nerves 27, inferior hypogastric plexus 29, superior hypogastric plexus 31, testicular plexus (shown along the testicular artery 19), inferior mesenteric ganglion 33, superior mesenteric ganglion 35, and celiac ganglia 37.

Although any of the plexus, ganglia, receptor sites, or organs themselves, may be considered for treatment, also shown are some specific non-limiting examples of target treatment sites for treating a LUT disease, augmenting organ function, altering hormonal release from an organ, etc. Some non-limiting examples of such target treatment sites 901, 903, 905, 907, 909, 911, 913, 915, 917, 919, 921, include regions situated along or coupled with one or more branches of the prostatic plexus 16, hypogastric nerves 31, testicular plexus 19, inferior hypogastric plexus 29, splanchnic nerves 17, vesical plexus 22, etc.

The sympathetic nervous system is a division of the autonomic nervous system and includes the sympathetic nerve chains and its associated direct and indirect input and output nerve branches, nerve clusters, nerve aggregates, and nerve plexuses located, for example, in the skull, base of the skull, neck, thoracic, abdominal, and pelvic cavities, and their associated arterial and venous structures. The sympathetic nerve chain (also known as the sympathetic nerve trunk) is a long ganglionated nerve strand along each side of the vertebral column that extends from the base of the skull to the coccyx. Each sympathetic nerve chain is connected to each spinal nerve by gray rami and receives fibers from the spinal cord through white rami connecting with the thoracic and upper lumbar spinal nerves. A sympathetic nerve chain has paravertebral ganglia that are connected by a paravertebral sympathetic chain. Target sites in communication with the sympathetic nerve chain, according to the present disclosure, are target sites in the nervous system having fibers that project to and/or from the sympathetic nerve chain and couple with target organs such as the prostate, the testis, etc. Examples of such target sites include the superior cervical, middle cervical, vertebral, inferior cervical and cervicothoracic ganglia, spinal cord segments T1 to L3; sympathetic ganglia (including paravertebral ganglia and prevertebral ganglia), paravertebral sympathetic chain, thoracic and lumbar sympathetic ganglia, nerve plexuses in communication with sympathetic ganglia, dorsal roots, ventral roots, dorsal root ganglia, dorsal rami, ventral rami, white rami communicantes, gray rami communicantes, and recurrent meningeal branches, all emerging from spinal cord segments T1 to L3 (explicitly shown in FIG. 9 are segments T10-L4); T1 to L3 spinal nerves; and any combination of the above from one or both of the sympathetic nerve chains. Thoracic and lumbar ganglia and prevertebral ganglia and their associated sympathetic structures include the cardiac, celiac, mesenteric (superior and inferior), renal, hypogastric, and intermesenteric (abdominal aortic) ganglia as well as ganglia associated with glands such as hepatic or adrenal glands. Nerve plexuses include prevertebral plexuses such as the superior and inferior hypogastric (pelvic) plexus. Target sites also include the thoracic, lumbar, and sacral splanchnic nerves.

The spermatic plexus (or testicular plexus) is derived from the renal plexus, receiving branches from the aortic plexus. It accompanies the internal spermatic artery 19 to the testis.

The prostatic plexus of the male is derived from the larger nerves of the anterior portion of the inferior hypogastric plexus and lies alongside the prostate gland. It supplies the prostate gland, the prostatic urethra and the ejaculatory duct. The prostatic plexus also gives rise to the cavernous nerves of the penis, which are mainly parasympathetic and responsible for relaxation of smooth muscle allowing blood to flow into cavernous spaces in the corpora of the penis resulting in erection. Sympathetic stimulation causes ejaculation and vasoconstriction resulting in remission of an erection. Relating to the treatment of a disease of the prostate, nerves coupled with the prostatic plexus, arranged along a branch thereof, or the like, may be treated in accordance with the present disclosure. Such treatment may result in a decrease of neurotransmitter release within the prostate, a decrease in inflammation within the prostate, may alter the growth-rate of the prostate, may favorably alter the microenvironment of a prostate tumor, or the like.

In aspects, treatment of one or more nerves coupled with the testis may be advantageous to treat one or more diseases associated with hormone imbalance, or the like. In aspects, treatment of at least a portion of the nerves coupled with the testis may be advantageous for altering testosterone production in the testis, decreasing, increasing, testosterone production, etc.

Systems and methods in accordance with the present disclosure may be configured for treating medical conditions that encompass neuromodulation of any combination of one or more target sites of the sympathetic nervous system, including any combination of one or more target sites in communication with the sympathetic nerve chain. The systems and methods in accordance with the present disclosure may encompass ipsilateral, contralateral, and bilateral neuromodulation and/or sympathectomy, partial sympathectomy, and the like.

In aspects, one or more potential treatment sites may be accessed via a minimally invasive procedure in accordance with the present disclosure. A microsurgical tool in accordance with the present disclosure may be routed 930 along an artery associated with a plexus to be treated. The microsurgical tool may be routed along the artery until it can be coupled with the target treatment site associated with the neural plexus associated with the artery. In aspects, the routing 930 of the surgical tool may be assisted with CT, CT-fluoroscopy, etc. Once placed at the target treatment site, the tool may be biased towards the target tissues, interfaced with the target tissues, one or more probes may be deployed, a tip shape may be changed, an ablation balloon may be deployed, etc. and one or more procedures may be performed as part of a treatment, diagnostic test, and/or monitoring session thereupon.

In aspects, a tip of a surgical tool in accordance with the present disclosure may be delivered to a branch of a prostatic artery or prostatic venous plexus (i.e., near to a prostatic plexus) of a prostate. The location of the tip of the tool may be confirmed (e.g., visually, via an associated imaging system, via electrophysiological feedback, through an inter-operative device locating system, etc.) or the like. The tool may engage with tissues in the vicinity of the prostatic artery or venous plexus, and one or more procedures may be performed.

In aspects, a tip of a surgical tool in accordance with the present disclosure may be delivered to a branch of a testicular artery (i.e., near to a testicular plexus) of a testicle. The location of the tip of the tool may be confirmed (e.g., visually, via an associated imaging system, via electrophysiological feedback, through an inter-operative device locating system, etc.) or the like. The tool may engage with tissues in the vicinity of the testicular artery, epididymis, testicle, or coupled anatomical site, and one or more procedures may be performed.

Figure 10:
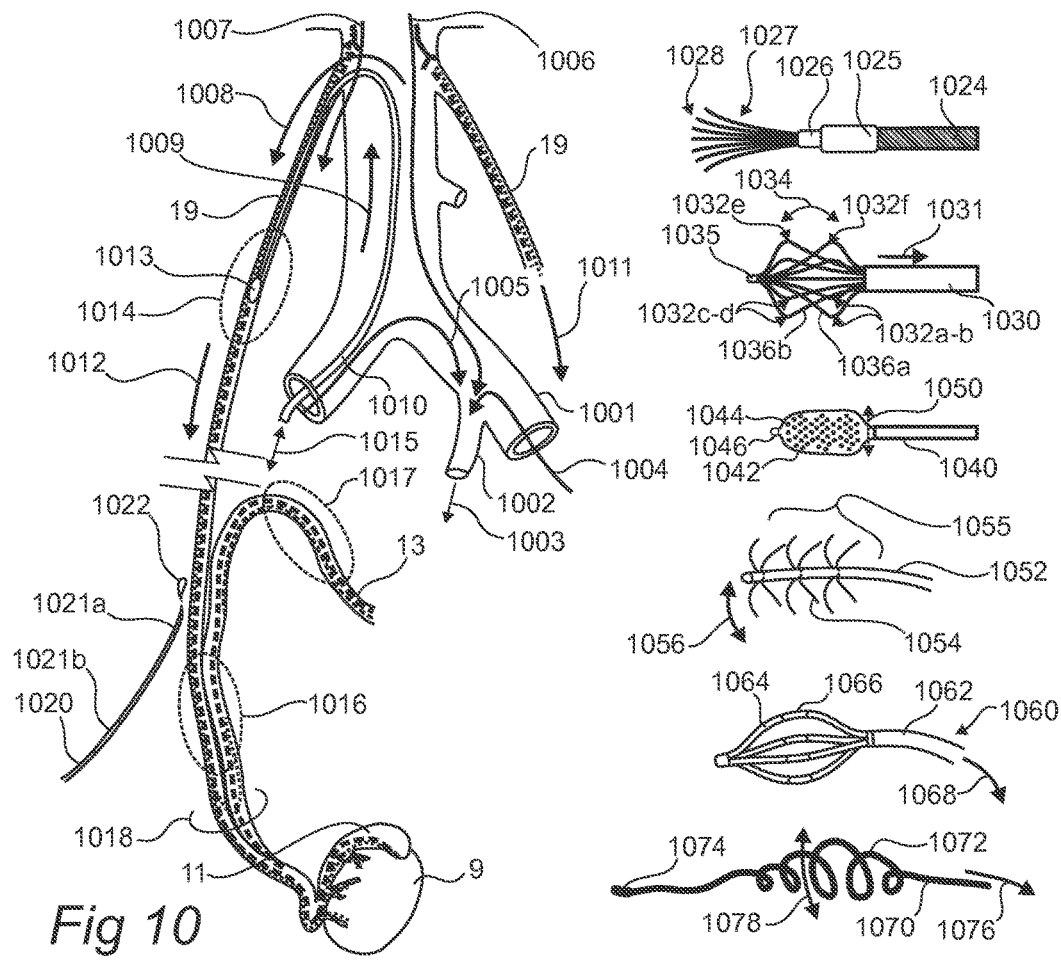
FIG. 10 shows aspects of surgical tools and minimally invasive surgical approaches for treating a testicular plexus and approaches for entering one or more internal iliac arteries in accordance with the present disclosure.

FIG. 10 shows aspects of surgical tools and minimally invasive surgical approaches for treating a testicular plexus and approaches for entering one or more internal iliac arteries 1002 from a common iliac artery 1001 in accordance with the present disclosure.

FIG. 10 includes a schematic of a common iliac artery 1001 and an internal iliac artery 1002 through which a surgical tool in accordance with the present disclosure may be routed 1003 in order to reach the prostatic plexus, hypogastric plexus, etc. Also shown are routes that may be taken to guide a surgical tool into the internal iliac artery 1002, some routes including passage down the abdominal aorta 1006 from a radial artery entry point, passing up 1004, 1005 the common iliac artery 1001 from a femoral artery entry point.

FIG. 10 includes a schematic of a testicular plexus and shows a surgical tool 1010 accessing the testicular artery 19 from a femoral arterial entry point. The surgical tool 1010 was passed up 1009 the abdominal aorta and into 1008 the testicular artery 19. Alternatively the surgical tool 1010 may have entered the body from a radial artery access point and down 1007 the abdominal aorta and into the testicular artery 19. A distal tip 1013 of the surgical tool 1010 is passed down the testicular artery 19 until reaching the target site 1014, 1016, 9, 11, 1018, 1011, 1012. The surgical tool 1010 is shown with the distal tip 1013 in accordance with the present disclosure for interfacing with the adjacent tissues in the target site 1014 or a site related thereto (i.e., a monitoring site, etc.).

The surgical tool 1010 is shown coupled 1015 with a controller (not explicitly shown) for communicating energy, fluid, etc. between the controller and the distal tip 1013, actuating one or more aspects of the surgical tool 1010, deploying one or more probes, etc.

FIG. 10 shows a probe 1020 in accordance with the present disclosure, having been transcutaneously inserted into a body so as to access one or more potential treatment sites. The probe 1020 may include one or more electrodes 1021a,b each in accordance with the present disclosure, and may include one or more lumens to deliver a chemical substance 1022 as part of a treatment, diagnostic, stimulation, ablation, surgical procedure, etc. in accordance with the present disclosure. Some non-limiting examples of target sites 1016, 1017, 13, 9, 11 are shown for treating one or more aspects of the testis, prostate, epididymis, etc.

FIG. 10 shows schematic diagrams for a plurality of distal tips 1013, each in accordance with the present disclosure. A distal tip 1024, including an array of probes 1027, each with an electrode 1028 situated at the tip thereof, is shown, with the array 1027 being confined by a collar 1026, the exposure of which may be used to deploy the array 1027 at a surgical site within a subject. The distal tip 1024 includes a microcircuit 1025 embedded therein and coupled with the electrodes 1028 of the array 1027. The microcircuit 1025 may include one or more preamplifiers for amplifying signals measured at one or more of the electrodes 1028, one or more switches for directing stimulating and/or ablating current flow to one or more of the electrodes 1028, one or more multiplexing circuits, analog to digital converters, digital communication circuits, or the like to communicate between the distal tip 1024 and a controller (not explicitly shown).

A double cage distal tip 1030 is shown including an array of wire probes 1036a-b, each wire probe 1036a-b mechanically bound at a tip 1035. The wire probes 1036a-b may include one or more electrodes 1032a-f, each configured to interface with a wall of a lumen adjacent thereto, for communicating a stimulating or ablating current 1034 there between, for monitoring electrophysiological signals, or the like. The distal tip 1030 may include a sleeve, the retraction 1031 of which may be suitable for deploying the double cage wire probes 1036a-b and interfacing the electrodes 1032a-f with the wall of a lumen into which it has been placed.

FIG. 10 shows a balloon catheter based distal tip 1040 including a balloon 1042 with a plurality of electrodes 1044 or fluid delivery aspects. The balloon 1042 may be deployed 1050 within a lumen in a body in order to bring the electrodes 1044 into intimate contact with a potential treatment site. The balloon tip 1046 of the balloon catheter based distal tip 1040 may be suitable for safely advancing the distal tip 1040 through the lumen without puncturing the wall thereof during deployment to a target treatment site.

FIG. 10 shows a deployable probe based distal tip 1052 including one or more probes 1054 each in accordance with the present disclosure. Collectively the probes 1055 may be deployed 1056 so as to bias against, or penetrate through an adjacent lumen wall during a procedure to access a potential target treatment site.

FIG. 10 shows a single cage distal tip 1060 including a sheath 1062 arranged along the length thereof, retraction 1068 of the sheath 1062 exposing/deploying one or more arms 1064 of a cage, each arm 1064 including one or more sensing elements, electrodes 1066, etc.

FIG. 10 shows a guidewire based distal tip 1070 including a shape changing region 1072 (e.g., a region that may be controllably deployed via an actuation, retraction of a core element 1076, actuation of an electroactive material, etc.), which may transition from a substantially straight shape to a "deployed" shape, suitable for biasing 1078 one or more electrodes, sensing elements, energy delivery elements, or the like against the wall of a lumen into which the guidewire based distal tip 1070 has been placed. The guidewire based distal tip 1070 may include one or more electrodes 1074, sensing elements, etc. for applying energy to a tissue, monitoring the effect thereof, monitoring electrophysiological information in the vicinity of the surgical site, etc.

Figure 11:
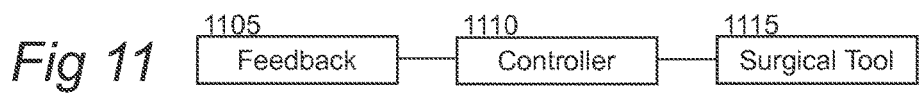
FIG. 11 shows a schematic of aspects of a system in accordance with the present disclosure.

FIG. 11 shows a schematic of aspects of a system in accordance with the present disclosure. The system includes a surgical tool 1115 in accordance with the present disclosure, which may be connected to a controller 1110 in accordance with the present disclosure. The controller 1110 may include one or more signal conditioning circuits, RF generation units, fluid delivery aspects, and/or pulse generators, configured to facilitate one or more methods in accordance with the present disclosure. The controller 1110 may be coupled to a feedback subsystem 1105.

The feedback subsystem 1105 may be configured to display data associated with a surgical procedure, physiological data associated with a monitoring session, graphically display data associated with a mapping process, audibly display data associated with electrophysiological activity, etc.

Figure 12A:
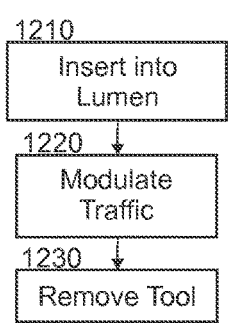
FIGS. 12a, 12b show aspects of methods in accordance with the present disclosure.
Figure 12B:
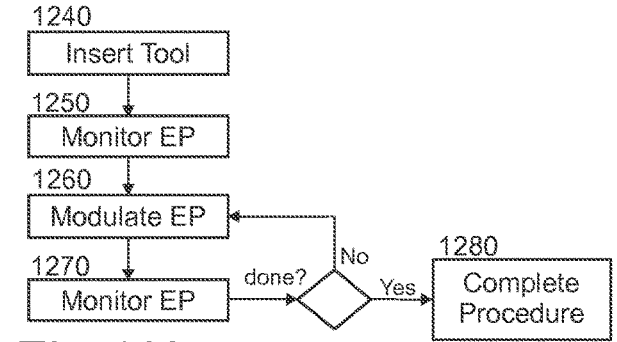

FIGS. 12*a*-12*b* show aspects of methods in accordance with the present disclosure.

FIG. 12*a* shows aspects of a method for treating a target tissue including inserting a surgical tool into a lumen within a body 1210 such as an artery, a vein, a ureter, a duct, or the like, locating and interfacing one or more elements of the tool with the target tissue along the lumen wall or a branch thereof, and optionally monitoring one or more physiological signals from at least a region of the target tissue or site related. The act of accessing the target tissues may include deploying one or more elements of the tool. Once the target tissue has been located and interfaced with, the method may include treating the tissue, forming one or more ablations in the vicinity of the tissue (e.g., stimulate, ablate, administer a chemical, etc.), modulating neural traffic 1220 in the vicinity of the target tissue, or the like, and after completion of the procedure, removing the tool from the body 1230. The act of neuromodulating may include ablating, stimulating, delivering a stimulant or depressant to the target tissues, or the like.

FIG. 12*b* shows aspects of a method for treating a target tissue including inserting a tool into a lumen within the body 1240 and delivering one or more elements of the tool to the target tissue located in the vicinity of the lumen or a branch thereof, measuring and/or monitoring one or more electrophysiological signals 1250 associated with the adjacent organ or neural plexus, target tissue, tissues associated therewith, and modulating 1260 the electrophysiological signals the nerves, receptors, tissues, etc. The method may include further monitoring 1270 to determine the extent of the procedure, the state of tissues or nerves surrounding the site that are meant to be spared, etc. and determining if further treatment is necessary, or if the treatment is sufficient. If the treatment is sufficient the method includes completing the procedure 1280, withdrawing tools from the body, etc.

In aspects, the further monitoring 1270 may include monitoring tissues in the vicinity of the surgical site that are meant to be preserved during the treatment (such as the pudendal nerves, the dorsal nerves of the penis, etc.). Such monitoring may be provided by one or more sensors in accordance with the present disclosure, one or more imaging elements, feedback relating to a sensation felt by the subject during a stress test, or the like.

Figure 13A:
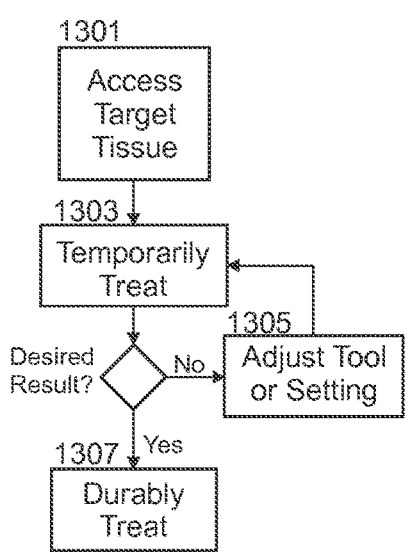
FIGS. 13a, 13b show aspects of methods in accordance with the present disclosure.
Figure 13B:
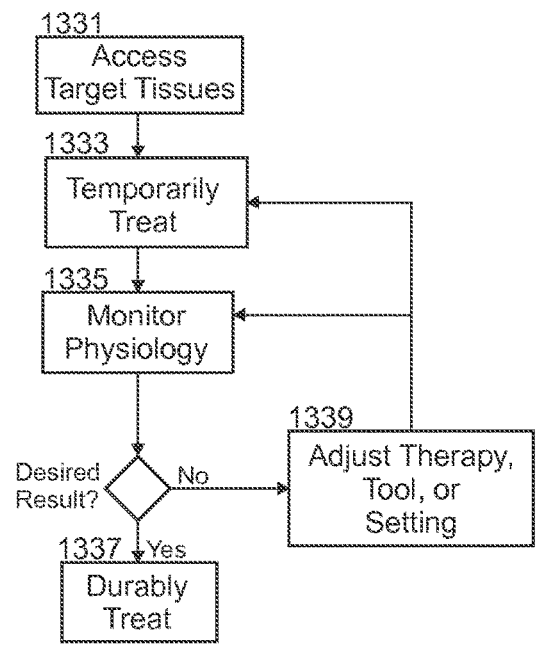

FIGS. 13*a*-13*b* show aspects of methods in accordance with the present disclosure. FIG. 13*a* shows aspects of a method for treating a target tissue including accessing the target tissue 1301, optionally monitoring one or more electrophysiological signals from at least a region of the target tissue, applying a temporary treatment 1303 in the vicinity of the tissue (e.g., stimulate, ablate, administer a chemical, etc.). Determining if the temporary treatment was effective (e.g., by monitoring, evaluating the state of the subject, querying the subject, monitoring nerve traffic, etc.). If the temporary treatment was effective, durably treating 1307 the target tissue. If the temporary treatment was ineffective, the method may include adjusting the positioning and/or setting on the tool and/or the therapy 1305 and applying another temporary treatment 1303 to the target tissue or a site related thereto.

In aspects, the method may include testing another region of the target tissue, treating one or more regions of the target tissue, including one or more steps from a method in accordance with the present disclosure, performing any step of the procedure with a system in accordance with the present disclosure, or the like.

FIG. 13*b* shows aspects of a method for treating a target tissue including accessing the target tissue 1331, optionally monitoring one or more electrophysiological signals from at least a region of the target tissue, applying a temporary treatment 1333 in the vicinity of the tissue (e.g., stimulate, ablate, administer a chemical, etc.). Monitoring one or more physiological signals 1335 from the target site or a site related thereto in accordance with the present disclosure to determine if the treatment was effective (e.g., by monitoring, evaluating the state of the subject, querying the subject, monitoring nerve traffic, etc.). If the temporary treatment was effective, durably treating 1337 the target tissue. If the temporary treatment was ineffective, the method may include adjusting the positioning and/or setting on the tool and/or the therapy 1339 and applying another temporary treatment 1333 to the target tissue or a site related thereto, stimulating, and/or monitoring one or more physiological signals 1335 from the target tissue or a site related thereto, and optionally retrying the treatment.

In aspects, the method may include applying a stimulus to at least a region of the accessed tissue with in accordance with the present disclosure, while monitoring the response thereof. If the response to the stimulus indicates that the accessed tissue is not the intended target of the therapy (e.g., if the local receptors do not respond to the stimulus, the local receptors respond within a normal range to the stimulus, etc.), not responding to the temporary treatment, affecting neural structures that are meant to be preserved, etc. then adjust the location of the therapy, modify the scope of the therapy, etc. so as to interface with an alternative region of the target tissue, and retest. Once a suitable treatment site has been located, continue with treatment in accordance with the present disclosure.

Figure 14A:
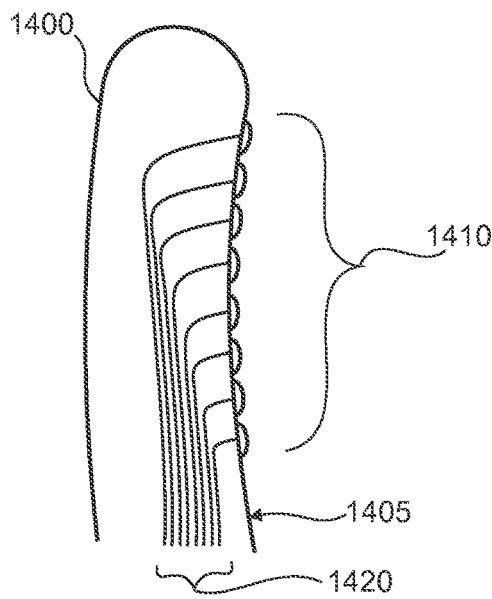
FIGS. 14a, 14b show aspects of a system configured to image electrophysiologically rich target tissues in accordance with the present disclosure.
Figure 14B:
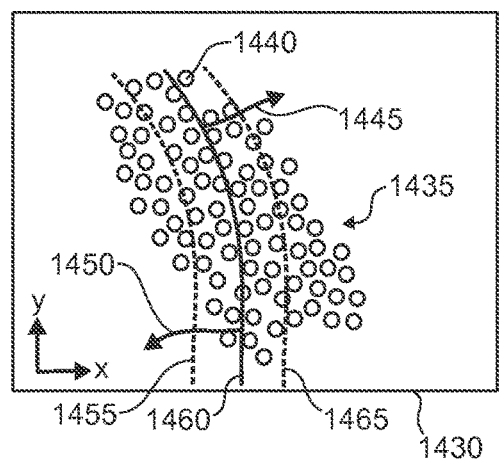

FIGS. 14*a*-14*b* show aspects of a system configured to image electrophysiologically rich target tissues in accordance with the present disclosure. FIG. 14*a* shows a distal tip 1400 of a surgical tool in accordance with the present disclosure. The distal tip 1400 including a face 1405 onto which are coupled a plurality of sensing elements 1410 (such as electrodes) each in accordance with the present disclosure. The sensing elements 1410 coupled 1420 to a controller (not explicitly shown), or microcircuit (optionally embedded into the distal tip 1400 or an elongate member coupled thereto), for conveying information to/from the sensing elements 1410 during a procedure. The sensing elements 1410 may be arranged over the face 1405 so as to form a substantially complete view of an electric field, as applied over the face 1405 of the distal tip 1400 during a procedure.

In aspects, the face 1405 may be biased towards a tissue site (i.e., as sensed through the wall of a rectum, etc.), so as to interface the sensing elements 1410 with the tissues and capture one or more electrophysiological signals associated therewith. In aspects, the feedback may be used to control the bias force of the distal tip 1400 against the adjacent tissues. Such bias force may contribute to an altering of local electrophysiological function. By controlling the force or the effects thereof, a potentially improved image of the local electrophysiological signals may be captured. In aspects, the force may be altered so as to modify a "depth of activity" whereby tissues nearest to the face 1405 may be rendered temporarily inoperative by the force of the bias force, and the measured electrophysiological signals may be characteristic of tissues further way from the face 1405 than otherwise.

FIG. 14*b* shows an image 1430 obtained from a collection of contact points 1440 created by an array of sensing elements 1435 in accordance with the present disclosure in contact with an anatomical site in the body. The image demonstrates propagation of a wave 1460 across the contact points 1440 and illustrates the direction of travel of the wave 1450, 1445 to one or more future sites 1455, 1465. The image and location of the contact points 1440 within the image may be determined from the known positioning of sensing elements on a distal tip in accordance with the present disclosure (e.g., along a face of a distal tip, along a surface of a balloon coupled with a distal tip, etc.). In aspects, the positioning of the sensing elements against the wall may not be known a priori (i.e., in an arrangement with freely moving probes protruding from a distal tip, etc.). In aspects, the positioning of sensing elements within the array may be, at least partially determined from the sensed signals, through correlation of wave propagation throughout the array during a monitoring session. In aspects, a wave propagation algorithm may be used to approximate the positioning of one or more sensing elements against the wall during the monitoring, etc. Other aspects of such configurations are discussed throughout this disclosure.

Figure 15:
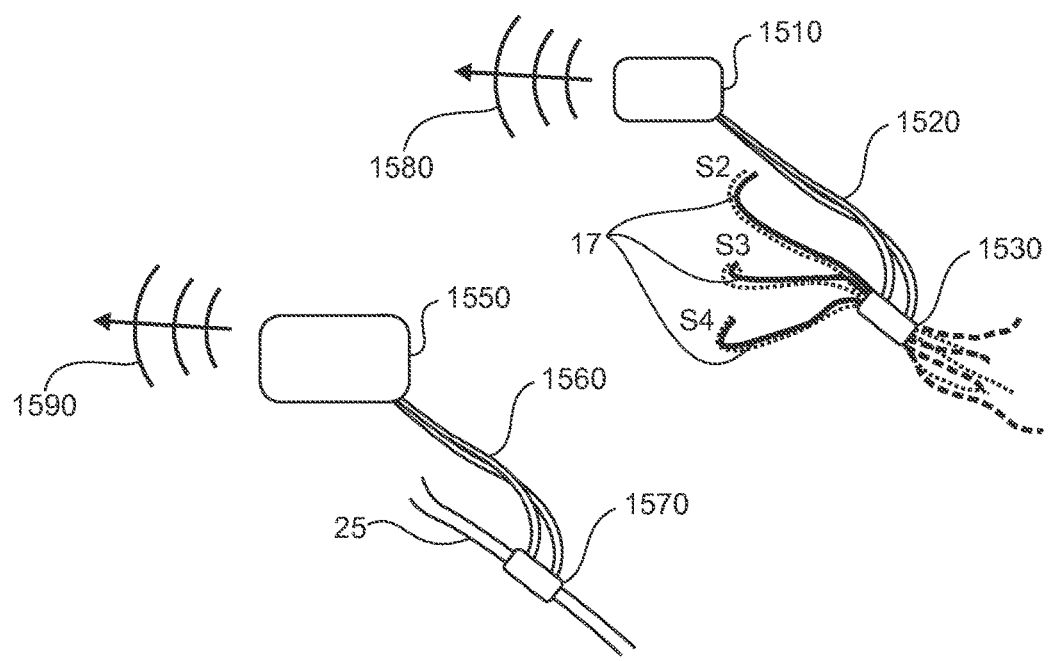
FIG. 15 shows aspects of a stimulator in accordance with the present disclosure.

FIG. 15 shows aspects of a stimulator in accordance with the present disclosure. Aspects relating to two non-limiting examples of stimulators 1510, 1550 are shown. The first stimulator 1510 may include a power source (e.g., such as a battery, an energy harvesting circuit, etc.), a processor, a pulse generator, etc. in order to communicate one or more stimulating pulses via one or more cables 1520, to one or more electrodes 1530 so as to apply a stimulating pulse in accordance with the present disclosure to one or more neural structures in accordance with the present disclosure. The electrodes 1530 shown have been brought into close proximity with a splanchnic nerve 17. The first stimulator 1510 may be configured to monitor one or more electrophysiological signals, so as to record a change in neural activity over time, to adjust a procedure elsewhere in the body, determine a timeframe for a follow up procedure, determine suitability of a subject to respond to a procedure, etc. The first stimulator 1510 optionally includes a radio, RF receiver, or the like to communicate 1580 with a reader for purposes of long term monitoring of a site within the body, etc.

The second stimulator 1550 may include a power source (e.g., such as a battery, an energy harvesting circuit, etc.), a processor, a pulse generator, etc. in order to communicate one or more stimulating pulses via one or more cables 1560, to one or more electrodes 1570 so as to apply a stimulating pulse in accordance with the present disclosure to one or more neural structures in accordance with the present disclosure. The electrodes 1570 shown have been brought into close proximity with a pudendal nerve 25. The second stimulator 1550 may be configured to monitor one or more electrophysiological signals, so as to record a change in neural activity over time, to adjust a procedure elsewhere in the body, determine a timeframe for a follow up procedure, determine suitability of a subject to respond to a procedure, etc. The second stimulator 1550 optionally includes a radio, RF receiver, or the like to communicate 1590 with a reader for purposes of long term monitoring of a site within the body, etc.

Figure 16:
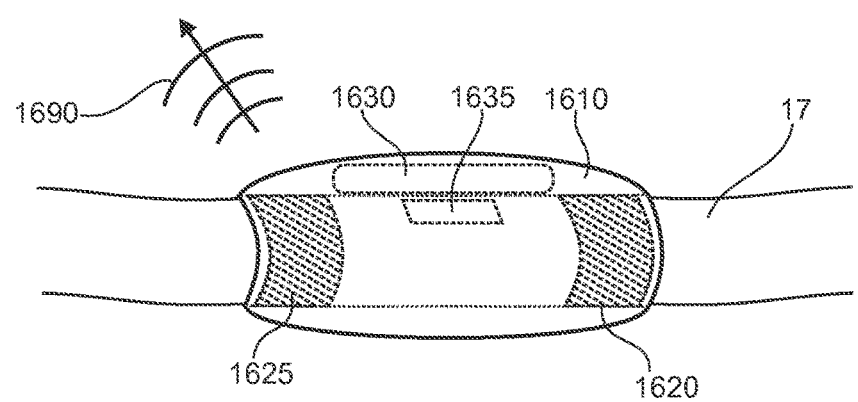
FIG. 16 shows aspects of a clip-based stimulator in accordance with the present disclosure.

FIG. 16 shows aspects of a clip stimulator 1610 in accordance with the present disclosure. The clip stimulator 1610 may include a power source 1630 (e.g., such as a battery, a pin battery, a rechargeable battery, an energy harvesting circuit, etc.), a processor 1635, sensory electronics, a conditioning circuit, a pulse generator, etc. in order to communicate one or more stimulating pulses to one or more electrodes 1620, 1625 in close proximity with a neural structure 17 so as to apply a stimulating pulse in accordance with the present disclosure to one or more neural structures in accordance with the present disclosure. The clip stimulator 1610 may be configured to monitor one or more electrophysiological signals from the electrodes 1620, 1625 or from one or more onboard sensing elements each in accordance with the present disclosure, so as to record a change in neural activity over time, to adjust a procedure elsewhere in the body, determine a timeframe for a follow up procedure, determine suitability of a subject to respond to a procedure, etc. The clip stimulator 1610 optionally includes a radio, RF receiver, or the like to communicate 1690 with a reader for purposes of long term monitoring of a site within the body, etc.

Monitoring may continue during a follow up period immediately after the surgical procedure, and/or during a longer term period (e.g., hours, days, weeks, etc.). Such follow up may be used to determine and/or prognosticate on the longevity of the surgical intervention. Such follow up may be performed with an implantable device such as a clip stimulator 1610 in accordance with the present disclosure. Such monitoring may be used to determine a follow up schedule in accordance with the present disclosure, predict outcome of a subject to a procedure in accordance with the present disclosure, etc.

Figure 17:
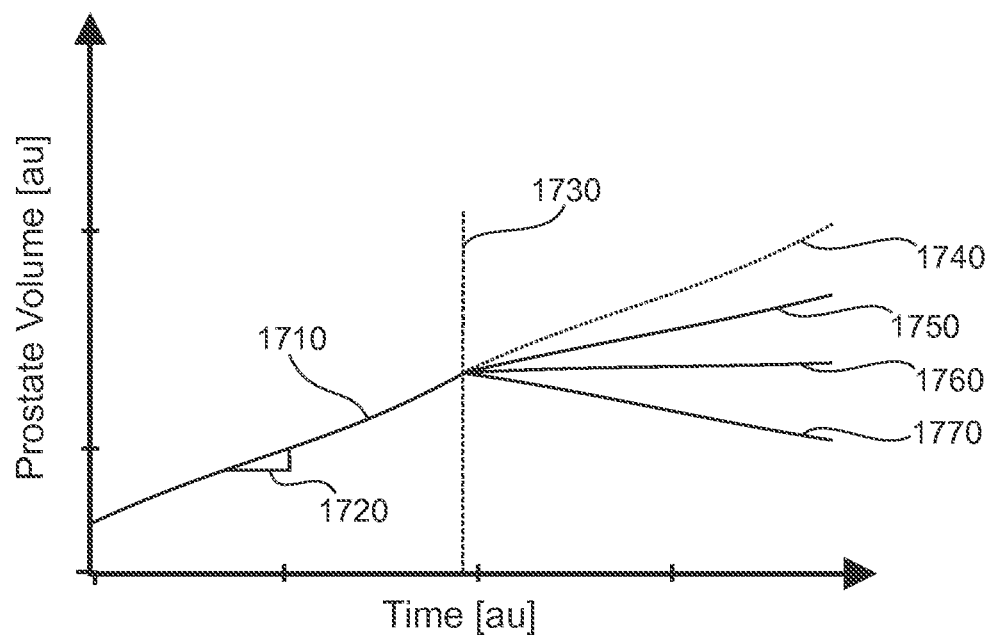
FIG. 17 shows a hypothetical example of a temporal plot highlighting the growth rate of an organ before and after application of a method in accordance with the present disclosure.

FIG. 17 shows a hypothetical example of a temporal plot highlighting the growth rate 1720 of an organ before 1710 and after 1740, 1750, 1760, 1770 application of a method 1730 in accordance with the present disclosure. The temporal plot highlights an initial growth rate 1720 such as a changing volume of a prostate organ indicative of a medical condition, benign prostate hyperplasia, growth of a prostate tumor, etc. A treatment, method, use of a system, surgical tool, or method 1730 in accordance with the present disclosure is performed at a time t and the growth rate, of the organ, tumor, etc. may be altered. Such treatment may be mild 1750, moderate 1760, aggressive 1770, or may include an ablative or stimulative component depending on the particular mode of action initiated by the treatment. In aspects, a partial sympathectomy performed on a neural structure coupled with the prostate may provide similar effect as a parasympathetic stimulation. In aspects, a sympathectomy and parasympathectomy may be favorable to reduce tumor growth, reduce perineural invasion of a tumor into surrounding tissues, etc.

Figure 18:
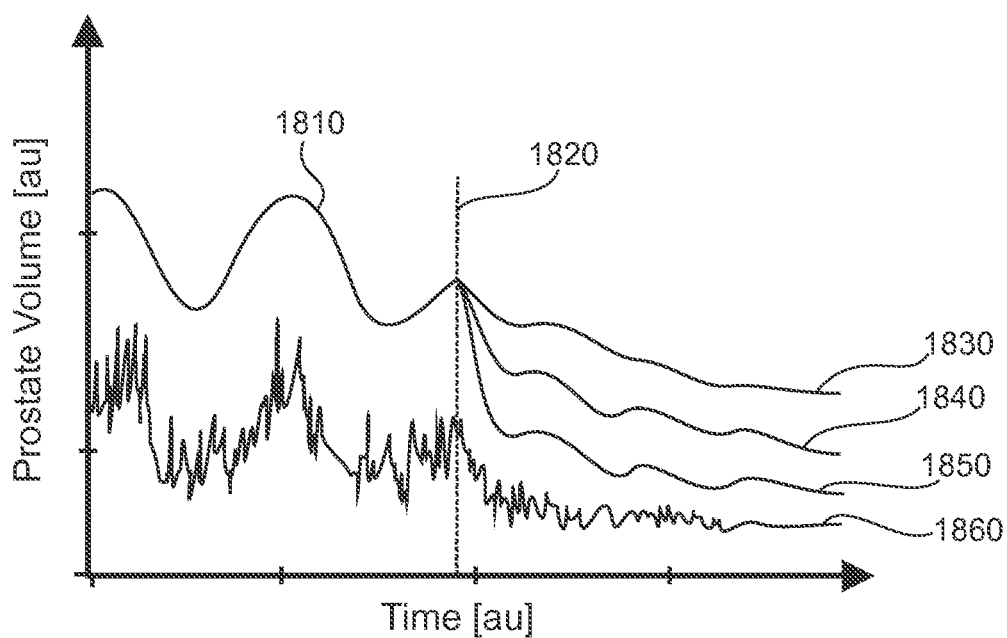
FIG. 18 shows a hypothetical example of a temporal plot highlighting the hormone secretion of an organ before and after application of a method in accordance with the present disclosure.

FIG. 18 shows a hypothetical example of a temporal plot highlighting the hormone secretion from an organ before 1810 and after 1830, 1840, 1850 application 1820 of a method in accordance with the present disclosure. In aspects, the organ may be a testicle and the method may include a neuromodulation procedure, stimulation, prolonged stimulation, or the like applied to a neural structure coupled thereto. FIG. 18 also shows a hypothetical plot of sympathetic neural activity 1860 in a nerve or neural plexus coupled with the organ (i.e., testicle), before and after application 1820 of the method. A mild treatment 1830, moderate treatment 1840, and a comparatively aggressive treatment 1850 are shown. Such treatment is shown as well affecting the sympathetic neural activity 1860, and global treatment of sympathetic neural activity 1860 (such as may be achieved via a neuromodulation procedure, sympathectomy, etc. applied to a carotid body, renal plexus, etc.), may be advantageous in providing similar effects on hormone production or secretion from the organ.

Figure 19:
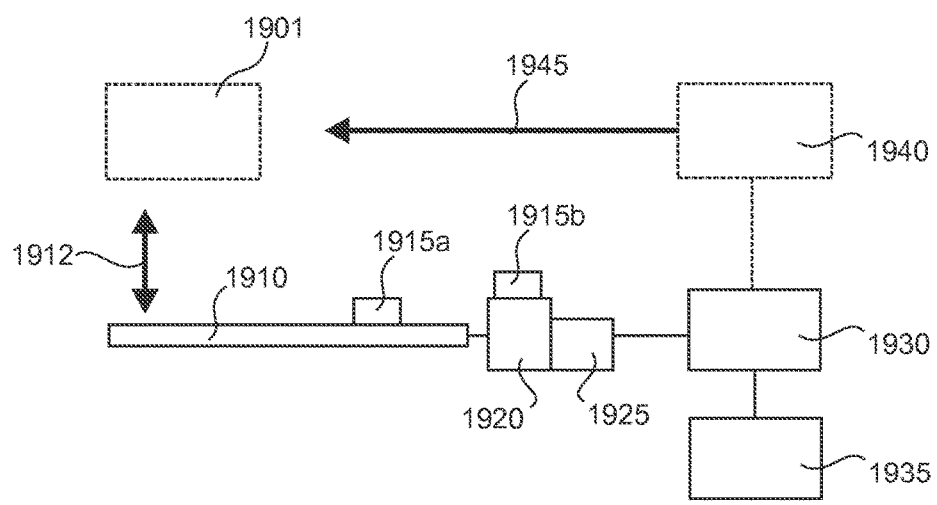
FIG. 19 shows aspects of a system for performing a surgical procedure in accordance with the present disclosure.

FIG. 19 shows aspects of a system for performing a surgical procedure in accordance with the present disclosure. The system is shown interfacing with a surgical site 1901 within a body, a subject, a patient, etc. The system includes a surgical tool 1910 in accordance with the present disclosure. During use, the surgical tool 1910 may be configured to interact 1912 with the surgical site 1901 in accordance with the present disclosure. In aspects, the surgical tool 1910 may be coupled to a connector 1920, the connector providing a mechanical, electrical, and/or optical interface between the surgical tool 1910 and one or more other modules of the system. In aspects, the surgical tool 1910 may include an embedded local microcircuit 1915*a* (a microcircuit, a switch network, a signal conditioning circuit, etc.) in accordance with the present disclosure. In aspects, the connector 1920 may include a local microcircuit 1915*b* in accordance with the present disclosure. In aspects, the connector 1920 may be coupled to an operator input device 1925 (e.g., a foot pedal, an advancing slider, a torqueing mechanism, a recording button, an ablation button, etc.). In aspects, the connector 1920 may be coupled to a control unit 1930 configured to accept one or more signals from the surgical tool 1910, communicate one or more control signals thereto, send one or more pulsatile and/or radio frequency signals to the microcontroller, record one or more electrophysiological signals from the microsurgical tool, or the like.

In aspects, the control unit 1930 may be connected to a display 1935 configured to present one or more aspects of the recorded signals obtained at least in part with the surgical tool 1910 to an operator, to present a map, at least partially dependent on the recorded signals, one or more metrics relating to the monitoring, one or more diagnostic test results, one or more stimulator test results, one or more electrophysiological maps, one or more neural structures to be preserved, etc.

In aspects, the control unit 1930 may be coupled to a surgical subsystem 1940, the surgical subsystem 1940 configured to perform a surgical procedure 1945 to the surgical site 1901. In aspects, the surgical procedure 1945 may be performed via the surgical tool 1910, via an additional surgical tool, etc. Some non-limiting examples of suitable surgical procedures include an ablation, a cryoablation, an excision, a cut, a burn, a radio frequency ablation, radiosurgery, an ultrasonic ablation, an abrasion, a biopsy, and delivery of a substance (e.g., a neuromodulating substance in accordance with the present disclosure). In aspects, the control unit 1930 may be configured to influence, direct, control, and/or provide feedback for one or more aspects of the surgical procedure 1945, based upon one or more of the electrophysiological signals conveyed by the surgical tool 1910.

In aspects, the control unit 1930 may include circuitry for interfacing with an imaging element included in the surgical tool 1910. The control unit 1930 may be configured to alter the surgical procedure 1945 depending on feedback obtained from the imaging element, send mapping, before/after information, physiological information, or the like related to the feedback to the display 1935, or the like.

In aspects, the imaging element may include an ultrasound element, a transducer, a piezoelectric element, an OCT element, a capacitive micromachined ultrasound transducer, a camera, an infrared camera, a near infrared camera, a deep tissue penetrating imaging element, or the like to image the tissues in the vicinity of a probe coupled thereto during a procedure. Such elements may be advantageous for mapping, defining "keepout" zones, or monitoring tissues before, during or after a surgical procedure. Feedback from the elements may be advantageous for determining which nerves to spare and which nerves to treat as part of a procedure.

In aspects, the imaging element may also be suitable for delivering ultrasound energy to one or more of the target tissues/features, as part of a treatment process. In one non-limiting example, the imaging element may be configured to enable dual function imaging and sonication of the prostate from within the urethra, the rectum, the bladder, or between combinations thereof (i.e., an imaging/sonicating probe located in a first orifice and a guiding element, coupled element, etc. located in a second orifice). In aspects, the added mechanical freedom of directing a probe from within the bladder may aid in positioning the distal end of the surgical tool effectively and may reduce the risk of damaging healthy tissue during a procedure.

A surgical procedure in accordance with the present disclosure may include inducing a partial or complete block of a neural signal, and/or receptor, augmentation of the function of a receptor, transmission of a neural signal (i.e., to/from a target organ), a partial and/or substantial neurectomy, peripheral neurectomy, sympathectomy, parasympathectomy, and the like.

In aspects, one or more systems in accordance with the present disclosure may be coupled with one or more imaging modalities including computer assisted imaging computed tomography (CT), magnetic resonance imaging (MRI), positron emission tomography (PET), optical coherence tomography (OCT), magnetoencephalography (MEG), functional MRI, stereotactic surgery, and the like before, during, and/or after a surgical procedure. Such imaging modalities may be used to provide visualization of a target tissue, of inflammation (e.g., inflammation as caused by an associated disease state, as caused by a procedure, etc.), of advancement of one or more aspects of the system towards the target tissue, etc. Use of such imaging modalities may be performed prior to/after surgery and/or intraoperatively.

In aspects, one or more probes and/or energy delivery elements in accordance with the present disclosure may include a fiber optic coupled to a laser (i.e., fiber optic guided radiation to a target tissue), a cryotherapy unit, a heat circulation unit (i.e., a unit for heated wire thermal therapy), an ultrasonic generator, or the like for treatment of target tissue. For purposes of discussion, the majority of non-limiting examples discussed herein are directed to electrical interfacing with tissues, ultrasonic interfacing with tissues, and chemical delivery aspects of such therapies.

A system in accordance with the present disclosure may be configured such that at least a portion thereof may be placed into a lumen (e.g., an artery, a vein, an arteriole, a venule, a duct, a chamber, a pocket, a tubule, a bowel, a urethra, or the like), and/or an organ (e.g., a prostate, a testicle, a kidney, a pancreas, a liver, a lung, or the like) so as to access the neural structure for purposes of diagnosis, and/or treatment of a disease state.

In aspects, the system/surgical tool may include an elongate member and one or more probes (e.g., shanks, needles, microneedles, microneedle electrodes, microneedle fluid delivery catheters, anchors, multi-electrode arms, stabilization arms, combinations thereof, or the like) each in accordance with the present disclosure. One or more of the probes may be coupled to the elongate member. In aspects, at least one probe may be configured so as to slide-ably advance from the elongate member into the wall of a lumen adjacent thereto. The probe may be configured to interface with one or more target tissues in the wall, and/or with a volume of tissue externally positioned with respect to the wall. In aspects, the elongate member may be sized and dimensioned to be delivered via a lumen to the vicinity of a target tissue, the probes may then be advanced therefrom, through the wall of the lumen and into the target tissue in order to monitor, treat, diagnose a condition, or the like.

In aspects, the system may include a plurality of probes, the probes oriented so as to protrude from the elongate member during an actuation (i.e., a deployment or retraction of the probes from the elongate member, such actuation may be automatic, semi-automatic, manual, etc.). Each probe may be configured so as to be advance-able into a lumen wall adjacent thereto during a deployment procedure. One or more probes may be configured to communicate (e.g., fluidically communicate, electrically communicate, optically communicate, etc.) with the target tissues, with another device coupled to the body (e.g., an electrode, a surgical tool in accordance with the present disclosure, etc.), and/or between two or more probes.

In aspects, one or more probes may be arranged so as to be advanced, retracted, twisted, and/or actively bent (e.g., in the case of an active material based probe, a micro-wire actuated probe, etc.) either manually by an operator, or via a robotic actuation (e.g., a mechanism, a servo-controlled mechanism, etc.) during a deployment procedure. Such a configuration may be advantageous for assisting with placement of a probe during a procedure, with aligning a probe with a region of target tissue, advancing the probe through a target tissue, precisely placing one or more regions of the probe within a target tissue, etc.

In aspects, one or more probes may include a microneedle electrode, configured such that at least a portion thereof (e.g., a tip, a shank, a region, a plurality of regions, etc.) may be configured so as to facilitate electrical communication with one or more target tissues adjacent thereto, one or more probes, and/or one or more external electrodes as part of a deployment, monitoring, or treating procedure.

In aspects, a probe may include an array of electrodes, configured so as to assist with determination of a local field gradient, configured so as to monitor a plurality of sites along the length of the probe, to provide a configurable electrode arrangement for sensing, stimulation, ablation, etc.

In aspects, one or more electrodes may be arranged with an active area (i.e., area available to electrically interface with adjacent tissues) of less than 10 mm$^2$, less than 1 mm$^2$, less than 0.1 mm$^2$, less than 10,000 µm$^2$, less than 1,000 µm$^2$, less than 100 µm$^2$, less than 1 µm$^2$, etc. Alternatively, one or more electrodes may be configured so as to form electrical impedance in normal saline of greater than 100 ohm, greater than 1 kohm, greater than 100 kokm, greater than 1 Mohm, greater than 10 Mohm, greater than 50 Mohm, etc.

In aspects, one or more probes may be configured with a characteristic width (i.e., a dimension perpendicular to a length measurement thereof, for example, a diameter), of less than 1 mm, less than 200 µm, less than 100 µm, less than 50 µm, less than 12 µm, less than 3 µm, etc. Such characteristic width may vary along the length of the probe. In aspects, one or more probes may be tapered to a fine tip (e.g., a tip with less than 5 µm radius of curvature, less than 1 µm radius of curvature, etc.) so as to more easily be advanced through tissues during a procedure.

In aspects, one or more regions of a probe or elongate member in accordance with the present disclosure may be coated with a substance and/or treated so as to be lubricious in the presence of water. Some non-limiting examples of such coatings include a hydrophilic coating, a silicone coating, a PTFE coating, parylene, a ceramic, PEBAX, a hydrogel, etc. Some non-limiting examples of such treatments include vapor deposition of a ceramic, a polymer, an ion treatment process, an electroplating process, dip process, etc. Such coating may provide for easier deployment as part of a surgical procedure in accordance with the present disclosure.

In aspects, one or more probes may include a tip fashioned with a tip electrode (e.g., an exposed region of the probe suitable for electrically interfacing with a surrounding tissue, with one or more probes, an external electrode, etc.). In aspects, the tip electrode may be arranged so as to provide a microscopic interface over a length at an end of the probe less than 150 µm, less than 50 µm, less than 20 µm, less than 10 µm, less than 1 µm, and the like. Such a configuration may be suitable for spatially precise monitoring of local field potentials during a procedure (e.g., during monitoring of electrophysiological activity, during a denervation procedure, during placement of the probe, etc.). In aspects, the tip electrode may be arranged so as to provide an intermediately sized interface along the length of the probe, greater than 50 µm but less than 1 mm, greater than 100 µm but less than 500 µm, or the like. Such an arrangement may be suitable for stimulating local tissues, for monitoring overall electrophysiological activity around a volume of tissue, to act as a reference electrode, and the like. In aspects, the tip electrode may be configured along a length of the probe greater than 100 µm, greater than 500 µm, greater than 1 mm, greater than 2 mm, and the like. Such an arrangement may be advantageous for providing a sufficiently high current to surrounding tissues in the vicinity of the electrode, for example, during a hyperpolarizing stimulation, during an ablation procedure, to substantially affect tissues in the vicinity of the tip electrode, and the like.

In aspects an electrode in accordance with the present disclosure may be formed from an electrically and/or ionically conductive material. Some non-limiting examples of electrode materials include gold, platinum, platinum iridium, stainless steel, tungsten, iridium, palladium, rhodium, organic conducting polymer modified materials, poly (acetylene)s, poly(pyrrole)s, poly(thiophene)s, poly(terthiophene)s, poly(aniline)s, poly(fluorine)s, poly(3-alkythiophene)s, polytetrathiafulvalenes, polynapthalenes, poly(p-phenylene sulfide), poy(para-phenylenevinylene)s, poly(3,4-ethylenedioxy thiophene) (PEDOT), poly(3,4-ethylenedioxythiophe)/poly(styrenesulfonate)(PEDOT/PSS), polyfuran, polyindole, polycarbazole, nanorods, nanotubules, carbon nanotubes, carbon fibers, combinations thereof, hybridized composites thereof, and the like. In one non-limiting example, an electrode in accordance with the present disclosure may include a PEDOT film hybridized with gold nanoparticles (e.g., gold particles with diameter less than 20 nm, less than 15 nm, etc.). In aspects, one or more electrodes may include a nanomaterial filler or functionalized material for enhancing one or more properties thereof (e.g., active area, conductivity, etc.).

In aspects, an electrode including an organic conducting polymer or a functionalized organic conducting polymer (e.g., via grafting of specie to the backbone thereof, grafting of an organometallic, biomolecule, etc. thereto, and the like) may be configured so as to monitor a local event associated with tissues in the vicinity of the electrode during use. In such a configuration, the electrical conductivity of the organic conducting polymer in contact with the surrounding tissues may change by orders of magnitude in response to pH, local potential changes, concentration of an analyte (e.g., a neurotransmitter, a neuroblocker, an enzyme, a protein, oxygen, etc.) during use. Such changes may be advantageously monitored during a surgical procedure, so as to assess placement of the probe, determine progress of an associated treatment, or the like.

In aspects, one or more probes/needles may include a fluid delivery channel for delivery of a fluid (e.g., a neurolytic agent, a mild inflammatory agent, a medication, a stimulant, a neuroblocker, a sclerosing alcohol, a neurotransmitter, a chemical denervation agent, a neurodisruptive agent, a sclerosing agent, phenol, alcohol, guanethidine, an antibody drug conjugate, etc.) for delivery to the target tissues. In one non-limiting example, one or more probes may include a microchannel for delivery of fluid. In an aspect associated with a method for treating a target tissue in accordance with the present disclosure, the system may be configured to deliver a bolus of a denervation agent to the target tissues. In aspects, the fluid may be delivered as part of a surgical procedure (e.g., nerve stimulation, denervation, chemical neurolysis, chemical neurolytic blockade, cryoablation, etc.).

In aspects, a system in accordance with the present disclosure may include means for delivering (e.g., channels, a reservoir, a fluid delivery needle, etc.), and/or include one or more quantities of a mixture of lidocaine (1%, 2%, >5%, etc.) with epinephrine (1:1,000,000, 1:100,000, 1:10,000, etc.), and dehydrated ethyl alcohol (2%, 3%, 4%, 5%, 25%, 50%, >50%, etc.) and/or phenol (1%, 2%, 5%, 10%, >10%, etc.) dilute solution for treatment of a volume of target tissues. Additionally, alternatively, or in combination, an amount of bupivacaine (0.1%, 0.25%, 0.5%, >0.5%, etc.), optionally epinephrine (1:200,000) combined with the dehydrated ethyl alcohol and/or phenol may be provided for treatment of a volume of target tissues. Alternatively, additionally, or in combination, the local anesthetic may be administered sequentially prior to injection of the neuroblocking solution.

In aspects, a fast acting and/or fast clearing neuroblocking agent may be injected to reversibly assess a change in local function, to assess if one or more probes are placed in the vicinity of the target tissues, etc. In aspects, a method for treating tissues in accordance with the present disclosure may include injecting a temporary neuroblocking agent into a defined region of a target tissue to assess changes in neural traffic, sensation, etc. and, upon confirmation of the target tissue, dosage, etc. being correct, injecting a bolus of a substantially permanent neuroblocking agent to complete the procedure. In one non-limiting example, a temporary neural blocking agent may be injected into the vicinity of a target neural structure, sensation of the surrounding organs may be confirmed (i.e., via a pinch test or the like), and upon determination that location of the injection will not affect such organs, a substantially permanent neuroblocking agent may be injected into the target tissue.

In aspects, the system may include one or more electrical circuits (e.g., sensing circuits, stimulating circuits, treatment circuits, combinations thereof, etc.) coupled to one or more of the probes and/or electrodes. One or more of the circuits may be configured to deliver a current to one or more of the probes and/or electrodes, between two or more probes, between one or more probes and an electrode (e.g., a patch electrode, an electrode placed elsewhere in/on the body, an electrode attached to another tool within the system, etc.). Alternatively, additionally, or in combination one or more of the circuits may be configured to sense an electrical signal at or between one or more probes, control interconnection of one or more probes and another probe, and/or an electrode, monitor impedance and/or electrochemical impedance spectroscopy, between one or more probes and another probe, and/or an electrode, etc. Impedance changes during a procedure may be used to determine when the procedure is near completion, target temperature levels, as a safety indicator, to determine if the probes are suitably placed against tissues, etc.

In aspects, one or more treatment/combination circuits may be configured to deliver a treatment signal (e.g., a radiofrequency signal, a microwave signal, modulated current, etc.) to/between one or more probes for purposes of ablating the target tissue located in the vicinity thereof. In aspects, one or more of the probes and/or the characteristics of the radiofrequency signal may be configured so as to ablate the target tissue in a substantially predetermined pattern (e.g., a patch-like pattern, patterned array of treatment zones, targeted treatment zones, an elliptical pattern, a longitudinal pattern, a shell-like pattern, a toroidal pattern, etc.). In aspects, the predetermined pattern may be oriented with respect to the wall of the lumen, one or more adjacent anatomical features (e.g., an organ, a tubule, a marker, etc.).

In aspects, a marker in accordance with the present disclosure may include a pretreated tissue, an ablated tissue, a protein marker, a fluorescent marker, a previously placed body (e.g., a placed contrast agent, a placed contrast particle, fluorescent marker, etc.). The marker may be placed as part of a diagnostic test, a preoperative inspection, a surgical procedure, an imaging test, a transplant, during a surgical planning procedure, etc.

In aspects, one or more stimulating circuits may be configured to deliver one or more stimulation signals (e.g., a current pulse, a voltage pulse, a neuro-transmitting agent, a neuro-blocking agent, etc.) to one or more probes for purposes of stimulating one or more aspects of the target tissue (e.g., one or more nerve fibers included in the target tissue and/or adjacent thereto). In the case of delivery of an agent, the stimulating circuit may be coupled to an associated fluid delivery pump, manifold, etc. Such stimulation may be used to communicate with one or more organs within a body, to determine the state of a surgical procedure (i.e., to determine the state of a denervation procedure), to determine the present state of a target tissue (i.e., to determine the health of a target tissue), to treat a disease state in the body (e.g., to modulate sympathetic tone, to interrupt neurological traffic within the vicinity of the target tissues, to modulate an overly active response within an organ, etc.).

In aspects, one or more sensory circuits may be configured to monitor one or more aspects of one or more probes and/or energy delivery elements during a procedure (e.g., during a surgical procedure, a monitoring procedure, etc.). In aspects, one or more sensory circuits may be configured to monitor a current, voltage, impedance, impedance spectrograph (e.g., spectral aspects or distribution of a property, etc.), temperature, etc. between one or more of regions of a probe/electrode, energy delivery element, etc. between two or more of the probes (e.g., between regions of one or more probes, etc.), between a probe, an energy element, and an external electrode (e.g., an externally placed electrode, a reference electrode, an electrode coupled to the elongate member, an electrode placed onto the body, etc.).

In aspects, the sensory circuits may be used to determine if one or more aspects of an energy delivery element have entered into the vicinity of a target tissue (e.g., near to a nerve, a nerve bundle, a muscle, into a region of adipose tissue, penetrated through fascia, penetrated into a second lumen, etc.).

In aspects, one or more of the sensory circuits may be configured so as to monitor one or more energy delivery elements in combination with one or more of the treatment and/or stimulation circuits, which may act upon one or more of the energy delivery elements. In aspects, one or more of the sensory circuits may be configured so as to monitor a surgical process, perhaps at least partially completed by one or more of the treatment and/or stimulation circuits.

In one non-limiting example a sensory circuit in accordance with the present disclosure may be coupled to two or more energy delivery elements within the system. In aspects, a first element may be configured with a reference electrode in accordance with the present disclosure, while one or more of the other probes may be configured with one or more sensing electrodes. The circuit may be configured to obtain one or more differential signals between the reference electrode and one or more sensing electrodes in the system. Such a configuration may be advantageous for mapping, locating target tissues, and/or monitoring electrophysiological activity during a procedure, predicting changes in electrophysiological activity associated with a pending procedure, measuring changes in electrophysiological activity associated with a partial/completed procedure, and the like.

In aspects, one or more sensory circuits may be configured to monitor temporary activity block caused by hyperpolarizing current application and/or thermally significant current applied to one or more electrodes associated with the system (i.e., so as to form a temporary thermally induced block). Such a configuration may be advantageous to determine proper placement of an electrode prior to application of an ablation current, administration of a chemical agent, etc.

In aspects, one or more of the sensory circuits may be configured so as to monitor one or more applications of a fluid (via one or more of the probes) to at least a region of a target tissue. Such an example may be preferable for monitoring the extent of penetration of the fluid into the target tissue, etc. monitoring the interaction of the fluid and the target tissue (e.g., monitoring the state of a denervation process, degree of impedance change in the vicinity of the injection, etc.).

In aspects, one or more of the sensory circuits may be configured so as to monitor the distribution of a fluid into the target tissues. Such a configuration may be advantageous for optimizing the bolus of fluid administered to the target tissues. In one non-limiting example, one or more of the sensory circuits may be configured to monitor impedance between two or more coupled electrodes/probes during a procedure (e.g., a surgical procedure, administration of a bolus of fluid to the target tissue, etc.). Such a configuration may be advantageous to determine and/or control the quantity of a fluid delivered to the target tissues, progression of a surgical procedure (i.e., an ablation procedure), etc.

In aspects, one or more of the stimulation and/or treatment circuits may be configured so as interact with a fluid bolus administered to the target tissues (i.e., by controlling the passage of current there through for example). Such a configuration may be advantageous to further control current flow between one or more probes during a surgical procedure (e.g., during an ablation procedure).

In aspects, one or more of the stimulation and/or treatment circuits may be configured to apply a current pulse and/or a radiofrequency signal between two or more probes, and/or one or more probes and an external electrode (e.g., a patch electrode, an electrode placed elsewhere in the body, etc.).

In aspects, one or more of the circuits may be configured to administer a current pulse and/or radiofrequency signal to one or more regions of the target tissue for a period of 250 seconds, 100 seconds, 10 seconds, 1 second, less than 1 second, etc. via one or more energy delivery elements (e.g., electrodes). In aspects, the current pulse and/or radiofrequency signal may be administered with sufficiently high current, so as to heat one or more regions of the target tissue to a predetermined value within the designated time period. Due to the placement of the probes into the target tissue, a rapid heating pulse may be administered to effectively heat the target tissues to a therapeutic level (e.g., to a temperature above 40 C, above 50 C, above 60 C, above 70 C, etc.). Such heating may be applied with a duty cycle, such that the mean temperature rise in the vicinity of the electrode may be approximately 40 C, 50 C, 60 C, etc. while the transient temperatures and electric fields experienced by adjacent tissues may vary with modulation thereof.

In aspects, one or more circuits may be configured to administer one or more stimulatory pulses to the surrounding tissue during use. Such stimulatory pulses may be configured with amplitude, pulse width, repetition rates, etc. at significant values so as to generate a response in the target tissues without causing substantial damage thereto.

Radiofrequency current may be applied with a frequency of greater than 50 kHz, greater than 500 kHz, greater than 1 MHz, greater than 300 MHz (i.e., into the microwave spectrum), etc. Radiofrequency signals may be modulated with a predetermined and/or variable duty cycle, managed by a user, by an automatic control algorithm, etc.

In aspects, one or more of the circuits may be configured to administer a pulse (e.g., a current controlled pulse, a voltage controlled pulse, a trailing edge pulse, etc.) to one or more regions of the target tissue. In aspects, the circuits may be configured to administer a hyperpolarizing pulse to one or more regions of the target tissue. Such a pulse may be advantageous for suppressing neuronal activity from one or more nerves in the vicinity of the target tissue. Such a configuration may be advantageous for reducing pain associated with the surgical procedure, for determining if an associated probe is located within the target tissue, etc.

In aspects, one or more of the circuits may be configured to administer a hyperpolarizing pulse to one or more probes and sequentially administer a stimulating pulse to one or more of the probes. Such a combination of pulse delivery may be advantageous for suppressing action potentials in a first subset of nerves located in the vicinity of the target tissue, while initiating one or more action potentials in a second subset of nerves located in the vicinity of the target tissue.

In aspects, one or more sensory circuits may be configured to monitor one or more electrophysiological signals (e.g., an extracellular potential, an evoked potential, electromyographic signal, electrocardiographic signal, combinations thereof, or the like), from one or more regions of one or more probes/electrodes as positioned in the vicinity of the target tissue. In aspects, such a configuration may be advantageous for monitoring neural traffic, MSNA in a lumen wall of a vessel in a body, monitor a stimulation provided by one or more probes in the system, etc.

In aspects, one or more sensory circuits may be configured to monitor a plurality of electrophysiological signals. One or more sensory circuits, digital algorithms, signal processing algorithms, or the like may be configured to separate, compare, and/or combine one or more of the electrophysiological signals from a plurality of electrodes or signals generated therefrom. Such a configuration may be advantageous to separate a local neurological signal from a macroscopic electromyographic signal, to map one or more aspects of the target tissue (e.g., determine the location of one or more tissue types within the vicinity of the target tissue, etc.), to monitor progression of a stimulus and/or physiological signal between probe sites in the target tissue, to assess the extent of a surgical procedure, etc. Such information may be advantageous to help target specific sites within the tissue for subsequent treatment.

In aspects, one or more components of a system in accordance with the present disclosure, may be configured so as to be placed within a lumen (e.g., a vessel, an artery, a vein, a chamber, an aneurysm, a rectum, a duct, etc.), for chronic monitoring of one or more electrophysiological signals at a site within and/or adjacent to the wall of the lumen. In aspects, the system may be configured to monitor muscular sympathetic nerve activity (MSNA) in a wall of a lumen, an artery, a vein, a nerve plexus, etc. Related activity may be monitored in the vicinity of one or more sensory afferent nerves, motor efferent nerves, sympathetic, and/or parasympathetic nerves in the vicinity thereof. Thus a correlation between associated nerve traffic may be related to the firing rate of sensory afferents, which may be directly determined from stimulation of receptors, whether in muscles, tendons, or skin. The same may be true for efferent signals travelling to smooth muscle located within a lumen wall.

In aspects, the system may be configured to monitor nerve traffic along a nerve and/or nerve plexus (e.g., part of the sympathetic nervous system, autonomic nervous system, parasympathetic nervous system, celiac plexus, a renal nerve plexus, a carotid plexus, an enteric plexus, a vagus nerve plexus, nerve associated with the LUT, prostatic plexus, testicular plexus, hypogastric plexus, pancreatic plexus, a nerve fiber terminating within the pancreas, and the like), near to a nerve ganglion (e.g., a celiac ganglion, a mesenteric ganglion, lumbosacral plexus, sphenopalatine ganglion, etc.), within a nerve ganglion, near to a receptor, amongst collections thereof, and the like. Such a configuration may be advantageous to monitor electrophysiological activity of a subject as part of a patient selection process (e.g., as part of a patient selection process for an implant, as part of a device function, a pre-surgical procedure, a denervation procedure, etc.), during a surgical procedure (e.g., so as to assess changes in electrophysiological activity associated with one or more aspects of the surgical procedure), as follow-up to a surgical procedure (e.g., as an assessment of the completeness of the surgical procedure, of the durability of the surgical procedure, so as to schedule for a follow-on surgical procedure, etc.).

In aspects, a system in accordance with the present disclosure may be placed for chronic monitoring of electrophysiological activity in the wall of the lumen, within tissue of the organ (e.g., the prostate, the bladder wall, etc.). Such a configuration may be advantageous for monitoring trends in electrophysiological activity (e.g., parasympathetic activity, sympathetic activity, nerve traffic, MSNA, related afferent/efferent traffic, etc.) over a prolonged period of time, and/or within environments unsuitable for acute study (e.g., for a period following a surgical procedure, as part of a long-term follow-up procedure, as part of a clinical study, etc.). Such a configuration may be advantageous in systems for inferring the stress state of a subject, for contribution to a system for managing the stress state of a subject, for feedback into a neuro-activity modulation system, or the like.

In aspects, one or more probes (e.g., flexible elements, needles, or the like) may be oriented into an arch, an anchor, a spiral, etc. so as to provide an interlocking action with the wall of the lumen. Such a configuration may be advantageous for anchoring and/or orienting one or more aspects of one or more probes to the wall of the lumen. Such anchoring may be advantageous for retaining one or more aspects of the system during a procedure, during monitoring, etc. Such anchoring may be advantageous for aligning one or more aspects of the system during a treatment, during a chronic monitoring session, etc.

In aspects, a system in accordance with the present disclosure may be configured and used to alter the sensitivity of one or more regions of an organ in a body to a stimulus. A non-limiting list of organs for which such a procedure may be performed include a gall bladder, a kidney, a small intestine, a stomach, a large intestine, a spleen, a pancreas, a bladder, an adrenal gland, a prostate, a lung, a uterus, or the like. In aspects, such alteration may be achieved through substantially controlled ablation of one or more regions of the organ, one or more sensory nerves, and/or one or more receptors associated therewith coupled with the organ, or the like. In aspects, such a procedure may be completed at least in part with a system in accordance with the present disclosure.

In aspects, a system in accordance with the present disclosure may be used to alter a physiological function within the body. Some non-limiting examples of functions which may be altered by the system include a sensation (e.g., a hunger sensation, an urge to urinate, etc.), a tremor, altering release/secretion of a chemical substance (e.g., one or more acids, neurotransmitters, hormones, toxins, bile, enzymes, surfactants, sebum, renin, etc. from a secretory cell), or the like. Such a system may be used to treat a disease of the LUT, gall bladder, intestines, to augment hunger sensation, reduce sympathetic tone (e.g., overall, and/or related to one or more sympathetic branches, etc.), altering the local concentration and/or release rates of a neurotransmitter, combinations thereof, and the like.

In aspects, one or more elements of a system and/or an elongate member in accordance with the present disclosure may be configured so as to slide over a guidewire with a diameter of less than 2 mm, less than 1 mm, less than 0.5 mm, less than 0.2 mm, less than 0.1 mm, etc. Such a configuration may be advantageous for accessing anatomy within a body via a minimally invasive procedure.

In one non-limiting example, a guidewire may be directed into and down a common iliac artery, a testicular artery, an internal iliac artery, an inferior vesical artery, a prostatic artery, a haemorrhoidal artery, a pudendal artery, minor branches thereof, capsular branches thereof, or the like within a subject. In aspects, the guidewire may include a tip equipped with one or more sensing and/or treatment elements (e.g., ablation electrodes, stimulation electrodes, chemical delivery means, etc.) that is directed along the arteries so as to reach a region of a hyperplastic lobe of the prostate (e.g., a lateral hyperplastic lobe, a middle hyperplastic lobe, etc.), to reach one or more clusters of neural targets near the prostate, or the like as part of a monitoring and/or treatment procedure.

In aspects, a guidewire may be directed into and down a common iliac vein, a hypogastric vein, a dorsal venous complex, obturator vein, a prostatic venous plexus, a vesical venous plexus, so as to reach one or more regions of a hyperplastic lobe of a prostate, to reach one or more clusters of neural targets near to the prostate, etc.

In aspects, one or more elements of the system may then be directed along the guidewire in order to access tissues in the vicinity of the associated lumen into which the guidewire tip has been placed.

In aspects, the guidewire tip may include one or more sensing, energy delivery, and/or chemical delivery elements, so as to provide one or more aspects of a monitoring and/or surgical procedure in accordance with the present disclosure.

In aspects, the guidewire tip may include one or more electrode elements, the electrode elements may be configured to deliver energy into a region of target tissue in the vicinity thereof (e.g., such as a region of tissue on or near a prostate, a length of nerves in the vicinity of the lumen into which the guidewire has been placed, etc.). In aspects, the guidewire may be coated with a substantially non-conducting material (such as PTFE, silicone, polyurethane, PEBAX™, etc.), one or more internal wires of the guidewire exposed near the tip thereof to provide an electrode via which energy may be delivered to a surrounding tissue (e.g., as part of a surgical procedure, etc.). In aspects, the guidewire tip may include a monopolar electrode, and the system may include an additional electrode configured for placement on the skin of, within the urethra of, within the rectum of, the subject so as to provide a counter electrode for the guidewire tip. An RF or MW current passed between the guidewire tip electrode and the additional electrode may be as part of the surgical procedure, etc.

In aspects, the system may include one or more guard electrodes, coupled to the elongate member or a secondary member, coupled with one or more circuits so as to direct a current thereby/through. One or more circuits may be configured so as to communicate/control an electrical signal between one or more of the guard electrodes and one or more of the probes/electrodes. Such communication may be advantageous for controlling an electric field generated thereby, to control current flow through one or more probes/electrodes and one or more guard electrodes, to minimize current flow through tissues adjacent to the guard electrodes, etc.

In aspects, the system may include one or more stabilizing members (e.g., a balloon, an anchor, a curved leg, etc.) coupled to the elongate member, configured to brace and/or position one or more regions of the elongate member near to or against the wall of a lumen during use (e.g., so as to stabilize the elongate member within a rectum, within an artery, etc.). One or more of the stabilizing members may be configured so as to be deployable during use (e.g., so as to move from a first, stored position, to a second deployed position upon actuation).

In aspects, one or more of the stabilizing members may include a balloon, the balloon configured so as to take on a shape when actuated (i.e., when a fluid bolus is delivered into the balloon). The balloon may be configured to brace and/or orient at least a region of the elongate member with respect to the wall of a lumen during a procedure. In aspects, the balloon may be shaped so as to allow for fluid passage thereby even when it is deployed. Some non-limiting shapes (i.e., cross sections oriented along a plane substantially perpendicular to the elongate member) of balloons include a rectangular shape, a ring, a toroid, a gear-like, a flower-like shape, a quatrefoil, an oval, an ellipse, a crescent, a star, a blunted star, a hypocycloid, a hypotrochoid, a rose, a cardiod, a vane, a ribbon, combinations thereof, and the like.

In aspects, one or more of the stabilizing members may include a flexible member, coupled to the elongate member, optionally deployable therefrom during use (e.g., via use of a retractable sheath, by an actuation mechanism in accordance with the present disclosure, etc.). Some non-limiting examples of flexible members include coils, hooks, clips, leaf spring elements, mesh, netting, bistable forms, cantilever beams, and the like. The flexible member may be maintained in close proximity to the elongate member in a stored position (e.g., retractably stored within the elongate member, stored between the elongate member and a sheath, etc.) and configured so as to bias away from the elongate member (i.e., deploy) during use (e.g., through actuation of the flexible member, push actuation of the flexible member, retraction of an associated sheath, sliding of the flexible member along the length of the elongate member, etc.).

In aspects, one or more stabilizing members and/or probes may include an active material element. Control signals delivered to the active material element may help to bias the stabilizing members and/or probes towards the lumen wall, towards the target tissues, actively control the bias force between the stabilizing member and a lumen wall, etc. Some non-limiting examples of active materials that may be suitable for application to one or more probes and/or stabilizing members include shape memory materials (e.g., shape memory alloys, polymers, combination thereof), electroactive polymers (e.g., conjugated polymers, polypyrrole, dielectric elastomers, piezoelectric polymers, electrets, liquid crystals, graft elastomers, polyvinylidene fluoride, combinations thereof, derivatives thereof, etc.), piezoceramics (e.g., amorphous piezoceramics, single crystals, composites, etc.). In addition the active material may be used as a vibratory exciter and/or mechanical probe, for use in monitoring the tone of the adjacent tissues. Alternatively, in addition or in combination, such active materials may be used to cause vibratory/ultrasonic ablation and/or local heating to the tissues during a procedure. In aspects, one or more stabilizing members and/or probes may be configured so as to actuate (e.g., in this case, to change shape, alter a bias force, etc.) so as to bias and/or orient one or more aspects of the system against a wall of an associated lumen (i.e., a lumen into which at least a portion of the system is deployed during a surgery) and/or reorient the component with respect to the target tissue.

In aspects, one or more stabilizing members may be actuate-able so as to cling to the wall of an associated lumen during use. In one non-limiting example, the stabilizing member may be configured so as to close the tip thereof in a pinch-like configuration, as a pincer like configuration, etc. so as to fasten to the wall of an associated lumen during use. In one non-limiting example, a stabilizing member includes a shape memory alloy (e.g., a Nitinol® material) configured so as to undergo shape change when placed inside the body of a subject (i.e., so as to transition between a first shape and a second shape upon increase in temperature due to placement within a warm body). In aspects, a stabilizing member including a shape memory alloy may be configured to change shape (e.g., curl, twist, bend, etc.) upon heating with a control current (i.e., as provided by one or more circuits coupled thereto). Such a configuration may be advantageous for controllably fastening one or more aspects of a system in accordance with the present disclosure to a wall of an associated lumen.

In aspects, one or more probes may include an active material configured so as to assist with orientation during passage into/through the wall of a lumen during surgery. Such a configuration may be advantageous for guiding a probe through the wall of a lumen, towards a target tissue. Additionally, alternatively, or in combination one or more of the probes may include a radiopaque (i.e., radiodense) material (e.g., a titanium, tungsten, zirconium oxide, metal filled polymers, barium sulfate, bismuth compounds, platinum, gold, palladium, combinations thereof, and the like). Such a configuration may be advantageous for visualizing one or more aspects of a probe (e.g., shape, orientation, position with respect to a target tissue, etc.) during a procedure within a body.

In aspects, a system in accordance with the present disclosure may include a plurality of probes, the probes configured so as to protrude at least somewhat radially from an associated elongate member, such that one or more of the probes may bias against and/or penetrate into the wall of an adjacent lumen during use. The system may include one or more circuits configured to interface with one or more of the probes, such that a current (e.g., a radiofrequency current, a modulated current, a microwave current, etc.) may be passed between two or more probes and/or between one or more probes and an additional electrode (i.e., an electrode placed elsewhere on/in the body). Such a configuration may be advantageous for treating regions of target tissue in the vicinity of the lumen. In aspects, current may be passed through two or more probes so as to treat target tissues along the length of the lumen (i.e., in a direction substantially longitudinal to the lumen), along a path substantially circumferential to the lumen (i.e., in a path arching around the center of the lumen), radially out from the lumen (i.e., in a path directed substantially outwardly from the center of the lumen), combinations thereof, or the like. A longitudinal treatment may be advantageous for treating a collection of target tissues (e.g., nerve fibers, etc.) along the length thereof, so as to controllably limit the rate of reinnervation after the procedure.

In aspects, one or more circuits and/or processors included in a system in accordance with the present disclosure may be coupled to a sensory electrode and may be configured to assess functionality of one or more regions of target tissue in the vicinity of the sensory electrode before, during, and/or after a treatment. The circuits and/or processors may be configured to monitor nerve activity in the vicinity of the sensory electrode and to extract/distinguish between changes in such activity before, during, and/or after a process. In aspects, the circuits and/or processors may be configured to extract one or more metrics of signal activity from the monitored signals, some non-limiting examples of such activity include spectral power density thereof, spike count rates, integrated signal strength, and the like. Such metrics may be used to determine the effect of a procedure on the local electrophysiological activity in the vicinity of the sensory electrode, to control a surgical procedure (i.e., the extent of a denervation process), to predict the outcome of a procedure, and the like.

In aspects, one or more probes may be moved (e.g., retracted, nudged, etc.) during a procedure (i.e., during an ablation procedure). Such movement may be used to controllably increase the region of treatment during a procedure.

In aspects, a method for treating a target tissue within a subject in accordance with the present disclosure may include accessing the target tissue with a system in accordance with the present disclosure, monitoring one or more electrophysiological signals in the target tissue to establish one or more characteristics thereof, applying a therapy to the target tissue, and monitoring the electrophysiological signals to assess if there was a change in one or more of the characteristics.

The method may include testing the response of target tissue to a stimulus to determine if the target tissue is that which is intended for treatment, if not, adjusting the placement of one or more probes and repeating the test.

In aspects, a method for treating a target tissue within a subject with a system in accordance with the present disclosure may include inserting an elongate member in accordance with the present disclosure into a lumen adjacent to the target tissue, advancing one or more probes towards the target tissue, and treating the target tissue with one or more of the probes.

In aspects, the method may include placing one or more electrodes onto the body of the subject.

In aspects, the method may include applying a radiofrequency current between one or more probes, and/or a probe and one or more electrodes to treat at least a portion of the target tissue.

In aspects, the method may include advancing a guidewire into the lumen.

In aspects, the method may include altering the shape of one or more of the probes.

In aspects, the method may include monitoring neurological activity of tissues in the vicinity of at least a portion of one or more probes. In aspects, the method may include guiding a probe towards the target tissue using the monitored neurological activity.

In aspects, the method may include monitoring tissue in the vicinity of an electrode coupled to at least one probe to determine the activity thereof.

In aspects, the method may include administering a fluid bolus to one or more regions of the target tissue. In aspects, the method may include monitoring neurological activity in the vicinity of one or more electrodes to determine a change in activity after administration of the bolus.

In aspects, the method may include tracking the position of one or more aspects of a probe with an imaging system such as an MRI, fMRI, PET, CT scanner, with an ultrasonic probe, or the like.

In aspects, the method may include robotically steering one or more of the probes to access the target tissue.

In aspects, the method may include ablating at least a region of the target tissue. In aspects, the method may include monitoring a change in neurological activity after at least a portion of the ablation procedure.

In aspects, the method may include placement of a probe substantially near to a receptor within the target tissue (e.g., within 2 mm, within 1 mm, within 100 um, etc.).

In aspects, the method may include passing a therapeutic current longitudinally along the length of the lumen, radially out from the lumen, and/or circumferentially around the lumen. Such therapeutic current may be passed between one or more probes in accordance with the present disclosure.

In aspects, a system in accordance with the present disclosure may include a probe with a bent and/or twisted tip. Such a probe may be suitable for steerable guidance through a tissue, so as to controllably advance the probe towards the target tissue. The system may include one or more controls (e.g., manual controls, levers, knobs, mechanized/servo controls, actuators, motors, etc.) coupled to the probe so as to enable advancement, retraction, and/or rotation thereof during a procedure in accordance with the present disclosure.

In aspects, one or more probes may be bendable, so as to flexibly access one or more regions of the target tissue during a procedure.

In aspects, a system in accordance with the present disclosure may be used to automatically locate a target tissue and/or electrophysiologically rich region within a body. The system may include one or more elongate members and probes in accordance with the present disclosure. One or more probes may be configured to monitor electrophysiological activity at one or more sites thereupon (i.e., at one or more electrodes). The system may include a processor configured to triangulate signals received from the sites and to determine the location of an electrophysiologically rich region nearest to one or more probes. The system may include a graphical user interface for conveying a guidance signal (i.e., a guidance signal generated from the collection of signals, from a history of collected signals, etc.) to a user. The system may include one or more control circuits configured to actuate one or more probes in response to a user direction (i.e., based on a graphical user interface output determined by the processor), and/or via a robotic control system.

Some non-limiting examples of a guidance signal include an overlay of a target zone, electrophysiological activity, etc. onto a surgical image (e.g., a zone of interest overlaid onto a CT image, MM, Mill, PET, etc.).

In aspects, a system in accordance with the present disclosure may be configured for monitoring one or more tissue regions in a body while applying a stimulus or function altering substance to one or more sites within the body (e.g., a neurotransmitter, neuroblocker, stimulant, a state of hypoxia, a state of hypercapnia, administration of nitric oxide [NO], a local change in blood pressure, a blockage of blood flow, etc.). Such a system may be advantageous for assessing the responsiveness and/or sensitivity of one or more tissue regions to the stimulus or function altering substance.

The system may be configured to treat one or more of the tissue regions, to subsequently apply the stimulus and assess a change in the response thereto.

In aspects, the system may include a plurality of probes in accordance with the present disclosure, more than 3 probes, more than 9 probes, more than 12 probes, etc. In aspects, the system may include a plurality of electrodes in accordance with the present disclosure, more than 2 electrodes, more than 8 electrodes, more than 25 electrodes, more than 100 electrodes, etc. In aspects, a probe in accordance with the present disclosure may include one or more of the electrodes.

In aspects, the system may include a plurality of probes (e.g., 3 or more, 5 or more, 8 or more, etc.), arranged along the elongate member both circumferentially (i.e., around the circumference of the elongate member) as well as along the length thereof (e.g., advancing from the elongate member from one or more regions along the length thereof, a first region near the tip of the elongate member and a second region within 30 mm, within 20 mm, within 10 mm of the first region). In aspects, the probes may be arranged such that deployment thereof outwardly from the elongate member will result in orientation of the elongate member within the lumen (i.e., substantially stabilizing the elongate member within the lumen during deployment). In aspects, the elongate member may include 1 or more deployment regions, each deployment region including 3 or more probes equally spaced around the circumference thereof (e.g., 3 probes 120 deg, 4 probes 90 deg, etc.). Such a configuration may be advantageous to maintain the orientation of the elongate member during a deployment process of the probes into an adjacent lumen wall.

A system/surgical tool in accordance with the present disclosure may be used to access and to treat one or more sensory receptors: Ampullae of Lorenzini (respond to electric field, salinity, temperature, etc.), baroreceptors, chemoreceptors, hydroreceptors, mechanoreceptors, nociceptors, osmoreceptors (osmolarity sensing), photoreceptors, proprioceptors, thermoreceptors, combinations thereof, and the like.

In aspects, a surgical tool in accordance with the present disclosure may include the capability to sense one or more physiological parameters at one or more points around a surgical site, as well as include the capability to stimulate and/or ablate tissues at one or more of the same points and/or an alternative point around a surgical site. The nerve ablation system may be configured so as to access vessels and/or surgical sites in the body. The non-limiting examples disclosed herein may be directed towards such configurations (e.g., so as to controllably ablate renal nerves along a renal artery via an endoscopic procedure, to ablate nerves coupled with a prostate along a prostatic artery, branch thereof, to ablate nerves coupled with a prostate from a transrectally placed probe, to ablate nerves coupled with a prostate from a transcutaneously delivered needle, etc.).

In aspects, one or more electrodes in accordance with the present disclosure may be configured to apply/receive an RF current to/from the surrounding tissue. The RF current may be provided locally between two or more electrodes, or alternatively between one or more electrodes and a macro-electrode placed elsewhere on the body (e.g., on a large skin patch over the surgical site, an electrode placed on another organ, as selected from multiple patches placed over the body, in an associated catheter electrode, etc.). In a non-limiting example where current is restricted to being applied between electrodes, the path for current flow may be well controlled, yet may be highly localized. Alternatively, in an example where RF current is passed between one or more electrodes and one or more macroelectrodes, the current flow may be more challenging to control, but may be used to access tissues more remote from the sensing elements (e.g., farther into the adjacent tissues, deeper into a region of target tissue, from a monopolar guidewire electrode, from a microelectrode configuration, etc.).

In aspects, a system in accordance with the present disclosure may include one or more circuits to simultaneously engage one or more electrodes with the flow of an RF current during an ablation process. In aspects, the local impedance measured between electrodes may be monitored and/or controlled so as to better optimize the current delivered thereto. Additionally, alternatively, or in combination, the local current flow through each electrode may be monitored so as to determine the path of the RF current flow, to ensure no leakage currents are detected, etc. Such information may be used to better control the delivery of RF currents to the target tissues during an ablation procedure.

In aspects, an externally placed (e.g., onto the body of the subject) light source (e.g., infrared, near infrared, visible, etc.) may be directed into the body towards the surgical site, target tissues, and/or lumen. The light source may optionally be modulated to provide a more easily detected signal within the subject. One or more probes may be equipped with optical microsensors which may sense light emitted from the light source. The mapping of received light may be used to locate anatomical features such as nerves near to one or more of the optical microsensor equipped probes during a procedure.

In aspects, one or more externally placed light sources may be used to help locate the anatomical sites of interest during the procedure. An external light source may include a narrow band light source, a broad band light source, light sources spaced apart from each other, and/or combinations thereof. The light sources may be modulated so as to be more easily detectable by sensors located in or near to the anatomy of interest (e.g., lumen, target tissue, etc.). In one non-limiting example, a plurality of light sources may be aimed at the surgical site from distinct vantage points within the body (e.g., as accessed via an endoscopic procedure, etc.) or externally to the body (i.e., as positioned at locations on the body).

Such optical configurations may be advantageous for mapping the local tissues before, during and/or after a surgical procedure. They may also be advantageous for implementation into a nerve detection system (e.g., as input to a nerve hunting algorithm, etc.).

One or more probes may include an electrical shield such that the probe tips may be effectively shielded from other currents flowing through an associated surgical tool (such as a catheter), the body, etc. during a procedure.

One or more probes, and/or elongate members may include a circuit such as a bi-directional switching network, micro amplifier array, etc. in order to amplify sensed signals as close as possible to the anatomical interface, to switch the function of a microfinger tip between sensory, stimulatory, and/or ablation functions, etc.

In aspects, a bidirectional switching network may be used to enable multi-functional stimulation/sense capabilities in one or more probes, etc. The switching network may be included in a local amplifier array, perhaps included in a flexible circuit on one or more probes, attached along the surgical tool (i.e., along an elongate member), as part of the electrical routing along a probe, etc. or alternatively as an extracorporeal element included in a surgical system in accordance with the present disclosure.

A micro amplifier array may be used to preamplify the signals obtained from one or more sensory aspects of the probes and/or probe electrodes, so as to improve the noise signature, etc. during use.

In aspects, one or more probes may be sufficiently hyper elastic (e.g., formed from a memory alloy material, a superelastic material, etc.) so as to effectively deploy from a very small deployment tube and expand outward to larger tissue areas over which to monitor/treat. Such a configuration may be advantageous in so far as a small number of unit sizes may be suitable for treating a wide range of anatomical structures. In addition, the designed curvature and form of a probe may be substantially chosen so as to further enable a wide deployable range of movement during a procedure.

One or more aspects of a probe may be formed from a polymer, a thermoplastic, a polyurethane, a silicone, an elastomer, silk fibroin materials, combinations thereof, or the like. Inclusion of microporous or fibrous substrates, may be advantageous to allow one or more regions of the probe to adhere to the adjacent tissues via capillary effects (i.e., tendencies to wick fluid from adjacent tissues into the substrate). The thickness of films formed from the material may be less than 30 µm thick, less than 20 µm, less than 10 µm, less than 4 µm, less than 1 µm. Composites of somewhat stiffer materials (such as polyimide, PET, PEN, etc.) and somewhat softer materials (e.g., silicones, polyurethanes, thermoplastic elastomers, etc.) may be used to compromise between overall structural stiffness and conformal capabilities.

Patterned overcoats and/or composite layers may also be used to expose electrode materials and/or probe tips to the surrounding tissues in the vicinity of measurement regions, etc.

In one non-limiting example, one or more elements of a probe may be formed from a silk material (e.g., *Bombyx mori* cocoons). The material may be processed to remove sericin (which may cause undesirable immunological response) using methods known in the art. The resulting material can be solvent cast into shapes and crystallized to form self-supporting structures or insulation along a probe, a structural support for a probe, etc.

Alternatively, additionally or in combination the ascribed sensing techniques may be combined with stimulation from local sources. Such stimulation and sensing may be advantageous in determining functionality of local nerves without the need to listen to complex biologically generated nervous activity. Furthermore, combined stimulation and sensing may be advantageous for determining functionality of a local nerve in real-time during a denervation and/or ablation procedure (e.g., the successive stimulation and sensing may be used to determine the degree of neurological block and/or neuromuscular block there between). Such functionality as well as directionality of the nerve signal propagation (e.g., efferent, afferent, etc.) may be more easily determined through use of combined local stimulation and sensing.

Several patterns of nerve stimulation may be used to determine the function of the local nerve structures as well as any associated degree of neurological block and/or neuromuscular block that may be caused by the surgical procedure (e.g., ablation), anesthesia, abrasion, etc.

In aspects, a single stimulation pulse may be applied to one or more electrodes to evoke a response in an associated nerve at frequencies of less than 10 Hz, less than 1 Hz, less than 0.1 Hz. The downstream response as measured by any of the described techniques may depend on the frequency with which the stimuli are applied. In order to allow for complete recovery of the nerve between stimulations (i.e., between pulse trains), a frequency of less than or equal to 0.1 Hz may be advantageous.

In aspects, a probe configured for the delivery of a chemical substance to a target tissue site within the body, may include one or more stimulating electrodes. In aspects, the stimulating electrodes may be employed to stimulate local tissues to test the effect of the delivery of the chemical substance (e.g., via monitoring for the evoked response elsewhere in the vicinity of the body, monitoring for a physiological response to the stimulation before or after administration of the substance, etc.).

During RF ablation of an associated nervous structure, the evoked electrical and/or muscular responses may be dramatically affected. Such changes in the response may be useful in determining the state of the denervation procedure. Thus they may be advantageous to determine the exact degree of RF energy that must be applied to a given structure in order to cause sufficient denervation as desired by a surgical procedure. Such an approach may be advantageous to limit damage to surrounding tissues caused by the denervation procedure, to ensure suitable denervation has been achieved, to determine which nerves are affected by the procedure, etc.

Another technique for stimulation and sensing of the nervous response includes applying a rapid succession of pulses followed by a period of inactivity. Pulse trains may be used to gradually force a nerve into a blocked state. The rate at which a nerve enters a blocked state and later recovers therefrom may be a suitable indicator of the overall health and functionality of the nerve (i.e., may be an advantageous metric for determining how a procedure has affected that nerve).

Note that the sensing of the nervous response may not need to be local to a surgical site and/or target tissues, but in aspects, may be oriented downstream (in the sense of the flow of an associated nervous signal) from the site or in aspects may be a systemic response to the stimulation.

A surgical system in accordance with the present disclosure may include one or more elements to monitor physiological activity and/or analyte levels (e.g., a hormone level), in and/or near to one or more portions of a gland, an endocrine gland (e.g., an adrenal gland, an adrenal medulla, testis, prostate tissue, excretory gland, etc.), or the like.

In aspects, a multi tool surgical system may be employed, each surgical tool in accordance with the present disclosure. In aspects, first tools may be used to probe and/or ablate tissues at a first surgical site (e.g., an artery, an iliac artery, a testicular artery, a urethra/rectum, a renal artery, a left renal artery, etc.) while one or more secondary tools may be configured to monitor one or more physiological parameters elsewhere in the body (e.g., in an alternative artery, a rectum/urethra, a vein, a prostatic venous plexus, within an organ, at a lymph node, at a ganglion, etc.) to determine the effect of the surgical procedure there upon. In one non-limiting example, the tools may be inserted into the same or closely positioned entry points into the body (e.g., a surgical port, etc.). Such a configuration may be advantageous for providing a minimally invasive surgical system to perform the surgical procedure (e.g., a sympathectomy, a renal sympathectomy, etc.) with monitoring performed at multiple, remote locations throughout the body.

Some further aspects relating to systems and methods for adjusting (temporarily and/or permanently) nerve function, while substantially minimizing collateral damage to adjacent structures via endoscopic, transrectal, transurethral, and/or percutaneous tools and methods are now discussed. References made to ablation may be considered to refer to a general surgical procedure (to cut, heat, cool, excise, chemically ablate, etc.) on a tissue.

A method for determining the functionality, directionality, location of and/or the extent of nerve function degradation before, during and/or after a surgical procedure may include stimulating a range of nerves located at a proximal and/or distal location on, within, or coupled to an organ (e.g., a kidney, a renal artery, a gland, a prostate, etc.) in a body; monitoring an evoked response at a location distal and/or proximal to the location of the stimulation; evaluating the signal quality, spectral content, etc. related to the evoked response and/or changes in the evoked response during and/or after the surgical procedure. In general, proximal directions are assumed to refer to an afferent direction (i.e., towards the brain), and distal directions are assume to refer to an efferent direction (i.e., towards the organ).

In aspects, a method in accordance with the present disclosure may include stimulating the stimulation location (e.g., a nerve) with one or more pulse trains, the pulse trains including one or more pulses with a predetermined spectral content (e.g., pulses centered around 10 Hz, 50 Hz, 100 Hz, 500 Hz, etc.) at one or more locations proximal and/or distal to the surgical site.

The pulse train may be applied locally to the nervous structure, with an amplitude of generally 1.5× the voltage required to obtain a maximal amplitude compound action potential (CAP), with pulse duration of generally between 0.05 and 0.5 ms and interval of between 2 ms (for 500 Hz spacing) to 100 ms (for 10 Hz spacing). The pulse train may include one or several such pulses, perhaps even spaced with alternative timing over the application of the pulse (so as to better scan through a frequency range of interest). The corresponding nervous response may be monitored at another location on the vessel or in the body. Such response may be monitored with a gain of generally 500 to 5000 and generally over a frequency band of 0.1 Hz to 10 kHz. This configuration may be used to evaluate the overall health and/or capability of the nervous structure connecting the stimulating location and the monitoring location.

During a surgical procedure, early indication of functional alteration to the nerve structure may be determined by monitoring for a change in the properties of the sensed signal (e.g., a change in latency, amplitude, conduction velocity, spectral content, etc.). In aspects, an ablation pulse may be applied to the nerve between the stimulatory and monitoring locations. A change in the properties of the sensed signal (e.g., a decrease in high frequency content therefrom, a change in latency, change in amplitude, etc.) may be an early indicator that the pulse is being applied properly to the nervous structure there between. In addition, more pulses can be applied and the response monitored in order to observe the nerve response through to a sufficient state of functional alteration, such as during an ablation procedure.

Monitoring may continue during a follow up period immediately after the surgical procedure, and/or during a longer term period (e.g., hours, days, weeks, etc.). Such follow up may be used to determine and/or prognosticate on the longevity of the surgical intervention.

In aspects, the technique may be used to identify the particular neurons of interest to ensure that the correct neurons are being treated surgically (as well as to ensure that the extent of the treatment is acceptable). Such identification may involve monitoring a level of neurological activity on the sensed nerve(s) to determine if the levels are outside of the norm (e.g., as compared with other sites in the body, an activity metric for the patient population or a subset thereof, etc.).

A method for generating a follow up schedule following a surgical procedure may involve monitoring the neurological activity of the site for a period of time (e.g., hours, days, weeks, etc.), at periodic follow up times (e.g., 1 week, 1 month, 6 months, 12 months, etc.) after the surgical procedure; trending the neurological activity to create a metric relating to changes therein over the period of time; and predicting recurrence data (e.g., probability of recurrence, a timeframe of recurrence, etc.) therefrom; and generating a follow up schedule dependent upon the recurrence data.

A method for searching for a nerve of interest on the wall of a lumen may include applying a point pressure on the wall of the lumen while monitoring distal and/or proximal nervous activity (e.g., monitoring, and/or stimulation and sensing on either side of the point pressure probe). Changes in the observed signals may be indicative of pressure induced neural block due to the applied point pressure (i.e., thus identifying the location of the neural anatomy in question).

The method may include clamping the vessel with a flat, smooth backing plate (e.g., a flat soft surface, etc.) and a protruding probe on the adjacent wall, to increase pressure at the interface between the probe and the tissues. The probe may be combined with an ablation electrode (thus providing colocation of the pressure application and the ablation zone). Multiple probes may be used together to deliver ablation along the length of a nerve or nerve bundle. In the case of multiple probes, the probes may be relatively placed onto the surface so as to optimize an ablation current passed there between.

Relating to nerve compression syndrome, acute nerve compression studies have shown some loss of nerve function through application of acute transverse pressure above 40 mmHg, and loss of all nerve function at pressure application above 50 mmHg. Other studies have shown functional block under transverse compression when a pressure of 30 mmHg less than diastolic pressure is applied and 45 mmHg less than the mean arterial blood pressure is applied to the nerve. Thus one or more components of the system (e.g., a clamp, an electrode element, a point pressure applicator, etc.) may provide pressure variation above and/or below these ranges in order to assess nerve function, location, etc. as described herein.

The point pressure applicator may be configured to operatively provide an oscillating pressure to the test site, to synchronize pulsatile pressure application with an array of probes, etc. so as to better orient a pair or array of probes for an ablation procedure.

A surgical tool in accordance with the present disclosure may include one or more whiskers extending from a tool surface so as to reliably contact an adjacent tissue structure during a surgical procedure. The whiskers may include sensing elements such as electrodes, and the like.

Whisker penetration into an adjacent nerve bundle may be used to achieve more intimate contact thereto, as well as to better isolate electrodes from other macroscopic signal interference, etc.

Whiskers may be formed from microfibers, nanofibers, microneedles, nanoneedles, etc. In one aspect, one or more whiskers may be formed from a carbon structure, e.g., a carbon fiber, a carbon nanotube, etc. The whiskers may be insulated along a portion of their length, with an electrically exposed region at the tip there upon.

In aspects, the system may include a feature enhancing medium, to highlight targeted tissue species (e.g., highlight nerve tissues, etc.). The medium may include molecular binding species to selectively bind with surface receptors on the intended target tissue, perhaps changing one or more visual (chromatic) properties in the process and/or including a visual marking moiety. Some non-limiting examples of suitable molecular binding species are peptides and aptamers. Suitable peptides and aptamers may be selected for target tissue (e.g., nerve tissue, fat, etc.) and may be selected as known in the art. In aspects, one or more probes may be configured with a channel for delivery of a binding specie to the target tissue (e.g., via an injection, etc.).

Inclusion of molecular binding species that have been selected for the target cells may be advantageous to assist with anatomical visualization during a surgical procedure. The molecular binding species may be provided, suspended in a delivery vehicle, such that it may be conveniently delivered to the target tissues during a procedure. The delivery vehicle may be a fluid, gel material, a 1 part curing gel, elastomer, etc. that may be conveniently delivered to the target tissues. A fully curable vehicle may be advantageous for providing a simplified method for completely removing the medium from the body after the surgical procedure and/or targeting process has been completed.

Molecular binding species may include a visual marking moiety that is configured to improve visibility thereof. Thus the molecular binding species will bind to the target tissue sites (e.g., nerve tissue, etc.), and will be highlighted by the visual marking moiety for visualization with an appropriate visualization system. Some non-limiting examples of visual marking moieties include: 5-carboxyfluorescein; fluorescein-5-isothiocyanate; 6-carboxyfluorescein; tetramethylrhodamine-6-isothiocyanate; 5-carboxytetramethylrhodamine; 5-carboxy rhodol derivatives; tetramethyl and tetraethyl rhodamine; diphenyldimethyl and diphenyldiethyl rhodamine; dinaphthyl rhodamine; rhodamine 101 sulfonyl chloride; Cy3, Cy3B, Cy3.5, Cy5, Cy5.5, Cy 7, indocyanine green, IR800CW or combinations thereof.

This visualization approach may be advantageous to identify the key tissues for surgical procedures (such as a sympathectomy procedure). By providing the material in a form suitable for surgical delivery and complete removal post operatively (or a safely bioresorbable material), the resulting system may be safer compared to approaches that require systemic application of the material.

The surgical system may include other functionality including: angiographic die delivery, saline delivery, temperature monitoring, intra and extra vascular coordination between devices, through wall imaging, through wall current flow, saline provision for internal arterial, transurethral, or transrectal cooling, and the like.

Some non-limiting methods for performing a surgical procedure in accordance with the present disclosure are discussed herein.

In aspects, a method for addressing a surgical site on an organ in a body (e.g., a bowel wall, a stomach, a kidney, a prostate, a testicle, a gland, an artery, a vein, a renal artery, etc.) is considered. The method includes, monitoring one or more local physiological signals (e.g., an evoked potential, a neurological activity, MSNA, EMG, MMG, sympathetic tonal change, etc.) in accordance with the present disclosure at one or more measurement locations along an outer wall of the organ/lumen to determine one or more reference signals; performing at least a portion of a surgical procedure (e.g., an ablation, an excision, a cut, a burn, an RF ablation, an abrasion, a biopsy, delivery of a substance, etc.) in accordance with the present disclosure at or near to one or more surgical locations (e.g., proximal, distal, remotely therefrom, and/or collocated with one or more of the measurement locations); monitoring one or more local physiological signals at one or more of the measurement locations to determine one or more updated signals; and comparing one or more reference signals with one or more updated signals to determine an extent of completion for the surgical procedure.

In aspects, the extent of completion may include a change, reduction and/or substantial elimination of at least a portion of one or more of the local physiological signals (e.g., reduction in amplitude of a frequency band, reduction in responsiveness, a change in a lag between measurement locations, a change in cross-talk between measurement locations, substantial elimination of the signal, etc.).

The step of monitoring to determine an updated signal may be performed before, during, and/or after the step of performing at least a portion of the surgical procedure.

The step of performing at least a portion of the surgical procedure may be repeated. Thus the method may be incrementally applied, so as to head towards completion in a stepwise process without excessive application of the surgical procedure.

The method may include waiting after performing at least a portion of the surgical procedure. Monitoring may be performed during the waiting procedure, perhaps so as to determine a recovery period for the local physiological signal (i.e., a time period over which the local physiological signal recovers). Such a recovery period may be an indication of the extent of completion.

The method may include stimulating one or more stimulation locations (e.g., proximal, distal, remotely therefrom, and/or collocated with one or more of the measurement locations and/or the surgical locations). The step of stimulating may be coordinated with the step of performing at least a portion of the surgical procedure, and/or with the step of monitoring to determine a reference and/or updated signal. The stimulation may be provided in any form in accordance with the present disclosure. In aspects, the stimulation may include one or more current pulses, one or more voltage pulses, combinations thereof, or the like. The step of stimulation may be advantageous for assessing the updated signal at one or more measurement locations and/or between two or more measurement locations in the presence of background noise and/or local physiological activity.

The method may include monitoring one or more remote physiological parameters in accordance with the present disclosure at a remote location (e.g., an alternative vessel, an organ, a ganglion, a nerve, etc.) substantially removed from the immediate vicinity of the vessel to determine an updated remote physiological signal and/or reference remote physiological signal.

In aspects, some non-limiting examples of remote physiological parameters that may be monitored before, during, and/or after a procedure include water concentration, tone, blood oxygen saturation of local tissues, evoked potential, stimulation/sensing of nervous activity, electromyography, temperature, blood pressure, vasodilation, vessel wall stiffness, muscle sympathetic nerve activity (MSNA), central sympathetic drive (e.g., bursts per minute, bursts per heartbeat, etc.), tissue tone, blood flow (e.g., through an artery, through a renal artery), a blood flow differential signal (e.g., a significantly abnormal and or sudden change in blood flow within a structure of the body, a vessel, an organ, etc.), blood perfusion (e.g., to an organ, an eye, etc.), a blood analyte level (e.g., a hormone concentration, norepinephrine, catecholamine, renine, angiotensin II, an ion concentration, a water level, an oxygen level, testosterone, etc.), a state of inflammation within an organ, a change in growth rate of an organ, nerve traffic (e.g., post ganglionic nerve traffic in the peroneal nerve, celiac ganglion, superior mesenteric ganglion, aorticorenal ganglion, renal ganglion, carotid body, splanchnic nerve, hypogastric nerves, testicular plexus, vesical plexus, prostatic plexus, and/or related nervous system structures), combinations thereof, and the like.

The updated remote physiological signal and/or reference remote physiological signal may be combined and/or compared with one or more reference signals, and/or one or more updated signals in order to determine the extent of completion.

The method may include selecting a surgical location. The step of selection may depend upon one or more monitoring steps, proximity to an alternative surgical location (e.g., a previously treated surgical location, a new location, etc.). The step of selecting may include stimulating local tissues and determining if the stimulation results in excitation of a neural structure, the function of which is to be preserved (such as a pudendal nerve function, etc.), which may be assessed via querying sensation of a subject, etc. and altering the stimulation location until the sensation is no longer felt (i.e., such that the treatment site sufficiently remote from a neural structure that is to be preserved).

In aspects, the steps of monitoring may be completed sequentially. Alternatively, additionally, or in combination, the steps of monitoring may be effectively continuously applied through the procedure. The comparison may be made using one or more data points obtained from one or more steps of monitoring. The comparison may be made via algorithmic combination of one or more measurements, a time averaged comparison, a convolution, or the like. Such an approach may be advantageous for initially inducing a temporary functional change in the target tissues, and if deemed successful, progressing to a substantially permanent functional change in the target tissues.

In aspects, the method may include forming a topographical map from the one or more measurements (e.g., from one or more of the signals). The method may include determining a topographical map of physiological functionality in the vicinity of the surgical site derived from one or more of the physiological signals. The method may include updating the topographical map after the step of performing at least a portion of the surgical procedure.

In aspects, the method may include placement of a plurality of surgical tools, one or more surgical tools (i.e., a procedural tool) placed so as to access one or more of the surgical locations, and one or more surgical tools (i.e., a monitoring tool) placed so as to access one or more of the monitoring locations. In one non-limiting example, a procedural tool may be placed upon/near to a first organ (e.g., a bowel wall, a stomach wall, a kidney, a gland, a pancreas, a neural body, a carotid body, a renal artery, a left renal artery, etc.) and a monitoring tool may be placed upon/near to a second organ (e.g., an opposing renal artery, a neural body, a gland, a carotid body, a pancreas, a right renal artery, a femoral artery, an iliac artery, etc.). Thus, the monitoring tool may be used to monitor one or more of the measurement locations on the second organ. The procedural tool may be used to surgically treat one or more surgical locations on the first organ. Additionally, alternatively, or in combination, the procedural tool may monitor one or more monitoring locations on the first organ, perhaps in combination with monitoring performed on the second organ by the monitoring tool.

In aspects, the method may be performed with one or more surgical tools in accordance with the present disclosure.

One or more steps of monitoring may be performed with one or more probes and/or electrodes in accordance with the present disclosure.

One or more steps of performing at least a portion of the surgical procedure may be performed with one or more probes and/or electrodes in accordance with the present disclosure.

In aspects of a method for RF ablating tissue, the local tissue tone may be measured before, during, between individual RF pulses, and/or after a train of RF pulses. In aspects, as the local tissue tone changes during application of the RF pulses, the tonal changes may be used to determine the extent of the therapy. In aspects, as the RF ablation process is applied to the adjacent tissues (perhaps via one or more sensing elements), the tonal measurements (as determined by one or more sensing elements, perhaps the same tip through which the RF signal may be applied) may be monitored to determine an extent of completion of the procedure. Such an approach may be advantageous for performing such a procedure as the tonal measurement techniques may not be significantly affected by the local RF currents associated with the RF ablation procedure. The tonal measurements may be made at monitoring locations sufficiently far from the RF ablation zone such that the local tissues under measurement are not directly affected by the RF ablation process but may undergo a change in tone as a consequence of the RF ablation process.

According aspects there is provided, a system including an elongate member with a proximal end and a distal end, at least a portion of which is configured for placement within a body, the elongate member including one or more energy delivery elements arranged upon and/or coupled near to the distal end, arranged so as to direct energy therefrom (e.g., radially, circumferentially, axially, combinations thereof, or the like) during a surgical procedure. One or more of the energy delivery elements may include an electrode, a needle, a fluid delivery aspect (for delivery of a chemical agent), an ultrasonic transducer, a microwave antenna, combinations thereof, or the like.

In aspects, the system may be configured for placement into the rectum of the body, for entry into the vasculature of the body (e.g., an artery, a vein, etc.), for entry into a urethra of the body, combinations thereof, or the like.

In aspects, the system may include and/or couple to one or more imaging elements, configured so as to image one or more surgical sites, organs, and/or tissue regions in the body. In aspects, one or more imaging elements may be incorporated into the distal end of the surgical tool, configured so as to image tissues, organs, and the like in the vicinity of the distal end.

In aspects, the system may include an array of electrodes, arranged along a face of the distal end, so as to butt against an organ, when the distal end is biased there against. The array may be configured such that energy may be selectively delivered to adjacent tissues via one or more electrodes in the array (e.g., via one or more electrodes, to one or more electrodes, from one or more electrodes, between one or more electrodes, etc.).

In aspects, the imaging system may be used to locate one or more target features on an organ including a nerve, a plexus, a lymph node, a vesicle, or the like. In aspects, the imaging system may be coupled to a display system configured to display positional information relating to one or more of the target features. The system may include a processor and/or control system configured to direct energy through one or more of the energy delivery elements so as to treat the target tissue.

In aspects, the system may include an elongate member coupled with one or more probes (e.g., shanks, needles, microneedles, microneedle electrodes, microneedle fluid delivery catheters, anchors, multi-electrode arms, stabilization arms, combinations thereof, or the like) each in accordance with the present disclosure. In aspects, at least one probe may be configured so as to slide-ably advance from the elongate member into the wall of a lumen adjacent thereto (e.g., for progression towards an adjacent organ, etc.). The probe may be configured to interface with one or more target tissues in the wall, and/or with a volume of tissue exterior to the wall.

In aspects, one or more components of a system in accordance with the present disclosure, may be configured so as to be placed within a lumen (e.g., a vessel, an artery, a vein, a bowel, a rectum, a chamber, an aneurysm, etc.), for monitoring of one or more electrophysiological signals within and/or adjacent to the wall of the lumen (e.g., as part of a diagnostic procedure, a surgical procedure, a prolonged or chronic monitoring procedure, or the like). In aspects, the system may be configured to monitor muscular sympathetic nerve activity (MSNA) in a wall of a lumen, an artery, a vein, a nerve plexus, etc. In aspects, the system may be configured to monitor nerve traffic along a nerve and/or nerve plexus (e.g., part of a the sympathetic nervous system, autonomic nervous system, parasympathetic nervous system, celiac plexus, a renal nerve plexus, a carotid plexus, an enteric plexus, a vagus nerve plexus, pancreatic plexus, a nerve fiber terminating within the pancreas, and the like), near to a nerve ganglion (e.g., a celiac ganglion, a mesenteric ganglion, lumbosacral plexus, sphenopalatine ganglion, etc.), within a nerve ganglion, near to a receptor, amongst collections thereof, or the like. Such a configuration may be advantageous to monitor electrophysiological activity of a subject as part of a patient selection process (e.g., as part of a patient selection process for an implant, as part of a device function, a pre-surgical procedure, a denervation procedure, etc.), during a surgical procedure (e.g., so as to assess changes in electrophysiological activity associated with one or more aspects of the surgical procedure), as follow-up to a surgical procedure (e.g., as an assessment of the completeness of the surgical procedure, of the durability of the surgical procedure, so as to schedule for a follow-on surgical procedure, etc.).

In aspects, the system may be placed for prolonged or chronic monitoring of electrophysiological activity in the wall of the lumen. Such a configuration may be advantageous for monitoring trends in electrophysiological activity (e.g., parasympathetic activity, sympathetic activity, nerve traffic, MSNA, etc.) over a prolonged period of time (e.g., greater than 1 day, greater than 1 week, greater than 1 month, or the like). Such a configuration may be advantageous for inferring the stress state of a subject, for contribution to a system for managing the stress state of a subject, for feedback into a neuro-activity modulation system, or the like.

According to aspects there is provided use of a system or method each in accordance with the present disclosure to alter the sensitivity of an organ in a body to a stimulus, and/or alter the growth rate and/or development of an organ. A non-limiting list of organs include a gall bladder, a kidney, a small intestine, a stomach, a large intestine, a spleen, a pancreas, a bladder, an adrenal gland, a prostate, a lung, a uterus, a testicle, and the like. In aspects, such alteration may be achieved through a substantially controlled/monitored ablation of one or more regions of the organ, one or more sensory nerves, receptors associated therewith, or the like.

According to aspects there is provided use of a system or method each in accordance with the present disclosure to alter a function within the body. Some non-limiting examples of functions which may be altered by the system include a sensation (e.g., a hunger sensation, an urge to urinate, etc.), alter the state of inflammation of the organ (i.e., alter the microenvironment within an organ), a tremor, altering release/secretion of a chemical substance (e.g., acid, hormones, toxins, bile, enzymes, surfactants, sebum, renin, etc. from a secretory cell), or the like. Such a system may be used to treat a disease and/or functional state of a gall bladder, prostate, testicle (i.e., to modulate the secretion of androgens therefrom), intestines, to augment hunger sensation, reduce tone, combinations thereof, and the like.

According to aspects there is provided, use of a system or method in accordance with the present disclosure to treat a tumor (e.g., a tumor associated with prostate cancer, etc.). Such use may involve altering the neural traffic coupled with the tumor, down regulating neural activity in the vicinity of the tumor, destroying nerves coupled to the tumor (i.e., nerves which, when left untreated, may facilitate migration of cancerous tissue via perineural invasion to other regions of the body). Not wishing to be bound by theory, use of such systems and methods in this manner may be advantageous for minimizing pathways for tumor cell migration, down-regulation of signaling, and/or chemical release by receptors in the vicinity of the tumor (which, left untreated, may aid in the growth of the tumor, provide the tumor with a favorable microenvironment in which to grow, provide signaling cues directing cell growth and migration, etc.).

In aspects, a system or method in accordance with the present disclosure may be used to enhance chemotherapy, reduce pain associated with a cancerous tumor, reduce pain due to an associated cancer treatment, etc.

According to aspects there is provided, a method for treating a tumor within a body including altering neural traffic along one or more nerves coupled to the tumor and/or nerves in the vicinity of a microenvironment of the tumor.

In aspects, the method may include monitoring neural traffic before and after the step of altering neural traffic, in order to assess the procedure, predict an outcome therefrom, adjust the energy provided by the treatment, etc.

In aspects, the method may include accessing the nerves with a system or device in accordance with the present disclosure, and treating the nerves with the system, or the device, or a method in accordance with the present disclosure.

In aspects, the method may include minimizing and/or assessing a feeling of pain associated with the tumor or an associated cancer treatment.

According to aspects there is provided, a method for treating a target tissue within a subject including accessing the target tissue with a system in accordance with the present disclosure, monitoring one or more electrophysiological signals in the target tissue or a site coupled thereto to establish one or more characteristics thereof, applying a therapy to the target tissue or neural site coupled thereto, and monitoring the electrophysiological signals to assess if there was a change in one or more of the characteristics.

The method may include testing the response of target tissue to a stimulus to determine if the target tissue is that which is intended for treatment, if not, adjusting the placement of one or more probes, and/or energy delivery elements and repeating the test.

According to aspects there is provided, a method for treating a target tissue within a subject with a system in accordance with the present disclosure including inserting an elongate member in accordance with the present disclosure into a lumen adjacent to the target tissue, advancing one or more probes and/or energy delivery elements towards the target tissue, and treating the target tissue with one or more of the probes and/or energy delivery elements.

In aspects, the method may include placing one or more electrodes onto the body of the subject.

In aspects, the method may include applying a current, a microwave frequency current, a radiofrequency current, an electroporation pulse, or the like between one or more probes and/or energy delivery elements, and/or a probe and/or energy delivery element and one or more electrodes to treat at least a portion of the target tissue.

In aspects, the method may include administering a chemical agent to at least a portion of the target tissue (e.g., to a region of an organ, a region of a prostate, a nerve plexus, etc.).

According to aspects there is provided, a system in accordance with the present disclosure for locating target tissues and/or electrophysiologically rich regions within a body including one or more elongate members, energy delivery elements, imaging elements, and/or probes each in accordance with the present disclosure. One or more probes, energy delivery elements, imaging elements, or the like may be configured to monitor electrophysiological activity, and/or associated anatomical features (e.g., nerves, ganglia, nerve plexuses, etc.) in the vicinity thereof (e.g., at one or more electrodes, within the field of view of the imaging element, etc.). The system may include a processor configured to interpret signals received from the sites and to determine the location of an electrophysiologically rich region nearest to one or more probes and/or elements. The system may include a graphical user interface for conveying a guidance signal (e.g., a guidance signal generated from the collection of signals, from a history of collected signals, etc.) to a user. The system may include one or more control circuits configured to actuate one or more probes, elongate members, etc. in response to a user direction (i.e., based on a graphical user interface output determined by the processor), and/or via a robotic control system.

In aspects, a guidance signal may be an overlay of a target zone, electrophysiological activity, etc. onto a surgical image (e.g., a zone of interest overlaid onto a CT image, an ultrasound image, MRI, fMRI, PET, etc.).

According to aspects there is provided a system in accordance with the present disclosure for monitoring one or more tissue regions in a body while applying a stimulus to one or more sites within the body (e.g., a neurotransmitter, neuroblocker, stimulant, a state of hypoxia, a state of hypercapnia, administration of NO, a local change in blood pressure, a blockage of blood flow, etc.). Such a system may be advantageous for assessing the responsiveness and/or sensitivity of one or more tissue regions to the stimulus.

The system may be configured to treat one or more of the tissue regions, to subsequently apply the stimulus and assess a change in the response thereto.

According to aspects there is provided, a method for altering the growth rate of an organ, including denervating and/or altering (e.g., increasing, decreasing, oscillating, etc.) the functionality of one or more neurons and/or neurological structures (e.g a nerve plexus, a ganglion, etc.) coupled to the organ or a hormone releasing organ associated therewith.

In aspects, the organ may be a prostate gland, a testicle, an ovary, an organ of the lower urinary tract, or the like.

In aspects, one or more of the neurons may belong to a corresponding sympathetic or parasympathetic nervous system, or afferent nerves associated with the organ.

In aspects, the step of denervating and/or altering the functionality may be accomplished via a surgical procedure (e.g., a denervation procedure, a partial denervation procedure, an ablation, an ultrasonic ablation, a chemical denervation, a radiological denervation, a dissection, a thermal treatment, a mechanical disruption, combinations thereof, or the like).

In aspects, the method may include one or more of insertion of a surgical tool in accordance with the present disclosure into the rectum of a subject, insertion of a surgical tool in accordance with the present disclosure into the urethra of a subject, biasing the surgical tool towards the organ, scanning the surface of the organ to locate one or more target tissues/features (e.g., nodules, nerves, lymph nodes, or the like) thereupon, the directing energy towards one or more of the target tissues/features, locating one or more of the nerves, marking one or more of the target tissues/features, monitoring one or more of the target tissues/features, displaying and/or mapping one or more of the target tissues/features, combinations thereof, and the like.

In aspects, the method may include insertion of a surgical tool in accordance with the present disclosure transcutaneously into the tissues surrounding the organ.

In aspects, the method may include insertion of a surgical tool in accordance with the present disclosure transurethrally so as to position it against the organ.

In aspects, the method may include directing energy between a first surgical tool and a second surgical tool each in accordance with the present disclosure, the first surgical tool having been positioned within the urethra and the second surgical tool having been positioned within the rectum of the subject.

In aspects, the method may include mapping and/or imaging one or more regions of the organ, so as to locate and/or identify one or more of the target tissues/features. The step of mapping and/or imaging may be accomplished using ultrasound (transcutaneous, transrectal, transurethral, etc.), radiological imaging, magnetic resonant imaging, PET imaging, electrophysiological mapping, combinations thereof, or the like, etc.

In aspects, the method may include monitoring electrophysiological activity in, on, or near to the organ, and/or one or more nerves coupled thereto. The step of monitoring electrophysiological activity may be accomplished with one or more surgical tools in accordance with the present disclosure.

In aspects, the step of monitoring may include, monitoring one or more electrophysiological signals in a tissue included in and/or coupled to the organ to establish one or more characteristics thereof, applying a therapy to the organ and/or tissue coupled thereto, and monitoring the electrophysiological signals again to assess if there was a change in one or more of the characteristics. The step of monitoring may include performing the treatment until the electrophysiological signals have been altered so as to reach a predetermined level (e.g., reduced to a predetermined activity level, reduced by a percentage of an initially measured activity level, etc.).

The method may include testing the response of target tissue to a stimulus to determine if the target tissue is that which is intended for treatment, if not, adjusting the placement of one or more probes and repeating the test.

In aspects, a method in accordance with the present disclosure may be used so as to prevent, slow, and/or alter the onset and/or progression of LUTS, BPH, ED, CP, HG, nocturia, PrCa, combinations thereof, and the like.

According to aspects there is provided, a method for altering the growth rate of an organ including stimulating one or more nerves coupled thereto. In aspects, the organ may be an organ of the LUT, a prostate, a testicle, or the like and one or more nerves may be a pudendal nerve, a parasympathetic nerve, a splanchnic nerve, etc.

In aspects, the method of stimulation may be accomplished with a stimulation device in accordance with the present disclosure, a pacing device, a splanchnic nerve stimulation device, an implantable stimulation device, a sensory receptor massage, combinations thereof, or the like.

According to aspects there is provided, use of a sympathectomy procedure, a renal denervation procedure, a carotid body denervation procedure, combinations thereof, or the like to treat, relieve one or more symptoms related to, slow the progression of, and/or prevent the onset of CP, BPH, LUTS, nocturia, PrCa, combinations thereof, and the like.

According to aspects there is provided, use of a method in accordance with the present disclosure to treat, slow, reduce the symptoms thereof, and/or prevent the development of a disease state associated with an organ in a subject. Some non-limiting examples of disease states include LUTS, BPH, ED, CP, nocturia, PrCa, HG, combinations thereof, and the like.

According to aspects there is provided, a method for treating prostate cancer (PrCa), benign prostatic hyperplasia (BPH), and/or chronic prostatitis (CP) associated with a prostate of a subject including altering the function of one or more nerves or neural receptors belonging to and/or coupled to a prostatic plexus of the subject.

EXAMPLE

The following, non-limiting example, is directed to treatment of cancer (e.g., pancreatic cancer), internal pain or neural mediated hyperplasia in organs (e.g., benign prostatic hyperplasia). Pancreatic carcinoma cells (Mia PaCa2) were injected into the head of the pancreas of 10 athymic nude mice (subjects). A bolus of ethanol (50-75 uL) was administered to the celiac ganglion and surrounding nerves of five of the mice (i.e., the EtOH ablation group). The remaining five subjects constitute the untreated control group.

The mice were tracked for 7 weeks post procedure. Tumor growth rates in all subjects were monitored via bioluminescent imaging with an in vivo imaging system, i.e., IVIS® Spectrum (Xenogen), twice weekly during the experiment. IVIS® images from the median subject in each group at 3 weeks post procedure are shown in FIG. 20a. In FIG. 20a, the treatment arm appears to show a substantially decreased tumor growth rate compared with the control arm (nearly a 100× difference in bioluminescence between the median responders). A logarithmic comparison between groups of the tumor luminescence for each subject at 3 weeks is shown in FIG. 20b. Overall, the mean tumor size in the experimental group is half of that of the control group (1-sided, alpha=0.05, n=5, p=0.11). In addition, the median tumor size at 3 weeks is less than 1% of the control group median tumor size. As shown in FIG. 20b, a subset of the experimental group did not respond to treatment, as complete neural ablation was likely not achieved in this sub group due to the exceptionally small and delicate nature of the murine target arteries.

The experiment was terminated at 7 weeks. FIG. 20c illustrates that there was no overall size difference between subjects in the groups at 7 weeks. Thus, giving at least initial indication that the procedure is safe.

The metastases per group were assessed during necropsy. The results are shown in Tables 1 and 2 below. As shown, even with the non-responder sub-group, the incidence of metastases were considerably lower in the EtOH-treated group than in the untreated control group. Tables 1 and 2 show that the overall rate of metastases to nearby sites including local invasion, the stomach, and the liver were less in the EtOH-treated group than in the untreated control group. The two groups had the same incidence of metastases traveling to the spleen. Note that the nerves running from the pancreas to the spleen were not treated during this experiment, but the procedure disclosed herein may be applied to such nerves in large animals and humans so as to treat this pathway separately or in combination with the treatment of other anatomical sites in the vicinity of the target organ. Results demonstrate that overall, there was less tumor mass in subjects with ablated peri-pancreatic nerves than in subjects of the control group, fewer metastases in the ablated group, and similar overall body weights between the ablated group and the control group.

TABLE 1

Occurrence of metastases by subject

| Mouse # | Control Group | EtOH Ablation Group |
|---|---|---|
| 1 | Local invasion, spleen | spleen |
| 2 | Local invasion | Local invasion, spleen |
| 3 | Local invasion, spleen | none |
| 4 | Local invasion, spleen, liver | Local invasion, spleen |
| 5 | Local invasion, spleen, liver, stomach | spleen |

TABLE 2

| Occurrence of metastases by group | | |
|---|---|---|
| Metastasis Site | Control Group | EtOH ablation Group |
| Local invasion | 5/5 | 2/5 |
| Spleen | 4/5 | 4/5 |
| Liver | 2/5 | 0/5 |
| Stomach | 1/5 | 0/5 |

Embodiments of the invention safely and effectively monitor and quantify sympathetic nerve activity from the porcine renal artery lumen, organ parenchyma, and renal adventitia, with a clinically meaningful approach. Moreover, embodiments of the invention demonstrate that physiologic signals can be monitored and used as feedback to indicate completion of an ablation or neuromodulation procedure. Still further, embodiments of the invention show that tumor growth and metastases may be slowed by peri-pancreatic autonomic nerve ablation in an established and validated murine model of pancreatic cancer.

Embodiments of the invention locate (via sensing) and safely ablate pancreatic afferent/efferent neural control traffic to treat cancer, for example, but not limited to, pancreatic cancer. In humans, the sensing-ablation techniques disclosed herein may enhance quality and quantity of life by at least the following mechanisms: relieve cancer pain safely, simply, and rapidly in patients suffering this fatal disease; improve blood glucose control resulting from tumor-induced beta cell destruction; and improve survival through limiting inflammation and metastases pathways.

Embodiments of the invention can be applied to any cancer, internal pain, or organ hyperplasia treatments. The methodologies and systems described herein may be applied to all solid cancers and in particular, perineural invading cancers. While the focus of illustrative embodiments described herein is not on ablating cancerous tissue, the methodologies and systems described herein may be applied thereto.

Embodiments of the invention may be used to block or slow cancer progression by: 1) reducing neurotransmitter release in the tumor microenvironment that drives tumor growth (e.g., adrenaline); 2) disconnecting the microenvironment receptors from the CNS (to treat the cancer pain); and 3) blocking off the nerve pathways, which the cancer cells migrate along during metastasis. Embodiments of the invention may be used to treat any neurally mediated hyperplasia in organs, for example, but not limited to, benign prostatic hyperplasia (BPH). The methodologies and systems described herein may also be used for blocking internal organ pain, for example, but not limited to, in treating pancreatitis and general abdominal pain.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. An apparatus comprising:
an elongate member comprising a distal tip, the distal tip configured to fit within a lumen of a body of a subject, the elongate member configured to extend from outside the body, through an entry site on the body, and into the lumen;
wherein the distal tip comprises a plurality of elements, the plurality of elements arranged on the distal tip such that biasing the distal tip engages one or more of the plurality of elements with a wall of the lumen;
wherein the plurality of elements comprises at least one chemical delivery element and at least one sensory circuit, the at least one chemical delivery element comprising one or more probes, at least one of the one or more probes being configured to penetrate through the wall responsive to actuation by a controller;
wherein at least one of the one or more probes is configured, responsive to feedback from the at least one sensory circuit, to deliver a composition of matter to a tissue site beyond the wall of the lumen to apply a block to a target region of the subject; and
wherein the composition of matter comprises at least one of a neurolytic agent and an inflammatory agent for use in blocking at least one of one or more nerves and one or more lymphatic ducts in the target region;
wherein the feedback from the at least one sensory circuit comprises a quantification of nerve activity of the one or more nerves in the target region.

2. The apparatus of claim 1, wherein the at least one sensory circuit is configured to monitor distribution of the composition of matter into the target region.

3. The apparatus of claim 2, wherein the plurality of elements further comprises two or more electrodes, and wherein the at least one sensory circuit is configured to monitor impedance between the two or more electrodes to at least one of determine and control a quantity of the composition of matter delivered to the target region.

4. The apparatus of claim 1, wherein the feedback from the at least one sensory circuit further comprises a measure of isolation of at least one of a tumor and a metastatic cell within the body provided by application of the block to the target region.

5. The apparatus of claim 4, wherein the measure of isolation comprises a measure of a growth rate of at least one of the tumor and the metastatic cell.

6. The apparatus of claim 1, wherein the feedback from the at least one sensory circuit comprise a measure of alteration of a structure of a perineural sheath of at least one of the one or more nerves.

7. The apparatus of claim 1, wherein the feedback from the at least one sensory circuit comprises a measure of architectural destruction of at least one of nerve tissue and lymphatic ductal tissue via inflammation.

8. The apparatus of claim 1, wherein the feedback from the at least one sensory circuit comprises a measure of formation of scar tissue along at least one of the one or more nerves and the one or more lymphatic ducts.

9. The apparatus of claim 1, wherein at least one of the one or more probes is configured to apply the block to the target region by injecting the neurolytic agent of the composition of matter into at least one of the one or more nerves, the one or more lymphatic ducts, and tissue nearby at least one of the one or more nerves and the one or more lymphatic ducts.

10. The apparatus of claim 1, wherein at least one of the one or more probes is configured to apply the block to the target region by injecting the inflammatory agent of the composition of matter into at least one of the one or more nerves and the one or more lymphatic ducts.

11. The apparatus of claim 1, wherein at least one of the one or more probes is configured to apply the block to at least one of a nerve and a lymphatic duct at least 10 mm in length.

12. The apparatus of claim 1, wherein at least one of the one or more probes is configured to apply the block to at least one of a nerve and a lymphatic duct traveling along a lumen coupling a first organ to a least a second organ in the body.

13. The apparatus of claim 1, wherein the neurolytic agent of the composition of matter comprises ethanol.

14. The apparatus of claim 1, wherein the inflammatory agent of the composition of matter comprises one or more of ethanol, poly(lactic-co-glycolic acid) (PLGA), polysaccharides, collagen, silica particles, carbon micro or nanoparticles, and microbeads.

15. The apparatus of claim 1, wherein the composition of matter further comprises one or more of an ablative agent, a migration limiting agent and an inflammatory accelerating agent.

16. The apparatus of claim 1, wherein the composition of matter further comprises one or more of a medicament, a denervating agent, a sympathetic denervating agent, a parasympathetic nerve specific denervating agent, a neuroblocking agent, and a highly specific neuroblocking agent.

17. A method comprising:
  delivering a distal tip of an elongate member of a surgical tool into a lumen of a body of a subject, the distal tip being configured to fit within the lumen, the elongate member being configured to extend from outside the body of the subject, through an entry site on the body, and into the lumen;
  biasing the distal tip to engage one or more of a plurality of elements arranged upon the distal tip with a wall of the lumen, the plurality of elements comprising at least one chemical delivery element and at least one sensory circuit, the at least one chemical delivery element comprising one or more probes;
  actuating a controller to penetrate at least one of the one or more probes through the wall;
  delivering a composition of matter, via at least one of the one or more probes responsive to feedback from the at least one sensory circuit, to a tissue site beyond the wall of the lumen to apply a block to a target region of the subject;
  wherein the composition of matter comprises at least one of a neurolytic agent and an inflammatory agent for use in blocking at least one of one or more nerves and one or more lymphatic ducts in the target region; and
  wherein the feedback from the at least one sensory circuit comprises a quantification of nerve activity of the one or more nerves in the target region.

18. The method of claim 17, further comprising monitoring distribution of the composition of matter into the target region utilizing the at least one sensory circuit.

19. The method of claim 18, wherein the plurality of elements further comprises two or more electrodes, and further comprising utilizing the at least one sensory circuit to monitor impedance between the two or more electrodes to at least one of determine and control a quantity of the composition of matter delivered to the target region.

20. The method of claim 17, wherein the feedback from the at least one sensory circuit further comprises a measure of isolation of at least one of a tumor and a metastatic cell within the body provided by application of the block to the target region.

21. The method of claim 20, wherein the feedback from the at least one sensory circuit further comprises a measure of a growth rate of at least one of the tumor and the metastatic cell.

22. The method of claim 17, wherein the neurolytic agent of the composition of matter comprises ethanol.

23. The method of claim 17, wherein the inflammatory agent of the composition of matter comprises one or more of ethanol, poly(lactic-co-glycolic acid) (PLGA), polysaccharides, collagen, silica particles, carbon micro or nanoparticles, and microbeads.

24. The method of claim 17, wherein delivering the composition of matter comprises injecting at least one of the neurolytic agent of the composition of matter and the inflammatory agent of the composition of matter into at least one of the one or more nerves, the one or more lymphatic ducts, and tissue nearby at least one of the one or more nerves and the one or more lymphatic ducts.

* * * * *